(12) United States Patent
Smith et al.

(10) Patent No.: US 8,163,566 B2
(45) Date of Patent: Apr. 24, 2012

(54) MICROPOROUS MATERIALS, METHODS OF MAKING, USING, AND ARTICLES THEREOF

(75) Inventors: Roger E. Smith, Ivins, UT (US); Karl V. Voelkerding, Salt Lake City, UT (US); Marc G. Elgort, Salt Lake City, UT (US); Jacob Durtschi, Cedar Hills, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 12/367,322

(22) Filed: Feb. 6, 2009

(65) Prior Publication Data

US 2009/0142748 A1 Jun. 4, 2009

Related U.S. Application Data

(60) Division of application No. 10/853,808, filed on May 26, 2004, now Pat. No. 7,597,936, which is a continuation-in-part of application No. PCT/US03/37598, filed on Nov. 20, 2003.

(60) Provisional application No. 60/429,093, filed on Nov. 26, 2002, provisional application No. 60/429,259, filed on Nov. 26, 2002.

(51) Int. Cl.
*G01N 33/543* (2006.01)
(52) U.S. Cl. .................................................. 436/518
(58) Field of Classification Search .................. None
See application file for complete search history.

(56) References Cited

U.S. PATENT DOCUMENTS

| | | | |
|---|---|---|---|
| 3,632,417 A | 1/1972 | Brasen | 117/135.5 |
| 4,042,335 A | 8/1977 | Clement | 23/253 |
| 4,110,079 A | 8/1978 | Schaeffer et al. | 422/56 |
| 4,304,675 A | 12/1981 | Corey et al. | 8/142 |
| 4,331,619 A | 5/1982 | Chung et al. | 264/13 |
| 4,342,566 A | 8/1982 | Theofilopoulos et al. | 436/507 |
| 4,437,429 A | 3/1984 | Goldstein et al. | 119/173 |
| 4,683,195 A | 7/1987 | Mullis et al. | 435/6 |
| 4,683,202 A | 7/1987 | Mullis | 435/91.2 |
| 4,699,717 A | 10/1987 | Riesner et al. | 536/25.4 |
| 4,704,692 A | 11/1987 | Ladner | 703/11 |
| 4,767,670 A | 8/1988 | Cox et al. | 428/403 |
| 4,793,833 A | 12/1988 | Lok et al. | 95/117 |
| 4,816,567 A | 3/1989 | Cabilly et al. | 530/387.3 |
| 4,868,105 A | 9/1989 | Urdea et al. | 435/6 |
| 4,963,490 A | 10/1990 | Churchouse et al. | 435/401 |
| 4,965,188 A | 10/1990 | Mullis et al. | 435/6 |
| 5,057,426 A | 10/1991 | Henco et al. | 435/270 |
| 5,120,643 A | 6/1992 | Ching et al. | 435/7.92 |
| 5,130,238 A | 7/1992 | Malek et al. | 435/91.21 |
| 5,213,964 A | 5/1993 | Jones | 435/11 |
| 5,294,870 A | 3/1994 | Tang et al. | 313/504 |
| 5,324,633 A * | 6/1994 | Fodor et al. | 435/6 |
| 5,354,668 A | 10/1994 | Auerbach | 435/91.1 |
| 5,389,471 A | 2/1995 | Kung | 429/206 |
| 5,427,930 A | 6/1995 | Birkenmeyer et al. | 435/91.52 |
| 5,455,166 A | 10/1995 | Walker | 435/91.2 |
| 5,565,332 A | 10/1996 | Hoogenboom et al. | 435/69.1 |
| 5,582,988 A | 12/1996 | Backus et al. | 435/6 |
| 5,643,721 A | 7/1997 | Spring et al. | 435/6 |
| 5,652,348 A | 7/1997 | Burton et al. | 536/20 |
| 5,658,548 A | 8/1997 | Padhye et al. | 423/335 |
| 5,660,984 A | 8/1997 | Davis et al. | 435/6 |
| 5,712,383 A | 1/1998 | Sheridan et al. | 536/24.3 |
| 5,716,526 A | 2/1998 | Kelemen et al. | 210/650 |
| 5,721,367 A | 2/1998 | Kay et al. | 800/18 |
| 5,804,440 A | 9/1998 | Burton et al. | 435/339.1 |
| 5,807,756 A | 9/1998 | Bauman et al. | 436/524 |
| 5,837,243 A | 11/1998 | Deo et al. | 424/136.1 |
| 5,843,767 A * | 12/1998 | Beattie | 435/287.1 |
| 5,856,192 A | 1/1999 | Bloch | 436/18 |

(Continued)

FOREIGN PATENT DOCUMENTS

WO WO 94/29348 12/1994

OTHER PUBLICATIONS

Ansdell et al., "Automotive Paints." Chapter 10 from R. Lambourne and T.A. Strivens, Eds., Paint and Surface Coatings: Theory and Practice, Second Edition, Woodhead Publishing Ltd., pp. 411-491, 1999.

Boerner et al. "Production of antigen-specific human monoclonal antibodies from in vitro-primed human splenocytes." *J Immunol.* 147(1):86-95, 1991.

Bruggermann et al., "Designer mice: the production of human antibody repertoires in transgenic animals." *Year Immunol.* 7:33-40, 1993.

Elgort et al., "Extraction and Amplification of Genomic DNA from Whole Blood on a Nanoporous Surface," Presented at The Association for Molecular Pathology Meeting, Orlando, FL Nov. 20-23, 2003.

(Continued)

*Primary Examiner* — Ann Lam
(74) *Attorney, Agent, or Firm* — Ballard Spahr LLP

(57) ABSTRACT

Described herein are methods for separating one or more analytes present in a fluid sample. The methods involve passing the fluid through or into a microporous material, wherein the analytes are localized near the surface of the microporous material. Additional processing steps such as hybridization and amplification can be performed once the analyte is localized. In one method, once the analyte is localized, the analyte can be detected, counted, and correlated in order to determine the concentration of the analyte in the sample. In another method, the localized analyte is destabilized to make the localized analyte more accessible for chemical manipulation. Modified microporous materials and composite materials are also disclosed that can be used in any of the methods and articles described herein. The composite is composed of a microporous material and a pigment, wherein the pigment is incorporated in the microporous material. The pigments alter the optical properties of the microporous material, which enhances the detection of analyte once it is localized. Methods for making pigmented composites are also disclosed. In a further aspect, various kits and articles such as filtration devices containing any of the microporous materials described herein are provided.

19 Claims, 44 Drawing Sheets

U.S. PATENT DOCUMENTS

| | | | | |
|---|---|---|---|---|
| 5,906,747 | A | * | 5/1999 | Coffman et al. ............... 210/635 |
| 5,939,598 | A | | 8/1999 | Kucherlapati et al. ........... 800/25 |
| 5,955,351 | A | | 9/1999 | Gerdes et al. ............... 435/287.2 |
| 5,958,714 | A | * | 9/1999 | Gordon et al. ............... 435/7.92 |
| 5,959,014 | A | | 9/1999 | Liebeskind et al. ........... 524/389 |
| 5,972,613 | A | | 10/1999 | Somack et al. .................... 435/6 |
| 5,985,514 | A | | 11/1999 | Zheng et al. ............... 430/270.1 |
| 6,096,441 | A | | 8/2000 | Hauser et al. ................. 428/668 |
| 6,130,364 | A | | 10/2000 | Jakobovits et al. ............... 800/6 |
| 6,180,377 | B1 | | 1/2001 | Morgan et al. ............. 424/133.1 |
| 6,225,131 | B1 | | 5/2001 | van Damme et al. ......... 436/524 |
| 6,284,232 | B1 | | 9/2001 | Calton et al. ................. 424/76.1 |
| 6,291,166 | B1 | | 9/2001 | Gerdes et al. ...................... 435/6 |
| 6,310,199 | B1 | | 10/2001 | Smith et al. .................. 536/25.4 |
| 6,319,469 | B1 | * | 11/2001 | Mian et al. ....................... 422/64 |
| 6,361,940 | B1 | * | 3/2002 | Van Ness et al. ................. 435/6 |
| 6,423,444 | B1 | | 7/2002 | Ying et al. .................... 429/129 |
| 6,428,748 | B1 | | 8/2002 | Wallach .......................... 422/56 |
| 6,475,663 | B1 | | 11/2002 | Mohwald et al. ............. 426/129 |
| 6,558,902 | B1 | * | 5/2003 | Hillenkamp ...................... 506/6 |
| 6,623,908 | B2 | | 9/2003 | Zheng et al. ............... 430/270.1 |
| 6,630,018 | B2 | | 10/2003 | Bauer et al. ................... 106/415 |
| 6,635,420 | B1 | | 10/2003 | Hosel et al. ....................... 435/6 |
| 6,649,083 | B1 | | 11/2003 | Pinnavaia et al. ............. 252/179 |
| 6,766,817 | B2 | | 7/2004 | Da Silva ........................... 137/1 |
| 6,843,945 | B1 | | 1/2005 | Lee et al. ........................ 264/49 |
| 6,955,901 | B2 | * | 10/2005 | Schouten ..................... 435/91.1 |
| 6,991,847 | B2 | | 1/2006 | Padmanabhan et al. ... 428/316.6 |
| 7,597,936 | B2 | | 10/2009 | Smith et al. |
| 7,645,571 | B2 | * | 1/2010 | Anthony et al. .................. 435/6 |
| 7,682,688 | B2 | | 3/2010 | Smith et al. |
| 2001/0018513 | A1 | | 8/2001 | Baker ......................... 536/25.41 |
| 2001/0046785 | A1 | | 11/2001 | Gole et al. .................... 438/753 |
| 2003/0148354 | A1 | * | 8/2003 | Gordon ............................ 435/6 |
| 2004/0002154 | A1 | * | 1/2004 | Palsson ........................ 435/446 |
| 2004/0148015 | A1 | | 7/2004 | Lee et al. ..................... 623/1.15 |

OTHER PUBLICATIONS

Erali et al., "Localization, Visualization and Quantitation of Individual Nucleic Acid Molecules on a Nanoporous Surface", Presented at The Association for Molecular Pathology, Orlando, FL Nov. 20-23, 2003.

Fodor et al. "Light-directed, spatially addressable parallel chemical synthesis." *Science*. 251(4995):767-73, 1991.

Herrmann et al., "A System for Sample Processing, DNA Amplification and Amplicon Detection on a Single Nanoporous Surface", Presented at The Association of Molecular Pathology, Orlando, FL Nov. 20-23, 2003.

Hoogenboom et al., "By-passing hybridization. Human antibodies from synthetic repertoires of germline VH gene segments rearranged in vitro." *J Mol Biol*. 227(2):381-8, 1991.

International Search Report & Written Opinion for PCT/US03/017295 mailed Dec. 31, 2003.

International Search Report & Written Opinion for PCT/US03/037598 mailed Sep. 20, 2005.

Jakobovits et al, "Analysis of homozygous mutant chimeric mice: deletion of the immunoglobulin heavy-chain joining region blocks B-cell development and antibody production." *Proc Natl Acad Sci U S A*. 90(6):2551-5, 1993.

Jakobovits et al., "Germ-line transmission and expression of a human-derived yeast artificial chromosome." *Nature*. 362(6417):255-8, 1993.

Jones et al., "Replacing the complementarity-determining regions in a human antibody with those from a mouse." *Nature*. 321(6069):522-5, 1986.

Kohler and Milstein, "Continuous cultures of fused cells secreting antibody of predefined specificity." *Nature*. 256(5517):495-7, 1975.

Letsinger et al., "Cholesteryl-conjugated oligonucleotides: Synthesis, properties, & activ. as inhibitors of replication," *Proc. Natl. Acad. Sci. U.S.A* 86:6553-6556 (1989).

Marks et al., "By-passing immunization. Human antibodies from V-gene libraries displayed on phage." *J Mol Biol*. 222(3):581-97. 1991.

Milka et al. "Immobilization of Alliinase on Porous Aluminum Oxide," *Biotechnology and Bioengineering*. 69(3):344-348, 2000.

*Monoclonal Antibodies and Cancer Therapy*, Proceedings of the Roche-UCLA Symposium Held in Park City, Utah Jan. 26-Feb. 2, 1985, Reisfeld and Sell eds., Alan R. Liss, New York, p. 77, 1985.

Morrison et al., "Chimeric human antibody molecules: mouse antigen-binding domains with human constant region domains." *Proc Natl Acad Sci U S A*. 81(21):6851-5, 1984.

Presta, "Antibody Engineering," *Curr. Opin. Struct. Biol.*, 2:593-596 (1992).

Riechmann et al., "Reshaping human antibodies for therapy." *Nature*. 332(6162):323-7, 1988.

Rigby et al., "An anodising process for production of inorganic microfiltration membranes," *Trans. Inst. Metal Finish* 62(3):95, 1990.

Southern et al. "Arrays of complementary oligonucleotides for Hybridization the Hybridization behaviour of nucleic acids." *Nucleic Acids Res*. 22(8):1368-73, 1994.

Verhoeyen et al., "Reshaping human antibodies: grafting an antilysozyme activity." *Science*. 239(4847):1534-6, 1988.

Zoller, "New recombinant DNA methodology for protein engineering." *Curr Opin Biotechnol*. 3(4):348-54, 1992.

Malins et al., "Influence of the surface polarity of dye-doped sol-gel glass films on optical ammonia sensor response," *Thin Solid Films* 368:105-110 (2000).

Ichinose et al., "Wrapping and inclusion of organic molecules with ultrathin, amorphous metal oxide films," *Chem. Rec*. 2(5):339-351 (2002).

U.S. Appl. No. 10/536,287, Smith, filed Jul. 8, 2005, Amendment/Req. Reconsideration-After Non-Final Reject, Oct. 5, 2009.

U.S. Appl. No. 10/536,287, Smith, filed Jul. 8, 2005, Non-Final Rejection, Jun. 8, 2009.

U.S. Appl. No. 10/536,287, Smith, filed Jul. 8, 2005, Notice of Appeal Filed, Sep. 26, 2008.

U.S. Appl. No. 10/536,287, Smith, filed Jul. 8, 2005, Advisory Action (PTOL-303), Jul. 1, 2008.

U.S. Appl. No. 10/536,287, Smith, filed Jul. 8, 2005, Amendment After Final, Jun. 27, 2008.

U.S. Appl. No. 10/536,287, Smith, filed Jul. 8, 2005, Final Rejection, Mar. 28, 2008.

U.S. Appl. No. 10/536,287, Smith, filed Jul. 8, 2005, Amendment/Req. Reconsideration-After Non-Final Reject, Jan. 22, 2008.

U.S. Appl. No. 10/536,287, Smith, filed Jul. 8, 2005, Non-Final Rejection, Sep. 24, 2007.

U.S. Appl. No. 10/536,287, Smith, filed Jul. 8, 2005, Applicant Arguments/Remarks Made in an Amendment, Sep. 10, 2007.

U.S. Appl. No. 10/536,287, Smith, filed Jul. 8, 2005, Examiner Interview Summary Record (PTOL-413), Aug. 31, 2007.

U.S. Appl. No. 10/536,287, Smith, filed Jul. 8, 2005, Final Rejection, Jun. 21, 2007.

U.S. Appl. No. 10/536,287, Smith, filed Jul. 8, 2005, Amendment/Req. Reconsideration-After Non-Final Reject, May 7, 2007.

U.S. Appl. No. 10/536,287, Smith, filed Jul. 8, 2005, Non-Final Rejection, Dec. 13, 2006.

U.S. Appl. No. 10/536,287, Smith, filed Jul. 8, 2005, Applicant Arguments/Remarks Made in an Amendment, Nov. 20, 2006.

U.S. Appl. No. 10/536,287, Smith, filed Jul. 8, 2005, Amendment/Response to Restriction Requirement, Nov. 1, 2006.

U.S. Appl. No. 10/536,287, Smith, filed Jul. 8, 2005, Restriction Requirement, Aug. 9, 2006.

U.S. Appl. No. 10/536,287, Smith, filed Jul. 8, 2005, Preliminary Amendment, May 25, 2005.

JP, 2004-555704, May 24, 2005, Univ. of Utah Research Foundation, Office Action, Jul. 27, 2009.

PCT/US03/37598, Nov. 20, 2003, Univ. of Utah Research Foundation, International Search Report, Nov. 17, 2005.

PCT/US2005/017295, May 17, 2005, Univ. of Utah Research Foundation, International Search Report, Dec. 7, 2006.

PCT/US2005/017295, May 17, 2005, Univ. of Utah Research Foundation, International Search Report on Patentability Chapter I, Nov. 26, 2006.

PCT/US2005/017295, May 17, 2005, Univ. of Utah Research Foundation, Written Opinion of the International Search Authority, Sep. 26, 2006.

* cited by examiner

CONC.=1, OBJECTS=171

CONC.=2, OBJECTS=253

CONC.=4, OBJECTS=399

CONC.=8, OBJECTS=592

CONC.=16, OBJECTS=881

CONC.=32, OBJECTS=1247

CONC.=64, OBJECTS=1247

CONC.=128, OBJECTS=1473

MICROPOROUS MATERIALS, METHODS OF MAKING, USING, AND ARTICLES THEREOF

CROSS REFERENCE TO RELATED APPLICATIONS

This application is a divisional of U.S. application Ser. No. 10/853,808, filed May 26, 2004, now U.S. Pat. No. 7,597,936, which is a continuation-in-part of International Application No. PCT/US2003/037598, filed on Nov. 20, 2003, which claims the benefit of priority to U.S. Provisional Application Ser. Nos. 60/429,093 and 60/429,259, both filed Nov. 26, 2002. These applications are hereby incorporated by this reference in their entireties for all of their teachings.

BACKGROUND

The quantification and identification of analytes present in samples derived from a subject is important in the medical arena. In particular, the quantification and identification of analytes from a sample can greatly assist in the diagnoses and treatment of numerous diseases.

For example, nucleic acid analysis is a widely used technique in medical diagnostics. Current techniques of nucleic acid analysis routinely quantify several hundred molecular copies of target nucleic acids per milliliter of patient sample. This requires substantial molecular multiplication, often through a polymerase chain reaction (PCR), to achieve sufficiently high nucleic acid concentrations for detection with conventional laboratory equipment. This molecular amplification requires nucleic acid purification prior to multiplication, which is time consuming, expensive, difficult to control, and has limited accuracy. The final assay result is highly dependent on closely controlling several multistep processes. Currently, available viral load assays report log (rather than linear) values of nucleic acid concentration, at least in part due to limited precision and accuracy inherent in current techniques.

The amplification techniques described above require purified nucleic acid samples free of competing or interfering contaminants. Contaminants can be present in the sample and may include enzymes, proteins, hemoglobin, bacteria, particulate, etc. Alternatively, contaminants can come from the purification system used and may include organic solvents, salts, metal ions, etc. Removing contaminants that interfere with nucleic acid amplification (reverse transcription, amplification, etc.) as well as removing contaminating substances that interfere with detection (hybridization, fluorescence, etc.) requires undertaking time-consuming processes.

Techniques exist to purify nucleic acids. For example, multiple organic reagent extraction/precipitation using chloroform, phenol, and lower alcohols have been used for many years to isolate and purify nucleic acids for subsequent analysis. Additional purification techniques include chromatographic techniques using ion-exchange chromatography, reversed phase chromatography, affinity chromatography, and various combinations thereof.

Silica based nucleic acid purification techniques are currently in wide commercial use. These systems purify nucleic acids through reversible binding (precipitation) onto silica and its derivatives in the presence of chaotropic agents and/or organic solvents. Typically, these systems dilute patient samples containing nucleic acids into 5+ molar guanidine thiocyanate (GTC). This mixture reacts at room temperature, then equal volumes of neat ethyl alcohol are added and vortexed. This mixture is exposed to high surface area silica, where the nucleic acids bind almost immediately. The silica is recovered, rinsed several times with solutions containing GTC and ethyl alcohol, dried, and then the bound nucleic acids are eluted with low salt water. Several versions of this technique exist, and are differentiated based on the silica-based binder used. For instance, one system uses a small filtration or spin column containing a thick silica fiber mat for binding. Other systems use glass beads, magnetic silica based beads, silica impregnated filters, etc. These systems add a carrier nucleic acid (co-precipitant) to permit isolation and purification of very low concentrations of target nucleic acid. While silica based nucleic acid purification techniques adequately perform their intended function, these techniques are time-consuming and expensive.

As with purifying nucleic acids, many techniques exist for immobilizing nucleic acids. To facilitate nucleic acid capture, surfaces are often treated with a variety of chemicals that bind to nucleic acids when the surface is contacted with a solution containing the nucleic acid. For example, covalent attachment of organic compounds to glass and aluminum oxide is known. Such attachment may involve the use of silanization reagents to completely modify the native oxide surface for control of charge, hydrophobic effects, etc., as well as to permit covalent attachment of nucleic acids, proteins, polymers, etc. to effect capture of specific target molecules to the surface. Quartz, glass, and silicon substrates with various surface chemistries have been used to capture nucleic acids for optical molecular detection. These techniques require target nucleic acids to diffuse to the reactive surface for immobilization or capture. At low concentrations, these diffusion-controlled reactions require hours to complete. These techniques are time-consuming, expensive, and may not be suitable for rapid optical molecular detection techniques.

Accordingly, it would be desirable to have materials, devices, and methods for the rapid, inexpensive, and efficient isolation of an analyte from a sample. It is also desirable to remove any contaminants that may interfere with further manipulation (e.g., quantification and identification) of the analyte once it has been removed from the sample.

SUMMARY

Described herein are compositions, methods, devices, and machines for separating one or more analytes present in a fluid sample. In one aspect, the method involves passing the fluid through a filter composed of a microporous material, wherein the analytes are localized near the surface of the microporous material. Additional processing steps such as hybridization and amplification can be performed once the analyte is localized on the microporous material. In one aspect, once the analyte is localized on the microporous material, the analyte can be detected, counted, and/or correlated in order to determine the concentration of the analyte in the sample having a known volume.

In another aspect, composite materials are disclosed. In certain embodiments, these composites can be used in any of the methods and articles described herein. The composite is composed of a microporous material and a pigment, wherein the pigment is incorporated in the microporous material. The pigments alter the optical properties of the microporous material, which enhances the detection of analyte once it is localized near the surface of the composite.

In another aspect, modified microporous materials are disclosed composed of a microporous material and a suspension matrix, wherein the suspension matrix is localized near the surface of the microporous material.

In a further aspect, various kits and articles such as filtration devices containing any of the microporous materials or as described herein are provided.

The advantages of the microporous materials, methods, articles, and machines described herein will be set forth in part in the description which follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below. It will be appreciated that these drawings depict only typical embodiments of the microporous materials, articles, and methods described herein and are therefore not to be considered limiting of their scope.

DETAILED DESCRIPTION

Figure 1A:
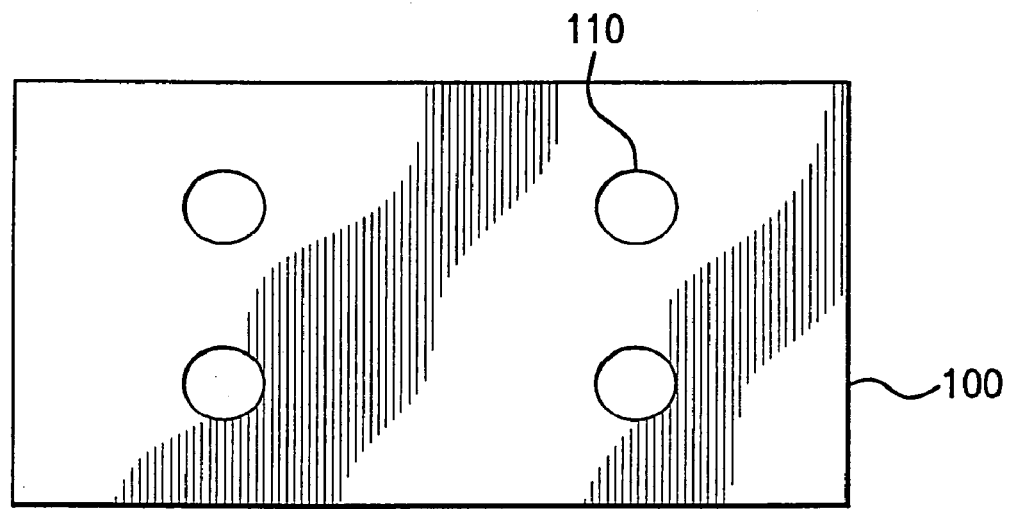
FIG. 1a is a top-view of the microporous material.

A. Compositions and Methods for Separating and Analyzing Analytes

There are many situations in which it is desirable to be able to separate or analyze an analyte from or in a given sample. An analyte can be any target substance, which is to be analyzed, for example, in a sample. For example, in disease diagnoses, often there is a particular analyte that is produced by, or part of, a pathogen, and physicians use the presence or absence of that analyte to determine whether the patient is infected with the pathogen. There are many characteristics and parameters that affect this type of determination, such as the efficiency of detection, how sensitive the detection methods are, the amount of analyte produced by the pathogen, the amount of sample needed to perform the analysis, the stability of the analyte, the amount of background analyte present in the sample, and so forth. Methods and compositions which increase the sensitivity of detection and the ease with which an analyte can be detected are desirable.

Typically the methods involve manipulating the analytes in sample, by for example, separating the analytes from the sample, localizing the analytes, analyzing the analytes, by for example, counting the number of analytes separated, correlating the number of analytes counted to the number of analytes in the sample, purifying the analytes, and collecting the analytes, for example, after one or more other manipulation activities are completed. These steps and others can be performed one after the other or many or all of them can be performed together.

Described herein are methods for separating one or more analytes present in a sample, such as a fluid sample. Typically the fluid sample will have a known volume, which facilitates certain types of analysis of the analyte. "Separating an analyte from a fluid sample" means removing the analyte from the sample, such as the fluid sample. The amount and precision of analyte separation from the sample can vary. In one aspect, qualitative determination for the presence or absence of the analyte may be performed on less precise and less efficient analyte separation from the sample. In another aspect, analyte is separated with increased precision and efficiency. In this aspect, the separated analyte can be subjected to further manipulation, such as quantification discussed herein. The purity of the separated analyte will also vary, ranging from very pure to an analyte containing impurities from the sample. Purification of at least 2, 5, 10, 25, 50, 75, 100, 150, 250, 500, 750, 1,000, 5,000, 10,000, and 25,000 fold relative to the starting sample can be achieved.

In one aspect, the method involves passing the sample, such as the fluid sample, through a filter. Typically the filter will have or be made from a microporous material. When the sample is passed through the filter, the analytes can be localized near the surface of the filter. The disclosed filters and microporous materials can have many different surfaces, such as a planar surface, an external surface, an internal surface, a wetted surface, and a channel surface. Often the analytes are passed through a microporous material. A microporous material is any material having a plurality of pores, holes, and/or channels. The microporous material permits the flow of liquid through or into the material.

In certain embodiments the materials are localized and this localization is reversible, and in other embodiments the localization is irreversible. The localization can also include the characteristic of being immobilized, which means that the analyte is retained in a defined area long enough to be analyzed, for example, counted or assayed.

The characteristics of the filter and the microporous material affect the parameters of separating and/or manipulating the analyte in the sample. In certain embodiments the microporous material is a composite or modified microporous material, and these composites are discussed herein. Often it is desirable to detect the analytes that have been localized, by for example, viewing them directly or assaying for some type of label that has been associated with the analyte. This has been traditionally performed by what may be termed an analog signal detection technique, where all analytes contribute to an "ensemble" signal that is representative of the number of analytes localized to the microporous surface. Additionally, the techniques disclosed herein allow for what may be termed digital detection or analyte molecular counting. As discussed in further detail below, molecular counting of the analyte is affected by a number of different parameters including, the actual detectable signal from the analyte molecule or label and the amount of background signal observed by the detection method. Furthermore, there is a threshold level of signal that is required for detection and this threshold level is different for each detection method used. Thus, to be able to "count" a particular analyte that has been localized on the planar surface of a filter, the absolute detectable signal from the analyte molecule or label that is localized needs to be high enough so that there is signal observed from the analyte that is above the background signal for the detection method, and which is above the absolute threshold for signal detection or the analyte could be localized but not counted. As discussed herein, any of the microporous materials described herein can be used in filters to decrease the background signal produced by the filter for a particular detection method. For analog detection, this decrease in background signal allows for the detection of fewer absolute numbers of an analyte because a smaller signal is required from the analytes to be observed over the background signal. For digital detection such as molecular counting, this decrease in background signal allows better resolution of individual molecules and greatly improves molecular detection. Thus, the disclosed methods and compositions allow for greater sensitivity in analyte detection, i.e. they allow for detection of smaller numbers of analyte in a sample. This is desirable because it allows for use of smaller samples and tests to identify the presence or absence of an analyte and may be more sensitive and accurate, for example. As discussed herein, in certain embodiments the composites utilize a pigment to decrease the background signal.

Once the analyte has been localized near the surface of the microporous material, such as a composite or a modified microporous material, further processing steps may be performed. The analyte can also be, for example, amplified, detected, or isolated. For example, the analyte can also be counted, correlated, purified, or collected.

The microporous materials, methods, articles, and kits described herein provide improvements over conventional methods for the separation and analysis of analytes, and are more simplified than current techniques. Additionally, the microporous materials, methods, articles, and kits described herein are useful either individually as separate steps or materials or methods individually or as combinations of the disclosed materials and method steps. For example, the ability to rapidly isolate nucleic acids from a wide variety of impure substances quickly and simply through a microporous material is useful regardless of whether these isolated nucleic acids are subsequently counted.

Further discussion of the various parts of the disclosed articles and types of compositions and microporous materials, as well as various steps and sets of methods steps are set forth in more exemplary detail below.

B. Localization of Analyte

The disclosed methods generally are used for localizing an analyte in a sample. There are many different types of samples that can be used that can be a source of the analyte.

1. Samples

The samples are typically fluids because a fluid facilitates passage through the disclosed filters or microporous materials, for example. Sample fluids containing analytes include solutions or suspensions, such as solutions of molecularly dissolved materials or hydrodynamically suspended materials. Sample fluids that contain analytes include biofluids, such as whole blood, serum, plasma, cerebral spinal fluid, urine, saliva, semen, sputum, bronchalveolar lavage fluid, joint aspirate, or wound drainage. Other sample fluids that can be used include various preparations containing bacteria, viruses, fungi, spores, cell cultures, fecal excrements, animal tissues or cells, vegetable tissues or cells, lysed ingredients thereof, or combinations thereof. It is understood that a solid sample containing an analyte can be homogenized or otherwise put into solution to facilitate the analysis of the sample.

In another aspect, the source of the analyte can be an environmental sample. For example, waste water containing contaminants such as polymers or other chemicals. In another aspect, the sample could be a biowarfare sample, which is considered a sample that has been potentially contaminated with a biowarfare agent. For example, a biowarfare sample could be a water sample, such as a potable water sample, that may have been contaminated. In another aspect, the sample can be an air sample.

In another aspect, the sample can be a fluid for human consumption such as, for example, drinking water and other beverages.

i. Known Volume Samples

Often the samples will be utilized in a known volume condition. A known volume sample is one in which the volume or amount of sample is known. Typically it is important to use known volume samples if one wishes to determine the concentration of analyte present in the sample at some point during the process, but also importantly if the amount of analyte that is present in the sample is to be correlated to the amount of analyte in the organism from which the sample was obtained. For example, if one desires to know how many viral particles are present in a subject, a sample, such as a blood sample can be taken from the subject. This blood sample can be analyzed using the disclosed methods and compositions and the amount of analyte present in the sample can be determined. To determine how much analyte was present in the subject, one needs to determine how much analyte was present in the sample, in a known volume, and then extrapolate this to the amount of analyte present in the subject based on the knowledge, for example, of the total volume of, for example, the fluid in the subject.

The size of the known volume can depend on for example, the amount of analyte in the sample, the sensitivity of detection of the analyte, or the types of manipulation planned for the analyte. For example, when the sample is a blood sample, the known volume can be less than 40 µl, less than 30 µl, less than 20, less than 10 µl, or less than 5 µl for genetic testing, while samples of plasma or CSF for viral load testing may be greater than 200 µl, such as 200 µl to 10,000 µl. In another aspect, the amount of sample that contains the analyte is from 0.5 µl to 1,000 µl, 0.5 µl to 900 µl, 0.5 µl to 800 µl, 0.5 µl to 700 µl, 0.5 µl to 600 µl, 0.5 µl to 500 µl, 0.5 µl to 400 µl, 0.5 µl to 300 µl, 0.5 µl to 200 µl, 0.5 µl to 100 µl, 0.5 µl to 50 µl, 0.5 µl to 25 µl, or 0.5 µl to 10 µl. In another aspect, when the sample is an environmental sample such as water, air, etc., the volume of the sample can be larger than 1 milliliter, such as 10 mL to 1,000 mL.

2. Analyte

As indicated the disclosed compositions and methods are typically designed to manipulate analytes, for which information is desired. Any analyte that has the properties necessary for localization on the microporous material or that can be bound to a suspension matrix for localization, can be targeted or manipulated.

Numerous analytes can be localized near the surface of any of the microporous materials described herein. For example, the analyte can be a protein, a parasite, a fungus, an effector molecule, a ligand, a receptor, a signal-generating molecule, a structural molecule, an ion, an antigen, an antibody, a tissue, a cell, a bacterium, a protein, or a combination thereof. Additionally, analytes include any target molecules that are attached to a suspension matrix for localization. These types of matrices can increase localization efficiency. For example, a suspension matrix composed of DNA and an antibody can be used to specifically bind an antigen. For example, an antigen can be less than 1,000 kDa molecular weight and possibly too small for efficient localization on the microporous material. By first interacting the antigen with an antibody, attached to a nucleic acid, for example, the antigen can be more efficiently localized based on its association with the nucleic acid. In certain aspects, reaction of the target molecule with a suspension matrix can substantially improve localization efficiency. Further details of the use of a suspension matrix to increase localization efficiency are discussed below.

One way of categorizing analytes is by their size, relative to the pore size of the microporous material used to localize the analyte. For example, the analyte can have a contour length or globular diameter at least 1.5 times, two times, three times, four times, six times, eight times, ten times, or twenty times the diameter of the pores in the microporous material. It is understood that in certain embodiments the goal is to localize the analyte near the surface of the microporous material and then to detect the localized analyte. The larger the analyte is relative to the pore size the more efficiently the analyte will be localized, meaning the fewer the number of analyte molecules that will escape from the localized position by passing through the microporous material. However, it is understood that as the size of the pores are decreased, the speed at which the fluid is able to pass through the filter or material is decreased, and the higher the number of impurities that will be localized along with the desired analyte. It is considered that analyte size can be determined and that calculations can be used to determine the appropriate pore size of a material to be used, and that furthermore, empirical analysis can be used to determine or optimize the pore size as well.

i. Tissues

Samples can be obtained from any type of tissue of an organism. For example, in certain situations the tissue can be used directly, such as when the tissue is blood. However, in other situations, the tissue can be collected and then manipulated, by for example, homogenization or grinding etc.

There are four basic types of tissue. These compose all the organs, structures and other contents of an organism. There is the Epithelium tissue, which lines, covers, protects, absorbs and secretes, within or on the organism. There is connective tissue which holds other tissues and materials together. Blood is considered a connective tissue. There is muscle tissue, which contain muscle cells that contain contractile filaments that move past each other and change the size of the cell. Lastly there is nervous tissue. Examples of tissue subtypes or organs that contain more than one type of tissue would be, adipose, breast, brain, bone, intestine, stomach, skin, blood, liver, kidney, uterine, prostate, colon, urinary tract, cardiac, pulmonary, lung, muscle, ligaments, tendons, cartilage, semen, lymphatic, for example.

ii. Cells

Any type of cell can be considered an analyte. For example, eukaryotic cells and prokaryotic cells can be analytes. Examples of Eukaryotic cells that can be analytes are all types of animal cells, such as mammal cells, reptile cells, amphibian cells, and avian cells, blood cells, hepatic cells, kidney cells, skin cells, brain cells, bone cells, nerve cells, immune cells, lymphatic cells, brain cells, plant cells, and fungal cells. In another aspect, the analyte can be a component of a cell including, but not limited to, the nucleus, the nuclear membrane, leucoplasts, the microtrabecular lattice, endoplasmic reticulum, ribosomes, chromosomes, cell membrane, mitochondrion, nucleoli, lysosomes, the Golgi bodies, peroxisomes, or chloroplasts.

iii. Bacteria

Any type of bacteria can be an analyte. Examples of bacterium include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratuberculosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholerae, Ehrlichia* species, *Actinobacillus pleuropneumoniae, Pasteurella haemolytica, Pasteurella multocida,* other *Pasteurella* species, *Legionella*

*pneumophila*, other *Legionella* species, *Salmonella typhi*, other *Salmonella* species, *Shigella* species *Brucella abortus*, other *Brucella* species, *Chlamydi trachomatis*, *Chlamydia psittaci*, *Coxiella burnetti*, *Escherichia coli*, *Neiserria meningitidis*, *Neiserria gonorrhea*, *Haemophilus influenzae*, *Haemophilus ducreyi*, other *Hemophilus* species, *Yersinia pestis*, *Yersinia enterolitica*, other *Yersinia* species, *Escherichia coli*, *E. hirae* and other *Escherichia* species, as well as other Enterobacteria, *Brucella abortus* and other *Brucella* species, *Burkholderia cepacia*, *Burkholderia pseudomallei*, *Francisella tularensis*, *Bacteroides fragilis*, *Fudobascterium nucleatum*, *Provetella* species, and *Cowdria ruminantium*, or any strain or variant thereof.

iv. Virons and viruses

Any type of virus can be an analyte. Examples of viruses include, but are not limited to, Herpes simplex virus type-1, Herpes simplex virus type-2, Cytomegalovirus, Epstein-Barr virus, Varicella-zoster virus, Human herpesvirus 6, Human herpesvirus 7, Human herpesvirus 8, Variola virus, Vesicular stomatitis virus, Hepatitis A virus, Hepatitis B virus, Hepatitis C virus, Hepatitis D virus, Hepatitis E virus, Rhinovirus, Coronavirus, Influenza virus A, Influenza virus B, Measles virus, Polyomavirus, Human Papillomavirus, Respiratory syncytial virus, Adenovirus, Coxsackie virus, Dengue virus, Mumps virus, Poliovirus, Rabies virus, Rous sarcoma virus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency cirus, Human T-cell Leukemia virus type-1, Hantavirus, Rubella virus, Simian Immunodeficiency virus, Human Immunodeficiency virus type-1, Vaccinia virus, SARS virus, and Human Immunodeficiency virus type-2, or any strain or variant thereof.

v. Parasites

Any type of parasite can be an analyte. Examples of parasites include, but are not limited to, *Toxoplasma gondii*, *Plasmodium falciparum*, *Plasmodium vivax*, *Plasmodium malariae*, other *Plasmodium* species, *Trypanosoma brucei*, *Trypanosoma cruzi*, *Leishmania major*, other *Leishmania* species, *Schistosoma mansoni*, other *Schistosoma* species, and *Entamoeba histolytica*, or any strain or variant thereof.

vi. Proteins

Any type of protein can be an analyte. For example, the protein can include peptides or fragments of proteins or peptides. The protein can be of any length depending upon the pore size in the microporous material, and can include one or more amino acids or variants thereof. The protein(s) can be fragmented, such as by protease digestion, prior to analysis. A protein sample to be analyzed can also be subjected to fractionation or separation to reduce the complexity of the samples. Fragmentation and fractionation can also be used together in the same assay. Such fragmentation and fractionation can simplify and extend the analysis of the proteins.

vii. Antibodies

Any type of antibody can be an analyte. As used herein, the term "antibody" encompasses, but is not limited to, whole immunoglobulin (i.e., an intact antibody) of any class, chimeric antibodies and hybrid antibodies, with dual or multiple antigen or epitope specificities, and fragments, such as F(ab') 2, Fab', Fab and the like, including hybrid fragments. Thus, fragments of the antibodies that retain the ability to bind their specific antigens are provided. For example, fragments of antibodies which maintain binding activity are included. Such antibodies and fragments can be made by techniques known in the art. Methods for producing antibodies and screening antibodies for specificity and activity (See Harlow and Lane. Antibodies, A Laboratory Manual. Cold Spring Harbor Publications, New York, (1988)). The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. Also included within the meaning of "antibody" are conjugates of antibody fragments and antigen binding proteins (single chain antibodies) as described, for example, in U.S. Pat. No. 4,704,692, the contents of which are hereby incorporated by reference.

viii. Antigens

Any type of antigen can be an analyte. "Antigen" as used herein includes substances that upon administration are capable of eliciting an immune response, thereby stimulating the production and release of antibodies that bind specifically to the antigen. Antigens include molecules and/or moieties that are bound specifically by an antibody to form an antigen/antibody complex. Examples of antigens include, but are not limited to, peptides, polypeptides, proteins, nucleic acids, DNA, RNA, saccharides, combinations thereof, fractions thereof, or mimetics thereof.

ix. Fungi

Any type of fungus can be an analyte. Examples of fungi include, but are not limited to, *Candida albicans*, *Cryptococcus neoformans*, *Histoplama capsulatum*, *Aspergillus fumigatus*, *Coccidiodes immitis*, *Paracoccidiodes brasiliensis*, *Blastomyces dermitidis*, *Pneomocystis carnii*, *Penicillium marneffi*, and *Alternaria* alternate, and variations or different strains of these.

x. Effector Molecules

The analyte can be an effector molecule. "Effector molecules," also referred to as "effector species," "effectors," and "molecular effectors," are selected molecules capable of transforming energy into work, work into energy, work or energy into information, or information into work or energy and include, but are not limited to, signal-generating species, stimulus-response molecules, response-generating molecules, enzymes, synthetic enzymes, drugs, catalytic antibodies, catalysts, contractile proteins, transport proteins, regulatory proteins, redox proteins, redox enzymes, redox mediators, cytochromes, electroactive compounds, photoactive compounds, supermolecules, supramolecular devices and shape-memory structures, or any derivative or variant thereof.

xi. Ligands

Any type of ligand can be an analyte. The term "ligand" is a molecule capable of specifically binding to a receptor by affinity-based interaction. Ligands include, but are not limited to, receptor agonists, partial agonists, mixed agonists, antagonists, response-inducing or stimulus molecules, drugs, hormones, pheromones, transmitters, autacoids, growth factors, cytokines, prosthetic groups, coenzymes, cofactors, substrates, precursors, vitamins, toxins, regulatory factors, antigens, haptens, carbohydrates, molecular mimics, print molecules, structural molecules, effector molecules, selectable molecules, biotin, digoxigenin, and congeners, crossreactants, analogs, competitors or derivatives of these molecules as well as library-selected molecules capable of specifically binding to selected targets and conjugates formed by attaching any of these molecules to a second molecule, or any derivative or variant thereof.

xii. Receptors

The analyte can be a receptor. The term "receptor" is a molecule capable of specifically binding to a ligand by affinity-based interactions. "Receptors" include, but are not limited to, biological, synthetic or engineered membrane receptors, hormone receptors, drug receptors, transmitter receptors, autacoid receptors, pheromone receptors, stimulus-response coupling or receptive molecules, antibodies, antibody fragments, engineered antibodies, antibody mimics or mimetics, molecular mimics, molecular imprints, molecular recognition units, adhesion molecules, agglutinins, lectins, selecting, cellular receptors, avidin and streptavidin, and congeners, analogs, competitors or derivatives of these molecules as well as nonoligonucleotide molecules selected, e.g., by combinatorial methods and/or library screening, to specifically bind other selected molecules and conjugates formed by attaching any of these molecules to a second molecule. Receptors further include selected molecules capable of specifically recognizing structural molecules, effector molecules and selectable molecules comprising ligands, or any derivative or variant thereof.

xiii. Signal-Generating Molecules

The analyte can be a signal generating molecule. "Signal-generating molecules" and "signal-generating species" are molecules capable of generating a detectable signal or enhancing or modulating the detectability of a substance or transducing an energy, activity, output or signal of a substance into a qualitatively, quantitatively or detectably different energy, activity, output, signal, state or form. Alternatively, signal-generating molecules can interact with the target molecule to produce an analyte capable of localization. Signal-generating molecules include, but are not limited to, molecules, groups of molecules, conjugates and complexes comprising detectable (and optionally dyed, modified, conjugated, labeled or derivatized) tags, tracers, radioisotopes, labels, reporters, polymers, light-harvesting complexes, antenna structures, natural and synthetic and biomimetic photosynthetic molecules, reaction centers, photosystems, signal transduction pathways, molecular cascades, macromolecules, microparticles, nanoparticles, colloids, metals, dyes, fluorophores, phosphors and other photon-absorbing, photon-emitting and photosensitive molecules, including molecules or groups that enhance, attenuate, modulate or quench the photon-absorbing or photon-emitting properties of another molecule or group, energy transfer donors and acceptors, enzymes, coenzymes, cofactors, catalytic antibodies, synthetic enzymes and catalysts, molecular mimics and mimetics, luminescent, triboluminescent, sonoluminescent, electroluminescent, chemiluminescent and bioluminescent molecules, electron transfer donors and acceptors, oxidizing and reducing compounds, mediators and other electroactive molecules, metabolic, photoactive, signaling and signal processing molecules used to capture and transduce energy in biological and biomimetic processes and systems, optionally including natural, synthetic or mimetic scaffold, organizational and coupling molecules, chaperones and accessory biological or biomimetic molecules or groups of molecules involved in the transduction of a first form of energy or information into a second form of energy or information.

xiv. Structural Molecules

The analyte can be any structural molecule. Examples include, but are not limited to, elements, atoms, molecules, ions, and compounds comprising surfaces, amphibious surfaces, inorganic and organic materials such as carbon, silicon, glass, organic and inorganic crystals, selected solvents, selected solutes, natural, biomimetic and synthetic nanostructures and microstructures, fibers, filaments, silks, molecular scaffolds, nanotubes, nanorods, fullerenes, buckyballs, diamondoid molecules, semiconductors, insulators, metals, plastics, elastomers, polymers, detergents, lubricants, waxes, oils, powders, fillers, excipients, fibers, tableting ingredients, packaging materials, papers, industrial plastics, cyclic and polycyclic molecules, dendrons, dendrimers, electrolytes and polyelectrolytes, salts, hydrocarbons, ceramics and biological, biocompatible, biomimetic, biodegradable and imprintable monomers, multimers and polymers, e.g., fatty acids, lipids, surfactants, amino acids, peptides, proteins, polyamines, polyacids, sugars, starches, cellulose, glycosylated molecules, glycopolymers and conjugates thereof.

xv. Ions

The analyte can be any ion. Examples of ions include alkali metal ions, alkali earth metal ions, transition metal ions, or lanthanide metal ions. In one aspect, a chelate can be added to a sample containing the ion to form an ion/chelate complex prior to localization. In this aspect, the ion, the chelate, and/or the ion/chelate complex is the analyte. In another aspect, a chelate can be covalently attached near the surface of the microporous material that can interact with the ion.

xvi. Nucleic Acid Analytes

In one aspect, the analyte is a nucleic acid. Nucleic acids such as deoxyribonucleic acid (DNA), ribonucleic acid (RNA), and peptide nucleic acid (PNA) are polymeric, polyionic molecules soluble in aqueous solution under certain conditions. The assumed three-dimensional structures of nucleic acids in solution as a function of pH, ionic strength, counter ions, charge neutralization, hydration, organic precipitants, molecular composition, etc., are known by those skilled in the art. In one aspect, the nucleic acid can be single or double stranded DNA or RNA.

There are a variety of molecules disclosed herein that are nucleic acid based, including for example the nucleic acids as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, the expressed mRNA will typically be made up of A, C, G, and U.

xvii. Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

Thus, nucleic acids are polymers made up of nucleotides, called bases generically. The nucleic acid molecules can be characterized by the number of bases that make up the nucleic acid. For example, in certain embodiments the nucleic acid analytes are at least 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 155, 160, 165, 170, 175, 180, 185, 190, 195, 200, 210, 220, 230, 240, 250, 260, 270, 280, 290, 295, 300, 320, 340, 360, 380, 400, 425, 450, 475, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3200, 3400, 3600, 3800, 4000, 4500, 5000, 5500, 6000, 6500, 7000, 7500, 8000, 8500, 9000, 9500, 10000, 11000, 12000, 13000, 14000, 15000, 16000, 17000, 18000, 19000, 20000, 25000, 50000, 100000, 200000, 300000, 400000, 500000, and 1000000 bases or base pairs long. In another aspect, the DNA or RNA has at least about 1,500 bases or base pairs.

The primary structure of nucleic acids is linear, with each base or base pair contributing approximately 0.34 nm to the fully extended contour length. Representative contour lengths of various nucleic acids are shown in Table 1.

TABLE 1

| Nucleic Acid | Bases or Base Pairs | Contour Length |
|---|---|---|
| Oligo Probe | 40 | .013 microns |
|  | 200 | .068 microns |
|  | 1,000 | .340 microns |
| HIV RNA | 9,000 | 3.06 microns |
| T4 Phage genome | 160,000 | 54.4 microns |
| E. Coli genome | 4.2 million | 1,428 microns |

The assumed diameter of nucleic acid molecules is about 2 nm, resulting in an exceptionally anisotropic, high aspect ratio primary structure. Higher order structures (secondary, tertiary, etc.) are well known for nucleic acids and are highly environment dependent. In aqueous solution, free of organic, ionic, or polymeric precipitants, nucleic acids are usually described as a coiled or relaxed three-dimensional configuration, but may be reversibly precipitated with known agents into a globular or condensed state. Likewise, coil form nucleic acids are known to undergo substantial three dimensional changes such as elongation, molecular orientation, etc. in flowing solutions.

In one aspect, the microporous materials, methods, and articles described herein can isolate nucleic acids from biological fluids for diagnostic purposes. High sensitivity assays require a 200 µl or larger patient sample to capture sufficient nucleic acid to be statistically meaningful. Commercially available viral load assays employ target or signal multiplication techniques (e.g., PCR, βDNA, etc.) based on target viral nucleic acid. That is, these techniques quantify total viral nucleic acid present in the sample fluid after virion lysis. A "virion" is a complete, mature virus particle. Unencapsulated viral nucleic acids present in the sample fluid before lysis are also included as part of the total load. Since unencapsulated viral nucleic acids are widely regarded as non-infectious, their inclusion into the viral load total represents an inaccuracy in the measurement.

Described herein are methods and materials that can be used to improve existing viral load assays by removing the majority of unencapsulated nucleic acids prior to analysis. In one example, the virion assayed is an HIV virion. The patient sample (e.g., plasma, serum, CSF, biological warfare extracts, etc.) is filtered through a microporous material described herein. The microporous material localizes all soluble nucleic acids (e.g., ssDNA, dsDNA, ssRNA, dsRNA) as well as cellular components larger than several microns in diameter. Intact virions pass through the filter, and the patient sample filtrate is then lysed to free the viral nucleic acids. The lysed patient sample filtrate is filtered then rinsed through a second microporous material to localize the virion-derived nucleic acids near the surface of the second microporous material.

3. Filters

Filtration can be considered a separation process based primarily on molecular dimension in relation to flow path dimension of the filter. Filters are generally classified as surface filters, where filtration primarily occurs on the entrance surface of the filter due to small, uniform pore dimensions of the microporous material, or depth filters, where the pores of the microporous material have a tortuous path structure and entrap particles within the depth of the filter.

Any of the microporous materials described herein, including the composites and modified-microporous materials, can be manufactured as a filter. In one aspect, the microporous material can be formulated into a filter such as, for example, a bead or membrane. Beads can be from several millimeters in diameter down to less than one micron diameter depending on system requirements. Beads can be spherical, irregularly shaped, or formed into any shape as required. The size of the beads can also vary depending upon their application. Beads can be uniformly porous, or display a microporous surface overlying a limited porosity core. Additionally, beads can be magnetic, paramagnetic, or have other properties that aid in bead separation.

Membranes are two dimensional structures with limited thickness. In one aspect, membrane filters have a thicknesses of from less than 1 micron to greater than 100 microns. In one aspect, the membrane has a thickness of 1 micron to 100 microns, 10 microns to 90 microns, 20 microns to 80 microns, 30 microns to 70 microns, or 40 microns to 60 microns. In another aspect, 0.2 micron Anopore™ inorganic oxide membranes are typically 40 to 50 microns thick, while 0.02 micron Anopore membranes have a very thin 0.02 micron porous layer less than 1 micron thick overlying a 0.2 micron support layer that is approximately 40 microns thick. Accordingly, membranes may be formed or created as an analyte localization surface on a support material. This support material confers useful characteristics to the system, such as strength, ease of handling, fluid flow properties, thermal properties, etc. In this aspect, the support material, and therefore the membrane, may be of varying shape, size, and design consistent with overall requirements.

In the methods described herein, surface filters or depth filters can be used for prefiltration of impurities and other debris from a sample before analyte separation and localization. To assist with improving filterability of test samples, other techniques known by those skilled in the art can be used in combination with any of the articles described herein. These include prefiltering test samples to remove large impurities, or treatment of test samples such as by sample digestion involving the use of enzymes, use of surfactants, use of chaotropic agents, ultrasonic and thermal treatments, protein precipitation, and the like.

4. Surfaces

Figure 1B:
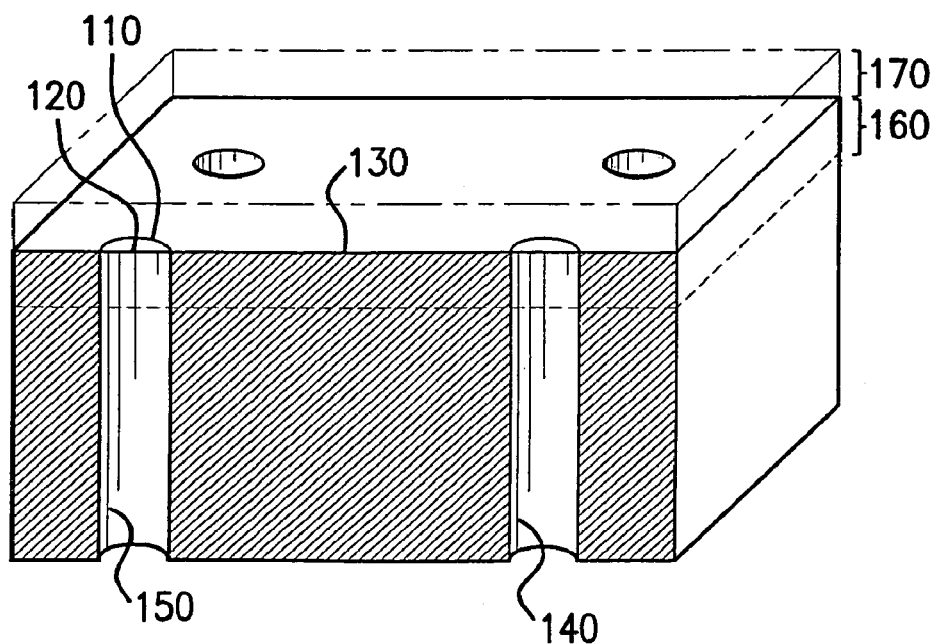
FIG. 1b shows the cross-sectional view of the microporous material.

The microporous material possesses many different surfaces. For example, there are planar surfaces, external surfaces, internal surfaces, and wetted surfaces. A schematic of a filter composed of a microporous material is depicted in FIGS. 1a and 1b. FIG. 1a is a top-view of the filter showing a microporous material 100, where 110 represents one of many holes or pores in the microporous material. These holes do not need to be uniformly spaced or sized, but in many embodiments they are. There are many different surfaces associated with the filter. FIG. 1b is a cross-sectional view of the filter with a microporous material. For example, there is a planar surface 120, which is the surface of the microporous material defined by the plane produced by the external surface of the microporous material 130 and the openings 110 caused by the plurality of pores and holes. An internal surface 140 is formed by the channel 150 that runs through the microporous material.

5. Analyte Interaction with Microporous Material i. Localized

When the analyte is contacted with any of the microporous materials described herein, the microporous material prevents or inhibits the analyte from passing into and through the material. The microporous material interacts with the analyte to substantially prevent molecular collapse of the analyte through the microporous material. In one aspect, surface filtration can be used to rapidly localize and concentrate the analyte. The efficiency of the surface filtration will depend upon numerous parameters such as analyte to pore size ratio, composition of impurities in the fluid to be filtered, and analyte-to-surface interactions.

In the aspect described above, when the sample containing the analyte comes into contact with the microporous material, the analyte is localized on the microporous material. The term "localized" as used herein is defined as an increase in the concentration of the analyte near the surface of the material. Thus there is reduction or inhibition of the analyte from flowing into and/or through the microporous material.

The localized analyte is near the surface of the microporous material and not trapped within the microporous material. Referring to FIG. 1b, the term "near the surface" as used herein is defined as (1) the region 10 microns below the planar surface of the microporous material, which is 160, (2) adjacent to the planar surface 120 of the microporous material, or (3) 25 µm above the planar surface, which is 170. In one aspect, the entire analyte or a portion of the analyte is at most 10 microns below the planar surface of the microporous material. In one aspect, when the analyte is adjacent to the planar surface, the analyte is in direct contact with the external surface of the microporous material. In one aspect, the analyte is below the planar surface by 10% relative to the pore depth, 8% relative to the pore depth, 6% relative to the pore depth, 4% relative to the pore depth, 3% relative to the pore depth, or 2% relative to the pore depth In one aspect, the analyte is from 10 µm, 5 µm, 4 µm, 3 µm, 2 µm, 1 µm, or 0.5 µm below the planar surface of the microporous material to 25 µm, 10 µm, 9 µm, 8 µm, 7 µm, 6 µm, 5 µm, 4 µm, 3 µm, 2 µm, or 1 µm above the planar surface, where any endpoint below the planar surface can be used with any point above the planar surface.

In one aspect, at least 10%, 20%, 30%, 40%, 50%, 60%, 70%, 80%, or 90% of the analyte is localized near the surface of the microporous material. In another aspect, the amount of analyte that is localized is at least 95%, at least 96%, at least 97%, at least 98%, at least 99%, at least 99.5%, or 100%. In one aspect, the target analytes are concentrated near the surface of the microporous material as discrete, isolated molecules. This aspect is useful for molecular counting, which is discussed below. In another aspect, the target molecules can be layered on top of each other near the surface of the microporous material. Localization of the analyte by mechanical filtration provides an extremely rapid, uncomplicated method of obtaining pure analytes for subsequent processing.

In addition, unlike prior techniques that require diffusion controlled reactions to retain the analyte for molecular counting, the microporous materials described herein use weak surface interaction to localize the analyte near the surface of the material. For example, when the analyte is a nucleic acid, reversible nucleic acid processing, as well as stronger surface interaction such as hybridization, covalent attachment, etc. for rapid nucleic acid localization to a filter surface are possible when using any of the microporous materials described herein. Although optional, a binding oligonucleotide that is complimentary to the nucleic acid that is to be localized does not need to be present on the microporous material in order to localize the nucleic acid. In another aspect, for ultra low concentration nucleic acid detection, such as found in ultra sensitive viral load assays, the microporous materials can be used with optical molecular counting techniques to directly determine nucleic acid concentrations without molecular amplification. This is possible because of the high concentration effect and exceptional detectability of nucleic acids localized near the surface of the microporous material.

As described above, separation of the nucleic acid is facilitated by weak nucleic acid-to-surface interactions near the surface of the microporous material. Although considered rigid on a molecular scale, nucleic acids are deformable on a micron size scale and, under certain conditions, can pass through practical filter pore diameters. Separation of nucleic acids by localization involves an interaction between the analyte and the microporous material in order to prevent the analyte from collapsing into the microporous material. In view of this, the size of the pores present in the microporous material is one variable to consider when selecting the microporous material. The pores should be small enough to efficiently exclude the analyte, but large enough to permit rapid passage of impurities remaining in the sample fluid. A schematic depiction of the technique is illustrated in FIG. 2.

Figure 2A:
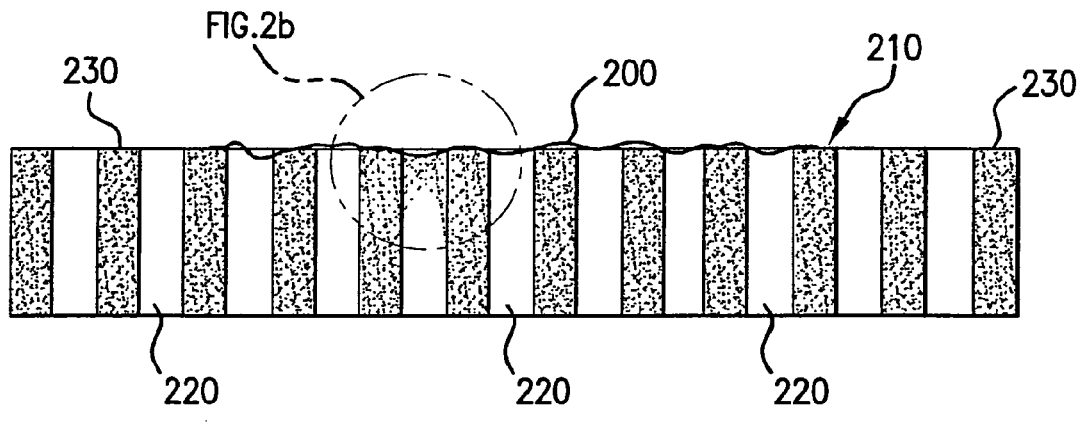
FIG. 2a shows the localization of an analyte near the surface of a microporous material.
Figure 2B:
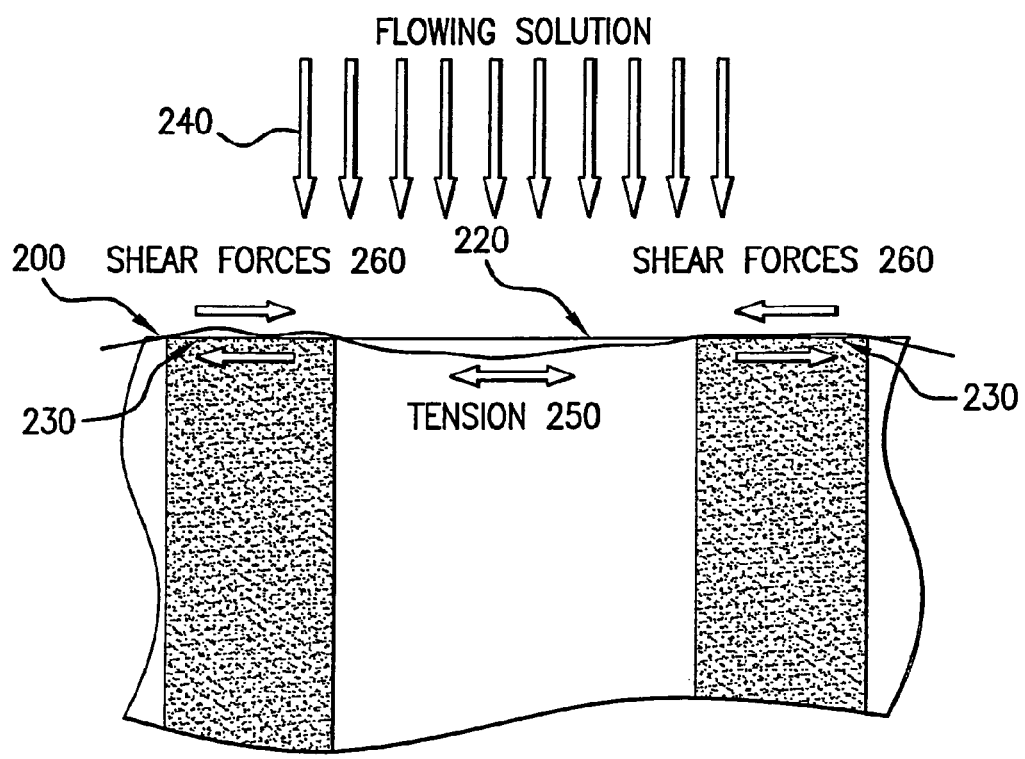
FIG. 2b shows the localization of an analyte near the surface of a microporous material.

As shown in FIGS. 2a and 2b, the analyte 200 has been localized near the surface of the microporous material 210, having a plurality of micropores 220 and flats 230, by mechanical filtration from a flowing solution 240. The length of the analyte 200 is large compared to the dimensions of micropores 220 and physically spans several openings as depicted in FIG. 2a.

As shown in FIG. 2b, surface interactions occur between localized analyte 200 and the exposed surface on flats 230. The interactions between polymers and surfaces have been widely studied and vary from essentially zero interaction to complete covalent immobilization. By analogy to purely mechanical systems, if solution 240 in FIG. 2b is flowing through the filter, analyte 200 is supported across micropores 220 by a molecular tension 250, which is supported by shear forces 260 developed between analyte 200 and flats 230. This is a consequence of the relatively large pore diameter preferred for practical filtration in conjunction with known molecular deformability. Even for large analytes spanning many pores, shear forces 260 are required to prevent the collapse of analyte 200 through micropores 220.

Unlike previously known analyte purification methodologies that rely on adsorption/precipitation within the pores of silica or other porous supports, when the analyte is a nucleic acid, the weak interactions required for nucleic acid localization is achievable with soluble, coil form nucleic acids under mild conditions. In one aspect, weak surface interaction for reversible nucleic acid processing is contemplated. In another aspect, stronger surface interactions such as hybridization, covalent attachment, etc. can be used for rapid nucleic acid localization.

ii. Immobilized

The term "localized" also includes the immobilization of an analyte near the surface of the microporous material. The term "immobilized" as used herein is defined as the restraint of the analyte at a specific region near the surface of the microporous material for a time long enough to be counted. In one aspect, the analyte is immobilized in a 1 $\mu m^3$ region during a specific detection period. The term "localized" also includes concentrating the analyte near the surface of the microporous material. The phrase "concentrating the analyte" as used herein is defined as the accumulation of the analyte near the surface of the microporous material at a fixed area regardless of the purity of the concentrated analyte. When the analyte is localized near the surface of the microporous material, the analyte may be reversibly or irreversibly bound to the microporous material. When the analyte is "reversibly" bound, the majority of the analyte can be removed from the microporous material. Conversely, when the analyte is "irreversibly" bound, the majority of the analyte cannot be removed from the microporous material.

6. Conditions for Localization

In one aspect, in order to assist with analyte localization, various inorganic salts can optionally be utilized in the sample solutions. For example, salts such as NaCl or chaotropic salts including guanidinium isothiocyanate, guanidinium hydrochloride, and the like, can also be utilized as desired in the sample solutions. In one aspect, the amount of salt used is less than 2 M, such as 1.8 M, 1.6 M, 1.4 M, 1.2 M, 1.0 M, 0.8 M, 0.6 M, 0.4 M, 0.2 M, 0.1 M, 0.05 M, where any concentration can form a range with another concentration (e.g., 0.1 M to 1.8M).

In another aspect, buffers can also be added to the sample containing the analyte, in order to facilitate localization. In one aspect, tris, carbonate/bicarbonate and the like can be used. In another aspect, phosphate buffers can be used to reverse the retention of the analyte on the microporous material and, thus, the analyte can be easily removed from the microporous material for subsequent analysis when desired. Phosphate ions are known to bind to aluminum oxide chromatography packing and can compete for the same weak binding sites on the microporous material. In one aspect, buffers can be used to control sample pH. In one aspect, pH values lower than about 4 result in high nucleic acid localization efficiency independent of buffering ions. In another aspect, pH values greater than 9 to 10 show decreasing localization efficiency even with amine modified microporous surfaces. In one aspect, the sample pH is maintained in the range of 6 to 8 to minimize protein precipitation. In this pH range, the ability of microporous material to efficiently localize nucleic acids depends on surface modification, salt concentration, and ion additives, such as buffer salts. In another aspect, an enzyme or surfactant can be present in the sample. As more fully discussed later, the effect of various buffers, salts, proteins, surfactants, etc. on localization depends on the nature of the interaction between the microporous surface and the analyte. For example, localization of nucleic acids onto plain, unmodified inorganic metal oxide microporous surfaces of 0.2 micron nominal pore size, for instance Anopore 0.2 micron membrane filters, shows increasing localization efficiency with salt concentration. As described herein, this salt effect does not depend on whether the salt is chaotropic. Additionally, this salt effect indicates only low concentrations of salt are required to produce efficient localization, generally under 1 molar and frequently under 100 millimolar. Amine modified Anopore 0.2 micron membrane filters show efficient localization independent of salt concentration.

Materials that coat microporous surfaces, for instance, proteins, surfactants, and the like, can affect localization by modification of the analyte-surface interaction. For example, proteins and surfactants generally lower localization efficiency for unmodified 0.2 micron Anopore membrane filters, but have little effect on amine modified filters. As previously mentioned, certain ions, for instance phosphate, borate, bicarbonate, etc. can affect nucleic acid localization on plain, unmodified 0.2 micron Anopore membrane filters presumably by competition with the analyte for weak binding sites on the microporous surface. In one aspect, Amine modified 0.2 micron Anopore membrane filters show greatly reduced ion effects.

7. Microporous Material

The term "microporous material" as used herein is any material having a plurality of pores, holes, and/or channels. The microporous material permits the flow of liquid through or into the material. The microporous material generally possesses a high concentration of small, uniform holes or pores of sub-micron dimensions. The microporous material can be optically transmissive to visible light, ultraviolet light, or infrared light, depending on the particular detection technique used to analyze the localized analyte. The microporous material can be hydrophilic to permit the rapid flow of water through the material. The microporous material can be optically opaque if desired. It is also desirable that the microporous material also possess good mechanical strength for easy handling, low non-specific binding, and relative inertness with the analyte. The term "microporous material" as used herein includes any of the composites and modified-microporous materials discussed below.

In one aspect, the micropores can have diameters ranging in size from about 0.02 microns to about 0.2 microns. For very large analytes, such as intact bacteria, cells, particulate, etc. larger pore sizes are contemplated. As previously discussed, larger pore sizes are less prone to plugging with impurities generally found in some samples. Pore sizes up to 10 microns can be contemplated for analysis of certain samples. In another aspect, the diameter of the pores is from about 0.02 microns to about 0.18 microns, about 0.02 microns to about 0.16 microns, about 0.02 microns to about 0.14 microns, about 0.02 microns to about 0.12 microns, about 0.02 microns to about 0.1 microns, about 0.04 microns to about 0.2 microns, about 0.06 microns to about 0.2 microns, about 0.08 microns to about 0.2 microns, or about 0.1 microns to about 0.2 microns.

The microporous material can be composed of any material that has a high concentration of small, uniform holes or pores or that can be converted to such a material. Examples of such materials include, but are not limited to, inorganic materials, polymers, and the like. In one aspect, the microporous material is a ceramic, a metal, carbon, glass, a metal oxide, or a combination thereof. In another aspect, the microporous material includes a track etch material, an inorganic electrochemically formed material, and the like. The phrase "inorganic electrochemically formed material" is defined herein as a material that is formed by the electroconversion of a metal to a metal oxide. The phrase "track etch material" is defined herein as a material that is formed with the use of ionizing radiation on a polymer membrane to produce holes in the material. Such materials are commercially available. Any of the microporous materials disclosed in U.S. Pat. No. 5,716,526, which is incorporated by reference in its entirety, can be used. In a further aspect, when the microporous material is a metal oxide, the metal oxide includes aluminum oxide, zirconium oxide, titanium oxide, a zeolite, or a combination thereof. Examples of zeolites include, but are not limited to, those disclosed in U.S. Pat. Nos. 4,304,675; 4,437,429; 4,793,833; and 6,284,232, which are incorporated by reference in their entireties. In one aspect, when the microporous material is a metal oxide, the metal oxide can contain one or more metal salts in varying amounts. For example, aluminum salts such as aluminum phosphate, aluminum chloride, or aluminum sulfate can be part of the microporous material.

In one aspect, the microporous material is an inorganic electroformed metal oxide, such as described in U.S. Pat. No. 6,225,131, the disclosure of which is incorporated by reference herein. Such ceramic membranes are available from Whatman, Inc. and distributed under the trade names Anopore™ and Anodisc™. Anopore membranes have a honeycomb type structure with each pore approximately 0.2 micron in diameter by 50 microns long. The Anopore membranes are composed of predominantly aluminum oxide with a small amount (5-10%) of aluminum phosphate. In this aspect, these microporous materials have the following desirable characteristics: substantially nonfluorescent in the visible spectrum; very uniform pore structure; high pore density and high liquid flow rates; relatively rigid; flat; and optically clear when wet; high melting point and easily heat welded to plastic; relatively biologically inert, and little non-specific binding or denaturing effects for proteins, nucleic acids, etc. In one aspect, the microporous material can be aluminum or titanium that has been anodized. Anodization is a technique known in the art that is used to produce an oxide layer on the surface of the aluminum or titanium.

In another aspect, the microporous material can be chemically modified to enhance surface localization of analytes. For example, since nucleic acids are negatively charged molecules, the microporous material can be treated to have a positive charge with various chemicals so that the nucleic acids stick near the surface of the microporous material through ionic attractive forces. Such weak attractive forces aid in keeping the nucleic acids from passing through the microporous material. In one aspect, the microporous material can be pretreated with silanization reagents including, but not limited to, aminopropyltrimethoxysilane (APS), ethylenediaminopropyltrimethoxysilane (EDAPS), or other amino silane reagents to impart a slight positive surface charge. In another aspect, the microporous material can be pretreated with polymer materials, including but not limited to polylysine, to impart a slight surface charge to enhance analyte localization. Additionally, the microporous material can be modified with neutral reagents such as a diol, an example of which is acid hydrolyzed glycidoxypropyltrimethoxysilane (GOPS), to vary analyte retention.

Any of the microporous materials described herein can be modified by techniques known to those skilled in the art. In one aspect, EDAPS modified microporous materials can be prepared by dissolving about 5% EDAPS into molecular grade water at room temperature. The aqueous solution is incubated for about 5 minutes at room temperature to hydrolyze the trimethoxy groups. This solution is filtered through the microporous material at a rate of approximately 1 milliliter per 1 $cm^2$ over a period of about 5 minutes. The activated microporous material is rinsed by filtering several equivalent volumes of molecular grade water through the microporous material, and is then dehydrated in a vacuum oven at approximately 40° C. The dry microporous material is then rinsed by filtering several equivalent volumes of 1×TE buffer solution (10 mM tris-HCl (tris(hydroxymethyl)aminomethane base), 1 mM EDTA (ethylenediaminetetraacetic acid) buffer, etc. pH 7-8) to adjust surface pH. The microporous material is then rinsed by filtering several equivalent volumes of molecular grade water and is then again dehydrated. The dry filter is stored dry at room temperature. In another aspect, diol modified membrane filters can be made similarly using GOPS instead of EDAPS and including a well known acid hydrolysis step to convert the adsorbed epoxide to a diol.

8. Composites

A few commercially available microporous materials possess low autofluorescence, such as, for example, Anopore inorganic oxide membranes. However, in some applications, even small amounts of autofluorescence are detrimental. For instance, fluorescence microscopy is a widely used powerful analytical tool for biological and morphological analysis. Weakly fluorescent specimens must be prepared on surfaces with exceptionally low autofluorescence such as specially processed fused silica, glass, or crystalline silicon. Fluorescent analysis of small particles (e.g., cells, virions, nucleic acids, etc.) directly on a filtration surface is typically limited by filtration membrane autofluorescence. Although inorganic oxide microporous materials exhibit much lower autofluorescence than polymeric membranes, the autofluorescence may be too high for analysis of weakly fluorescing particles.

As described above, Anopore membranes have a honeycomb type structure, with each pore approximately 0.2 micron in diameter by 50 microns long. The internal area of the microporous material is much greater than the external surface area. Indeed, it is generally accepted the internal wetted area of Anopore membranes is typically 500 times greater than the projected surface area. In some cases, this large internal surface area is detrimental to optical analysis of particles present on the external surface. For instance, biological cells are frequently analyzed by fluorescently tagged specific protein binding reactions. In theory, a system can be developed that localizes unknown cells near the surface of the microporous material followed by exposing the localized cells to fluorescently labeled proteins. After rinsing unbound proteins from the microporous material, specific binding reactions between the localized cells and the labeled proteins are detected by increase in fluorescence in the localized cells. Unfortunately, all surfaces exhibit what is known as nonspecific binding (NSB). That is to say, a small amount of labeled protein will bind to the microporous material in the absence of a specific receptor on a cell. Most optical detectors are unable to differentiate specific signals originating from the specifically labeled surface localized cells from that originating within the transparent microporous material from fluorescent proteins nonspecifically bound to the large internal membrane surface area. Although the microporous materials described above are capable of effectively concentrating and localizing particulate samples to their surface for analysis, NSB to the large internal surface area of the microporous material frequently limits useful sensitivity.

In order to address these concerns, described herein are composites composed of microporous materials that have been modified to alter the optical properties of the microporous material (e.g., autofluorescence, internal optical scatter, and fluorescent NSB detection). In one aspect, the microporous material is modified to render the microporous material optically opaque so as to reduce detectable fluorescence and scatter originating within the material, either from the material itself (autofluorescence) or from internally bound tracers or contaminants (NSB).

i. Pigment Containing Composites

The term "composite" as used herein is a product composed of two or more materials. Depending upon the selection of the materials, the materials may or may not react with one another to produce the composite. In one aspect, the composite is composed of a microporous material and a pigment. The term "pigment" as used herein is any compound that modifies the optical properties of the microporous material. The term "pigment" also includes precursor compounds that upon chemical manipulation can be converted to the pigment. For example, $PdCl_2$ may not be able to modify optical properties; however, when it is reduced to palladium metal, it is material than can modify optical properties of a microporous material. The pigment is incorporated in the microporous material. The phrase "incorporated in the microporous material" as used herein is defined as any method for attaching a pigment to the microporous material. The attachment of the pigment to the microporous material can be via a covalent bond, an ionic interaction, entrapment of the pigment by the pores of the microporous material, or by depositing the pigment near the surface of the microporous material and/or on the internal surface of the microporous material. The pigment can be incorporated on any wettable surface of the microporous material. Any of the composites described herein can be used in any of the articles, methods, or kits described herein.

The composite is formed by incorporating a pigment in the microporous material. In one aspect, the pigment is covalently attached to the microporous material. The phrase "covalently attached to the microporous material" is defined herein as forming a chemical bond directly between the pigment and the microporous material in the absence of a linker. For example, a moiety on the surface of the microporous material can react with a moiety present on the pigment to form a covalent bond. The pigment can be covalently attached to any wettable surface of the microporous material (i.e., internal and external surfaces). Examples of moieties bound to the microporous material that can react with the pigment include, but are not limited to, a hydroxyl group, a carboxyl group, a sulfhydryl group, an amine group, or a combination thereof.

Alternatively, the phrase "covalently attached" also includes attaching the pigment to the surface of the microporous material with the use of a linker. For example, a linker can be any compound having a moiety that is capable of forming a bond with a moiety on the surface of the microporous material as well as a moiety that is capable of forming a covalent bond with the pigment. The moiety on the linker can be the same or different depending upon the microporous material and pigment selected. In one aspect, the linker is an organosilyl group. Silanation has been previously described and is a well-understood chemical method of modifying the surface of materials and can be additionally used to create a reactive surface on which to attach various organic molecules. For example, amine terminated reactive silanation reagents such as aminopropyl trimethoxysilane (APS) and ethylenediaminopropyl trimethoxysilane (EDAPS) can be used to create a surface capable of covalent reaction with protein linkers, reactive dyes, etc. Additionally, epoxy terminated reactive silanation reagents such as glycidoxypropyl trimethoxysilane (GOPS) can be used to create a surface capable of directly reacting with nucleophiles in dyes, proteins, or other reagents. In one aspect, the microporous material can be modified by those skilled in the art with other silanation reagents to impart various useful surface functionalities, such as carboxylate, sulfhydryl, hydroxy, aromatic, hydrophobic. Any of the silane compounds disclosed in U.S. Pat. No. 5,959,014, which is incorporated by reference in its entirety, can be used in this aspect.

In one aspect, a pigment in the form of an organic dye is covalently attached to the wettable surface of the microporous material. The term "organic dye" as used herein is defined as any organic compound that can modify the optical properties of the microporous material when the compound is incorporated in the microporous material. Dye attachment to silane modified microporous material is straightforward and depends on the specific attachment chemistry chosen. For instance, amino modified microporous material (e.g., APS or EDAPS) can react with several chemical families of known amino reactive dyes including, but not limited to, isothiocyanates, triazines, and active esters. Any of the organic dyes disclosed in U.S. Pat. Nos. 6,630,018; 6,623, 908; 5,985,514; and 5,294,870, which are incorporated by reference in their entireties, can be used to produce the composites described herein.

In another aspect, the organic dye can stain the microporous material without forming a covalent bond with the microporous material. For example, the organic dye can be entrapped in the pores of the microporous material. Additionally, the organic dye can be attached to a surface bound polymer such as, for instance, polylysine.

The organic dye that is selected depends on the final desired properties of the membrane. For example, triazinyl dyes are widely used as permanent fiber reactive dyes for cloth, paper, etc. as well as analytical labeling. They are available both as fluorescent and non-fluorescent dyes. Dichlorotriazinylaminofluorescein (DTAF) can react with amine modified microporous materials to produce an intensely fluorescent yellow material. Low fluorescent triazinyl dyes, such as Reactive Blue 4 or selections from the Procion MX series of organic dyes can be used to impart reduced autofluorescence, NSB fluorescence, and microporous material scatter.

In one aspect, the composite includes a microporous material composed of aluminum oxide and the pigment is an organic dye, wherein the organic dye is covalently attached to the aluminum oxide by an organosilyl group. In another aspect, the microporous material is Anopore.

In another aspect, the pigment is deposited on the microporous material. The term "deposited on the microporous material" is defined herein as any method for precipitating the pigment on any wettable surface of the microporous material. In one aspect, the resultant precipitate or deposit can be composed of ionic compounds, non-ionic compounds, elemental compounds, or a combination thereof. In one aspect, the pigment is an elemental metal such as a transition metal, a metal oxide, a metal alloy, or a combination thereof. Examples of transition metals include palladium, nickel, silver, gold, or a combination thereof. In the case when the pigment is a transition metal, the metal can be zero-valent or any other valency depending upon the particular transition metal compound selected. In another aspect, carbon black inclusions can be deposited in the pores of the microporous material.

In one aspect, the pigment can be deposited on the microporous material by an electroless metallization process. Electroless metallization processes are known to those skilled in the art for depositing metal alloys within high aspect ratio nanometer scale pore type structures. Electroless metallization processes on non-conductors frequently require a surface catalyst for initiation. In one aspect, palladium metal can be used in several forms, including colloid suspensions, ionic liquids, and metal ions that may be chemically reduced on the surface of the microporous material to form metallic nanoscale clusters. These palladium nanoparticles can form growth sites for electroless metallization.

It is desirable to alter the optical properties of the microporous material without effecting filtration efficiency. Many metallization processes initially form black deposits (palladium black, black nickel, silver, etc.) This may be due to the very rough (nanoscale) discontinuous nature of the first metallization deposits forming as discrete "islands" on the surface, together with surface reactions that may involve oxidation, etc. Those skilled in the art of electroless metallization are able to choose reaction conditions, reagents, etc. to maximize formation of black pigmentary deposits within the pores of the microporous material. These deposits are found to be non-fluorescent and have minimal effect on membrane flow rate.

In one aspect, the composite includes a microporous material composed of aluminum oxide and a pigment composed one or more elemental transition metals, wherein the pigment is deposited on the microporous material. In one aspect, the microporous material is Anopore. In another aspect, the elemental transition metal is palladium, nickel, or a combination thereof with other elements such as phosphorous, boron, or a combination thereof.

Additionally, it is widely known certain nanoscale metal particles undergo a process known as Plasmon resonance. In one aspect, this process generally occurs with gold and silver particles in the size range of 10 to 200 nanometer dimension. Collections of such particles, when correctly spaced on a surface, may form what may be described as a Plasmon resonance surface. These surfaces can exhibit unique optical properties such as enhanced absorption, fluorescence, energy transfer, etc. For instance, it is known Raman scattering of certain molecules can be enhanced many orders of magnitude in conjunction with Plasmon resonance. Additionally, collections of Plasmon resonance particles, when correctly spaced within a volume, can form what may be described as a Plasmon resonance volume, with unique optical properties. If the Plasmon resonance volume is porous, molecular interactions can occur within the large internal Plasmon resonance surface, greatly facilitating reaction rates. For example, as disclosed herein nanoscale metal deposits can be formed within the pores of microporous materials. Under controlled conditions, these deposits can be formed from gold or silver in a size range and surface density consistent with forming a Plasmon resonance surface. If the microporous material is selected with suitable pore dimensions and spacing, Plasmon resonance can occur between adjacent pores and result in a Plasmon resonance volume.

In one aspect, described herein are methods for producing a pigmented composite. A pigmented composite is any microporous material that has at least one pigment described herein incorporated in the microporous material. In one aspect, the method involves (a) contacting a microporous material with a tin compound to produce a first composite, and (b) contacting the first composite with a pigment comprising an elemental metal, a metal oxide, a metal alloy, a metal salt, or a combination thereof to produce the pigmented composite.

Any of the microporous materials and pigments described herein can be used in this aspect.

The tin compound used in this aspect can be any tin compound known in the art. In one aspect, the tin compound can be an organotin compound or a tin salt. In another aspect, the tin compound can be a compound that produces $Sn^{+2}$ ions in solution. Examples of tin compounds useful herein include, but are not limited to, tin halides such as $SnCl_2$. Not wishing to be bound by theory, it is believed that the tin compound enhances the adsorption of the pigment onto the microporous material. Additionally, depending upon the pigment selected, the tin compound can react with the pigment. For example, the tin compound can reduce or oxidize a pigment. One advantage of using the tin compound is that it permits the composite to be rinsed or washed to remove unadsorbed pigment, which ultimately results in a cleaner, more efficient pigmented composite.

The tin compound and pigment can be applied to the microporous materials using techniques known in the art including, but not limited dipping, spraying, brushing, etc. In one aspect, independent solutions of the tin compound and pigment are produced, and the microporous material is dipped in the tin solution followed by dipping in the pigment solution. Depending upon the tin compound and pigment that are selected, the tin compound and pigment can be dissolved in water, an organic solvent, or a combination thereof. In one aspect, the tin compound and pigment are dissolved in an organic solvent and optionally diluted with water. In another aspect, two or more pigments can be applied to the microporous material after contacting the microporous material with the tin compound. In one aspect, after the microporous material is contacted with the tin compound, the microporous material is contacted with a first pigment followed by contacting the first composite with a second pigment. In an alternate aspect, the microporous material can be contacted with a mixture of two or more pigments. The amount of tin compound and pigment that is used as well as the contacting conditions will vary depending upon the selection of the tin compound and pigment.

In another aspect, when the microporous material is contacted with a solution of the tin compound and/or pigment, the microporous material can be rinsed with water to remove any unadsorbed tin compound and pigment. After the microporous material is contacted with the final pigment, the pigmented composite can be heated so that the pigment is sealed in the microporous material. Not wishing to be bound by theory, it is believed that the heating step shrinks or reduces the size of the pores of the microporous material, which traps or engulfs the pigment. In one aspect, the sealing step can be performed by boiling the pigmented composite in water.

In one aspect, a microporous material such as aluminum oxide is contacted first with a tin compound such as a tin salt, followed by a palladium compound, and then a nickel compound to produce a pigmented composite. In another aspect, a pigmented composite is composed of a microporous material, a tin compound, and at least one pigment, wherein the tin compound and pigment are incorporated in the microporous material.

C. Manipulation of Localized Analytes

Once the analyte is localized on the microporous material, it can be further processed using techniques known in the art. The following techniques are exemplary and are not intended to limit the different type of techniques that can be performed.

1. Amplification

In one aspect, when the analyte is a nucleic acid, the localized nucleic acid can be analyzed using amplification techniques including, but not limited to, polymerase chain reaction, nucleic acid sequence based amplification, isothermal methodology, ligase chain reaction, and strand displacement amplification. Any of the amplification techniques disclosed in U.S. Pat. Nos. 4,683,195; 4,683,202; 4,965,188; 5,130,238; 5,354,668; 5,427,930; and 5,455,166, which are incorporated by reference in their entireties, can be used in any of the methods described herein. Depending upon the amplification technique used, a specific region of the nucleic acid or the entire nucleic acid can be amplified. In one aspect, when the analyte is irreversibly localized near the surface of the microporous material, amplification occurs near the surface of the microporous material. In another aspect, when the analyte is reversibly localized near the surface of the microporous material, amplification can occur near the surface of the microporous material and/or in solution where the analyte is no longer localized near the surface of the microporous material. In another aspect, localized analytes can be amplified or detected after destabilization of the weak interactions that exist between the analyte and the microporous surface by conditions herein described.

In one aspect, a nucleic acid is amplified by (a) amplifying a nucleic in a fluid sample having a known volume to produce an amplified nucleic acid, and (b) passing the sample comprising the amplified nucleic acid through any of the microporous materials described herein, wherein the amplified nucleic acid is localized near the surface of the composite. In another aspect, a nucleic acid is amplified by (a) passing a fluid sample having a known volume comprising the nucleic acid through any of the microporous materials described herein, wherein the nucleic acid is localized near the surface of the composite, and (b) amplifying the nucleic acid.

2. Hybridization and Identification

The following discusses the different type of compounds that can be used in the hybridization/identification methods disclosed herein.

i. Sequences

There are a variety of sequences that can be used with the hybridization/identification methods disclosed herein, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those sequences available at the time of filing this application at Genbank are herein incorporated by reference in their entireties as well as for individual subsequences contained therein. Genbank can be accessed at http://www.ncbi.nih.gov/entrez/query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

a. Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of any of the disclosed nucleic acids. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

ii. Antibodies a. Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof. The antibodies can be tested for their desired activity using the in vitro assays described herein, or by analogous methods, after which their in vivo therapeutic and/or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA,* 81:6851-6855 (1984)).

The disclosed monoclonal antibodies can be made using any procedure which produces monoclonal antibodies. For example, disclosed monoclonal antibodies can be prepared using hybridoma methods, such as those described by Kohler and Milstein, *Nature,* 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the HIV Env-CD4-co-receptor complexes described herein.

The monoclonal antibodies may also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

b. Human Antibodies

The disclosed human antibodies can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.,* 147(1):86-95, 1991). Human antibodies (and fragments thereof) can also be produced using phage display libraries (Hoogenboom et al., *J. Mol. Biol.,* 227:381, 1991; Marks et al., *J. Mol. Biol.,* 222:581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA,* 90:2551-255 (1993); Jakobovits et al., *Nature,* 362:255-258 (1993); Bruggermann et al., *Year in Immunol.,* 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

c. Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature,* 321:522-525 (1986), Reichmann et al., *Nature,* 332:323-327 (1988), and Presta, *Curr. Opin. Struct. Biol.,* 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

In one aspect, when the analyte is a nucleic acid, the localized nucleic acid can be hybridized and identified. For example, if a sample containing a nucleic acid with an unknown or partly unknown sequence is localized near the surface of the microporous material or composite and is brought into contact with a binding oligonucleotide that is complimentary to the nucleic acid, hybridization will occur. The binding oligonucleotide can be any naturally-occurring oligonucleotide or a modified oligonucleotide such as, for example, PNA. Based on the hybridization pattern, it is possible to derive sequence information from the localized nucleic acid. Thus, some or all of the nucleic acid sequence can be identified. These hybridization techniques are disclosed in Fodor et al. (1992), *Science* 251, 767-773 and Southern et al. (1994) *Nucleic Acids Res.* 22, 1368-1373, which are incorporated by reference in their entireties.

In one aspect, a nucleic acid is hybridized and/or identified by (a) hybridizing a nucleic acid in a fluid sample with a binding oligonucleotide having a known sequence that is complimentary to the nucleic acid to produce a hybridized nucleic acid and (b) passing a fluid sample comprising the hybridized nucleic acid through any of the microporous materials described herein, wherein the hybridized nucleic acid is localized near the surface of the composite. In another aspect, a nucleic acid is hybridized by (a) passing a fluid sample comprising the nucleic acid through any of the microporous materials described herein, wherein the nucleic acid is localized near the surface of the composite, and (b) hybridizing the nucleic acid with a binding oligonucleotide that is complimentary to the nucleic acid.

3. Bioreactors

In one aspect, any of the microporous materials described herein including the composites and modified-microporous materials can be used as a bioreactor. In this aspect, the bioreactor can be used for small-size fermentations, biochemical flow analyzers, or a part of a biosensor. In one aspect, a bioactive agent can be covalently attached to the microporous material either directly or by a linker as described above. For example, an enzyme can be attached to the microporous material via silanation described above, which produces an enzyme/support system. In another aspect, the bioactive agent can be attached to the microporous material by way of a suspension matrix to improve reaction rates. In one aspect, the enzyme/support system can behave as a catalyst and produce new compounds when a solution of reactants are contacted with the enzyme/support system. In another aspect, the enzyme/support system can behave as a biosensor and interact with specific analytes present in a sample.

4. Quantification

In one aspect, the localized analyte can be used to quantify the amount of analyte that was in the fluid sample. The phrase "quantifying an analyte" is defined herein as calculating the amount of analyte present in a known volume of sample once the analyte has been localized near the surface of the microporous material. In one aspect, the analyte is quantified by detecting and counting the analyte particles and correlating the number of analyte particles to a corresponding concentration based on the known volume of the sample.

The methods described herein for quantifying analytes permit the rapid analysis of the analyte. In one aspect, the analysis of the analyte can be performed in less than 30 minutes. In another aspect, the analysis of the analytes do not require target molecular amplification or multiplication (e.g., polymerase chain reaction (PCR)) for high sensitivity, which provides improved precision and accuracy. Numerous other advantages are described below.

i. Labeling of Analyte

Depending upon the detection technique used, in one aspect, the analyte can be labeled prior to detection. The term "labeled analyte" as used herein is defined as an analyte that has interacted with a detectable tracer. The interaction between the analyte and the detectable tracer can include any chemical or physical interaction including, but not limited to, a covalent bond, an ionic interaction, or a Lewis acid-Lewis base interaction. A "detectable tracer" as referred to herein is defined as any compound that (1) has at least one group that can interact with the analyte as described above and (2) has at least one group that is capable of detection using techniques known in the art. In one aspect, the analytes can be labeled prior to localization. In another aspect, the analyte can be labeled after it has been localized.

When the analyte is a nucleic acid, techniques for modifying nucleic acids to allow binding and labeling through specific hybridization are well known in the art. For example, target nucleic acids may be localized to a surface specifically or nonspecifically. The phrase "specifically localized target nucleic acid" is defined herein as target nucleic acids present in a sample that are specifically localized near the surface of the microporous material, for instance by specific binding reactions that only capture and localize the specific target nucleic acid. Any target nucleic acids not specifically localized are referred to herein as "non-specifically localized target nucleic acids." Labeling for pure, specifically localized target nucleic acids, where only target nucleic acids are localized, may be accomplished by using commercially available molecular labels, such as fluorescent nucleic acid dyes. In one aspect, the localization of specifically localized target nucleic acids can be accomplished by employing a localized specific binder, such as a complimentary binding oligonucleotide, to specifically capture and localize a target nucleic acid to near the surface of the microporous material. In this aspect, all nucleic acids localized near the surface of the microporous material are target molecules and can be labeled and counted.

In another aspect, non-specifically localized target nucleic acid localization involves localizing most nucleic acids contained within the patient sample near the surface of the microporous material. In this aspect, labeling non-specifically localized target nucleic acids, where target and other nucleic acids are co-localized to the surface, may be accomplished either by using a detectable tracer such as a specific binding probe labeled with detectable markers, or by forming surface localized hybrids between the localized target nucleic acids and specific binding probes with subsequent labeling such as with fluorescent nucleic acid dyes. In this aspect, target molecules can be specifically labeled and counted in the presence of potentially high concentrations of unwanted nucleic acids.

In one aspect, localized virion-derived nucleic acids can be fluorescently stained with non-specific nucleic acid dyes. Alternatively, the nucleic acid dye may be added to the lysed patient sample filtrate prior to the localization step. The localized fluorescent nucleic acids can then be counted using the techniques described herein. This approach provides an improved technique to identify potentially infectious particles.

In one aspect, the detectable tracer is two or more different detectable tracer molecules. Examples of detectable groups present on the detectable tracer include, but are not limited to, a fluorescent microbead, a quantum dot, a surface plasmon resonance particle, a fluorescence generating enzyme, a fluorescent dye, or a combination thereof. In one aspect, the detectable tracer is a labeled or non-labeled oligonucleotide probe. In another aspect, the following detectable tracers can be used to label nucleic acids.

a. Fluorescent Tracers

Fluorescent nucleic acid staining can be used for labeling target nucleic acid molecules. Fluorescent nucleic acid dyes selectively stain nucleic acids through intercalation, minor groove binding, etc. The most useful of these dyes exhibit a strong fluorescence enhancement on binding to nucleic acids. Non-limiting examples of such dyes include ethidium bromide, propidium iodide, Sybergreen I, Toto-3, Sytox Orange, and the like. Some of these dyes have high quantum yields (greater than about 50%) and fluorescence enhancements of greater than 1000 upon binding to certain types of nucleic acids. This fluorescence enhancement upon binding to nucleic acid minimizes the signal-to-noise limitations of fluorescent tracers, and dye nonspecific binding is essentially nonfluorescent. Additionally, dye loading per target nucleic acid can be high, often approaching 1 fluorescent dye molecule per 4 base pairs. Limitations of fluorescent nucleic acid dyes include staining of all nucleic acids on the target surface, although frequently with a preference for double strand DNA, RNA, etc.

Additionally, a sequential fluorescent staining approach may be used. Such an approach is especially useful in cases where although target nucleic acids are specifically localized near the surface of the microporous material with complimentary oligonucleotides, it is unlikely that all nucleic acids on the surface will be target nucleic acids to the level of purity required for biological assay. In this case, target and non-target nucleic acids are co-localized. In the sequential staining approach, a first nucleic acid dye A is added that preferentially stains the double stranded segments of all localized nucleic acids with very high affinity. Free dye A is then removed from the system, and a complimentary oligonucleotide probe (unlabeled) is added and binds to the target nucleic acid. A second nucleic acid dye B is then added and binds to the newly created oligo probe-target nucleic acid hybrid regions. This results in the true target nucleic acid being labeled with dye B while dye A blocks all nonspecific nucleic acid dye binding sites.

DNA, RNA, and PNA (peptide nucleic acid) oligonucleotide based probes can be used to label target nucleic acids either before or after localization through specific hybridization. The phrase "surface localized hybrid" is defined herein as the product formed when a nucleic acid localized near the surface of the microporous material is brought into contact with a substrate (e.g., DNA or RNA) having a known sequence so that the substrate interacts with the localized nucleic acid. Alternatively, the phrase "surface localized hybrid" is defined herein as the product formed when a nucleic acid is brought into contact with a substrate (e.g., DNA or RNA) having a known sequence so that the substrate interacts with the nucleic acid to produce a hybrid and then localizing the hybrid. Many such systems are known to those skilled in the art. These hybridization probes can be used to form detectable tracers by direct labeling with materials to make them optically detectable. Examples of probes include, but are not limited to, dyes, beads, proteins and protein aggregates, quantum dots, nanocrystals, and the like. Additionally, the nucleic acid can be labeled with materials to make them optically detectable after additional steps. For instance, biotinylated probes are widely used in molecular diagnostics. After hybridization, the bound biotinylated probes are reacted with optically detectable materials containing specific binders for biotin, for instance avidin, streptavidin, neutravidin, etc. The hybridization probes may additionally be directly or indirectly labeled with enzymes that are able to create optical signals after additional steps as will be described later.

In one aspect, viral load assays can be labeled. HIV contains single strand ribonucleic acid (RNA) approximately 9,000 bases in length. There are 360 separate 25 base length oligonucleotide probes that can be generated against the complete HIV RNA molecule. The ability to synthesize numerous, different oligonucleotide probes for specific binding to HIV RNA, as well as other target nucleic acids, is well known by those skilled in the art. Likewise, the ability to make these specific oligo probes fluorescent through incorporation or attachment of dyes, fluorescent beads, fluorescence generating enzymes, etc. is also well known.

The choice of fluorescent label for attachment to oligonucleotide probes to produce a detectable tracer is largely determined by detector parameters. Example 14 sets forth present detection data calculations based on detecting 25 or 100 highly fluorescent molecules (e.g., fluorescein, rhodamine, Cy 5, etc) per target nucleic acid with a low power scanning detection system such as a scanning confocal epifluorometer. In one aspect, a process for producing such labeled molecules is as follows. Localized target nucleic acids are incubated with probe solution to allow hybridization to occur. In the case of porous membrane localization, flowing probe solution through the membrane during hybridization can shorten reaction times. Unhybridized probe solution is rinsed from the optical detection surface under conditions to control hybridization stringency, NSB, etc.

Figure 3:
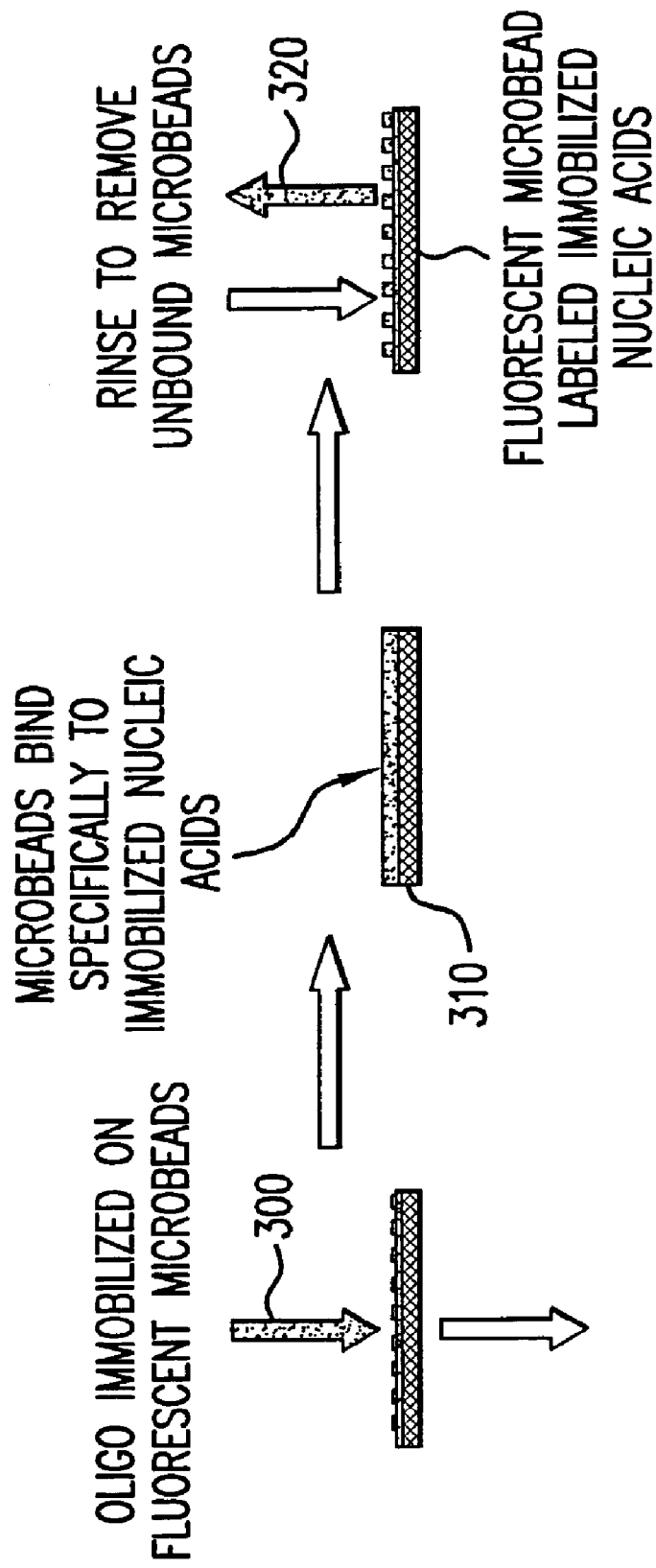
FIG. 3 shows a fluorescent bead based tracer process for a localized analyte.

A fluorescent bead based tracer process is depicted schematically in FIG. 3. Initially, fluorescent particles such as fluorescent microbeads 300 are coated with specific binding oligonucleotide probes which are localized on the microbeads. The fluorescent microbeads 300 are sized for retention on the surface of a membrane filter 310. After the target nucleic acids have been localized near the surface of membrane filter 310, the fluorescent microbeads are introduced and filtered onto the surface of membrane filter 310. The fluorescent microbeads, coated with binding oligonucleotides, are thus placed in direct contact with the localized target nucleic acids, and hybridization reactions rapidly occur unimpeded by diffusion. After a suitable incubation period, unbound microbeads 320 are rinsed off under conditions that control hybridization stringency and binding specificity. Multiple beads should be attached to each target nucleic acid to discriminate against tracer bead nonspecific binding.

b. Enzyme Tracers

In another embodiment, enzymatic techniques can be used as a detectable tracer to label analytes with high SNR. The principle of enhanced activity of "suspended" reactants can be used. For example, antibodies and other proteins, as well as other molecules, are known to lose activity when retained to a surface. Retention of analytes to a "scaffolding" matrix, for instance of macromolecules localized to a microporous material can greatly improve activity by minimizing surface inactivation and improving mass transfer by allowing flow through the active microporous material.

Fluorescent precipitation assays have been described in the art and use an enzyme tracer that converts a soluble, non-fluorescent substrate to a fluorescent precipitate localized at the point of enzymatic activity. Examples of enzyme tracers used in precipitation assays include, but are not limited to, alkaline phosphatase as used in Enzyme Labeled Fluorescence (ELF), which is available from Molecular Probes, Inc. In this case, localized target nucleic acids are hybridized to oligonucleotide probes labeled with suitable enzymes that subsequently create localized fluorescent microprecipitates that can be counted in one-to-one correspondence to the target nucleic acids.

Figure 4:
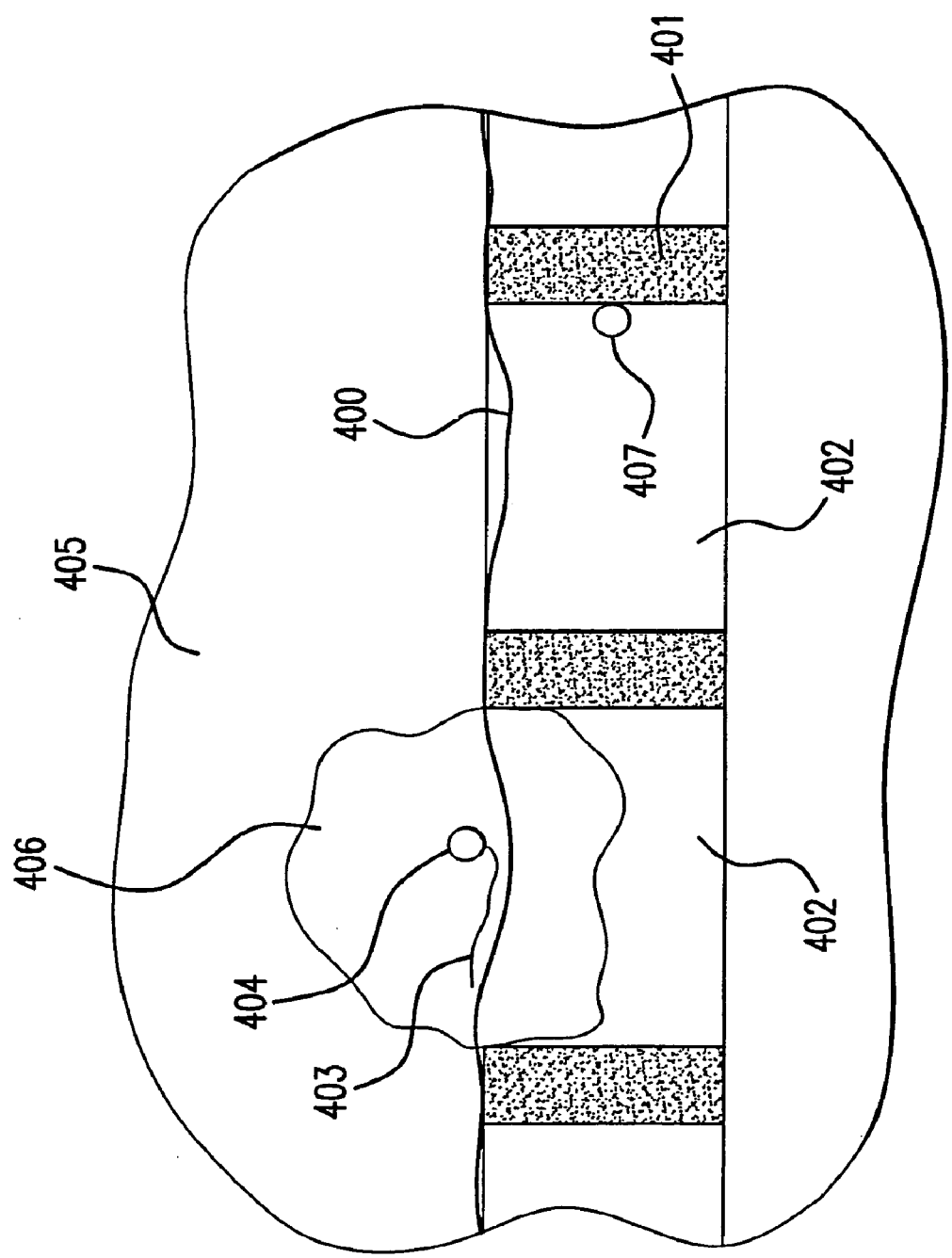
FIG. 4 shows the use of enzyme linked fluorescence for the detection of a localized analyte.

FIG. 4 shows an ELF reaction used herein. Target nucleic acid 400 is localized near the surface of microporous material 401 and physically spans several openings 402. Biotinylated hybridization probe 403 has been specifically hybridized to target nucleic acid 400. Note the figure is not to scale, as the typical 25 base nucleotide probe is only about 8 nanometers long, compared to the nominal pore diameter of approximately 180 nanometers. Alkaline phosphatase-streptavidin conjugate 404 has been bound to biotinylated probe 403. Unbound probes and unbound conjugates have been rinsed from the system. Nonfluorescent, soluble ELF substrate 405 has been added and conjugate 404 is generating fluorescent precipitate 406 on and within filter 401. In this case, conjugate 404 bound to hybridized probe 403 is typically "suspended" over a pore of the surface. This typically results in high enzymatic activity due to minimal surface denaturation and excellent multidirectional substrate diffusion. Nonspecifically bound conjugate 407 present on the membrane surface is typically much less active due to surface denaturation of the conjugate as well as relatively inhibited substrate diffusion to the surface. Additionally, the ELF fluorescent precipitate 406 is generated near the surface of the microporous material. This enhances nanocrystal precipitation, localizes the nanocrystal near the surface, and somewhat limits nanocrystal growth to typical pore dimensions. All these contribute to improved detectability. As previously discussed, multiple tracer binding may additionally be used to improve SNR.

Figure 5:
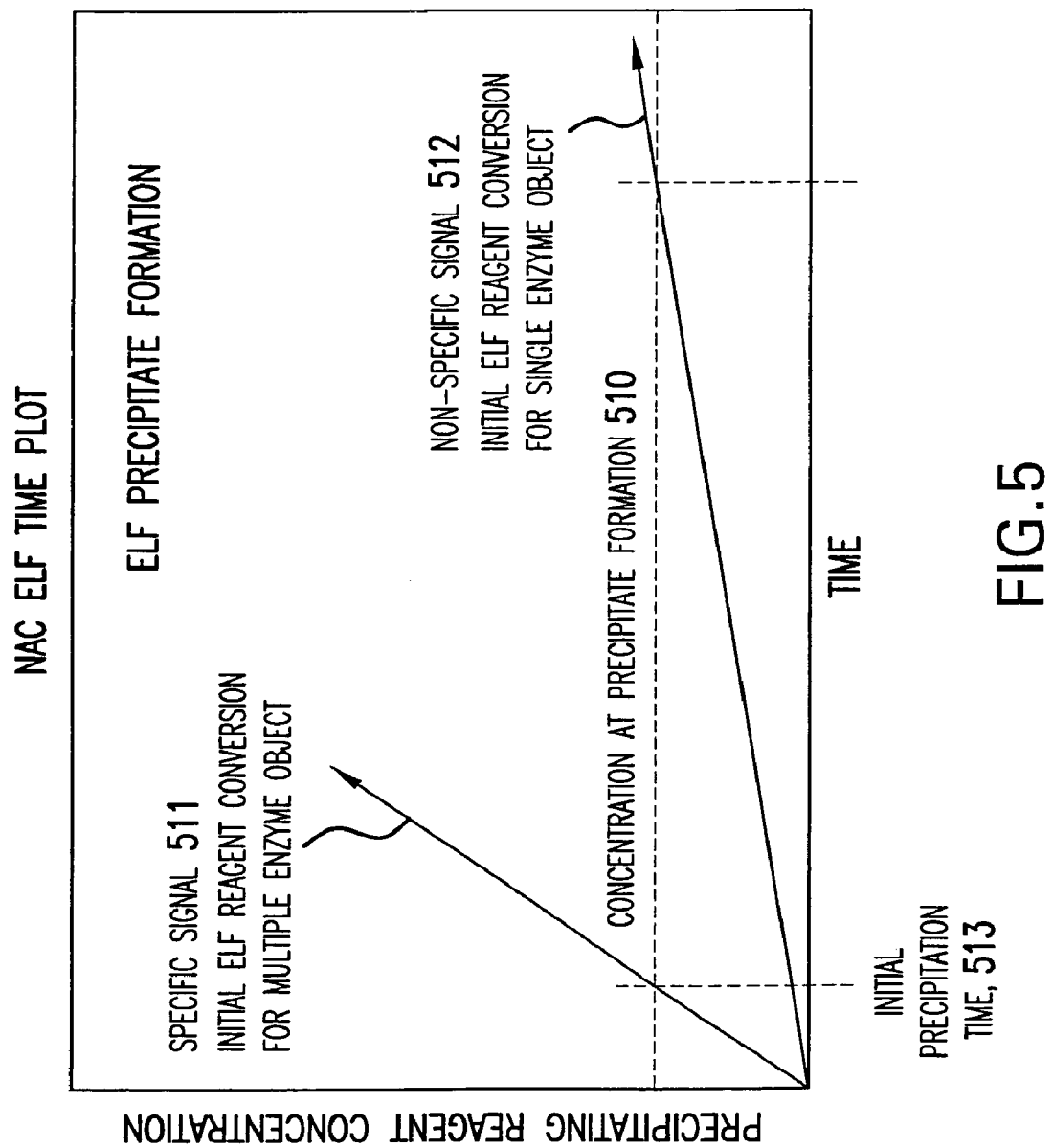
FIG. 5 shows a graph of the timing of a typical ELF process using the techniques described herein.

FIG. 5 shows a graph of the timing of a typical ELF reaction using the methods described herein. The horizontal axis is time and the vertical axis is the local concentration of the ELF precipitating dephosphorylated substrate, also known as the ELF alcohol. A dashed horizontal line, labeled concentration at precipitate formation 510 represents the effective concentration where nanocrystal precipitation will begin. Two diagonal lines are present. The steepest slope line is labeled Specific Signal 511, while the shallow slope line is labeled Non Specific Signal 512. These two lines represent the local ELF alcohol concentration present near locations of high (steep slope) and low (shallow slope) enzymatic activity versus time. Locations of low enzymatic activity may be non-specifically bound conjugates as previously described, while high enzymatic activity locations may be specifically bound enzymes, either due to uninhibited single molecule enzyme activity or multiple probe and enzyme binding in a small area (1 micron$^2$). In this system, fluorescent nanocrystals cannot form until the local concentration of the ELF alcohol exceeds the concentration indicated by line 510. As is seen, at some time into the reaction designated Initial Precipitation Time 513, only the locations of relatively high enzymatic activity have generated sufficient ELF alcohol to cause nanocrystal formation. At later times, even regions of low enzymatic activity can eventually produce nanocrystals. Accordingly, a high SNR for specifically versus non specifically bound probes exists relatively early in the course of the reaction.

Figure 6:
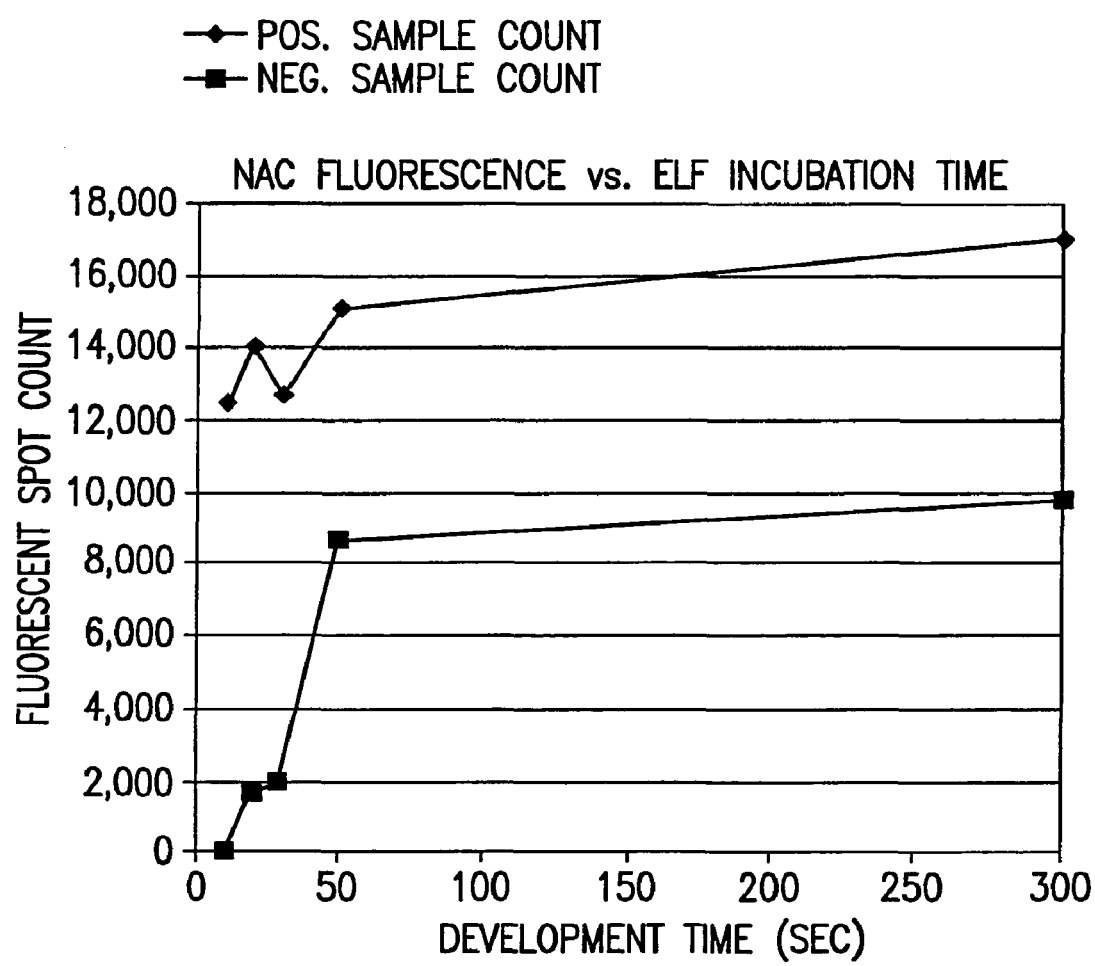
FIG. 6 is a graph showing the fluorescent spot count versus time for nucleic acid counting.

FIG. 6 is a fluorescent spot count versus time graph for nucleic acid counting as described in Example 22. Briefly, lambda phage DNA was prehybridized with 20 complementary biotinylated probes, localized to an improved Nickel-Boron Anopore membrane as described herein, and developed with ELF as described in the Example. As is seen, a clear differential of lambda positive versus lambda negative samples was detected, especially very early in the course of the reaction.

Similarly, tyramide based assays enzymatically generate reactive fluorescent intermediates that covalently attach to proteins near the point of enzymatic activity and may be configured to produce localized microfluorescent zones that may be counted in one-to-one correspondence to the target nucleic acids.

c. Modified Microporous Materials for Enhanced Reaction Rates

In another aspect, the enhanced reaction rates of suspended reactants can be beneficially employed. In one aspect, a suspension matrix is localized near the surface of the microporous material, including any composite described herein, to produce a modified microporous material. In one aspect, the modified-microporous material can be produced by contacting the microporous material with a solution containing the suspension matrix, wherein the solution passes through the microporous material and the suspension matrix remains localized near the surface of the microporous material. In another aspect, the suspension matrix is added to a sample containing the analyte prior to contacting the sample with the microporous material. In this embodiment, the suspension matrix interacts with the analyte prior to localization near the surface of the microporous material. The suspension matrix can interact with the analyte via a covalent bond or any physical or ionic interaction.

Figure 7A:
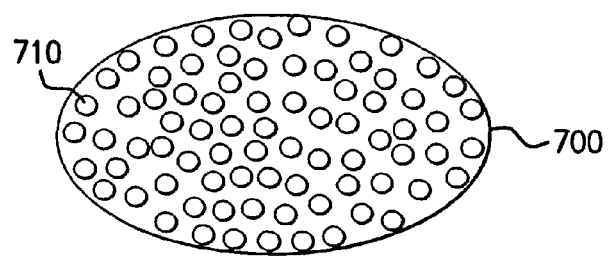
FIG. 7a depicts modified microporous materials and their use for enhanced reaction rates.
Figure 7B:
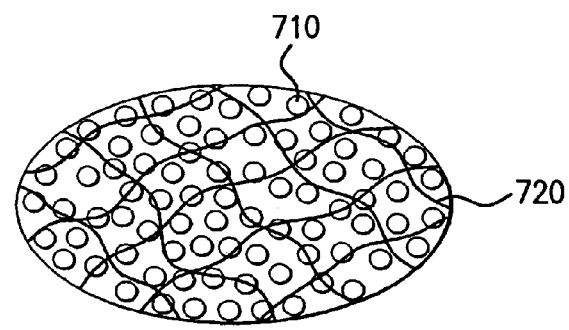
FIG. 7b depicts modified microporous materials and their use for enhanced reaction rates.
Figure 7C:
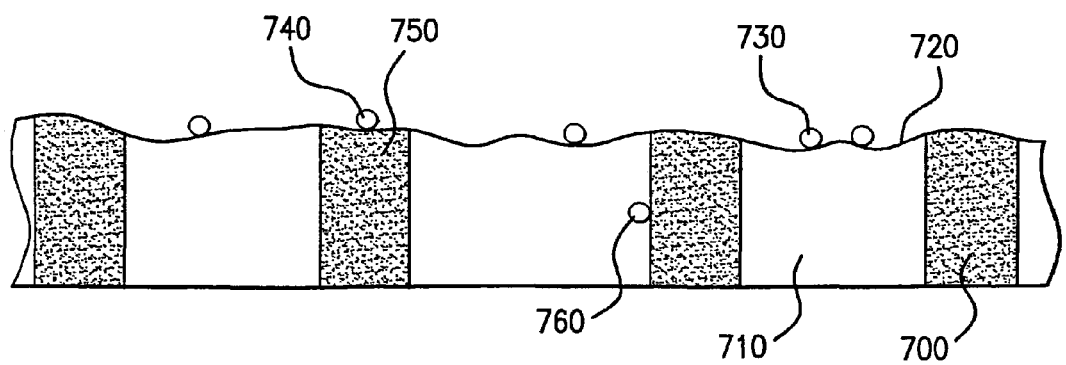
FIG. 7c depicts modified microporous materials and their use for enhanced reaction rates.

One aspect of this is depicted in FIGS. 7a-7c. Microporous material 700 containing micropores 710 is shown in FIG. 7a. FIG. 7b shows suspension matrix 720 localized near the surface of the microporous surface 700 spanning over micropores 710. Suspension matrix 720 is attached to the microporous material 700 sufficiently to prevent molecular collapse through micropores 710 as disclosed herein. In one aspect, the suspension matrix can be localized to the microporous material by, for example, covalent attachment, entrapment, or physical or ionic interactions. FIG. 7c shows a cross section through microporous surface 700 showing suspension matrix 720 "suspended" over micropores 710. Suspended analytes 730 are shown attached to suspension matrix 720 over micropores 710, and non-suspended analytes 740 attached to suspension matrix 720, not over micropores 710 but over the solid surface support of microporous material generally shown as 750. As disclosed, suspended analytes 730 have enhanced reaction rates based on steric hindrance, diffusion, denaturation, etc. compared to non suspended analytes either on the suspension matrix but not suspended over a micropore, as shown at 740, or non-specifically bound or conventionally localized analytes (directly to the surface), as shown at 760.

The suspension matrix can be any macromolecule or similar structure capable of spanning the micropores on the microporous material. Examples include, but are not limited to, organic or inorganic macromolecules, polymers, nanofibers, etc. of sufficient size so as to efficiently localize to the microporous surface. In one aspect, the suspension matrix can be a polymer or macromolecule, such as an oligonucleotide, a polysaccharide, or a protein. In one aspect, the suspension polymer is a nucleic acid such as DNA and analogs thereof and RNA. In another aspect, the suspension polymer is a polysaccharide such as cellulose and starch. Reactants can be proteins or other molecules including, but not limited to, enzymes and antibodies, biomolecules, or catalysts. The analytes can be directly attached to the suspension matrix, for instance through covalent bonds, through a linker, or a binding reaction such as biotin-avidin. The analytes can be attached to the suspension matrix before or after it is attached to the microporous material. For example, antibodies can be attached to DNA in solution by methods generally known in the art, then the DNA, containing the attached antibodies, is localized to a microporous surface. Part of the attached antibodies will be suspended over the micropores and have enhanced reactivity. If the DNA is reversibly localized to the surface, it may be removed by methods disclosed herein, thereby additionally removing the attached antibodies. In another aspect, the DNA containing the antibodies can be reacted in solution with an analyte or tracer of interest to affect specific binding. Here, the DNA-containing attached antibodies and a specifically bound analyte or tracer can then be localized to the microporous surface for enhanced tracer detection as disclosed herein. In this case, the ease of concentrating reactants, for instance antibodies, analytes, and tracers, from solution by localization of a suspension matrix to a microporous material regardless of the relative activity enhancement of suspended analytes is another advantage of this method.

d. Plasmon Resonant Assemblies

Plasmon Resonant Particles (PRP) are metallic submicron particles that display unusual optical properties. In particular, gold and silver PRPs are known to have exceptionally high and wavelength selective light scattering ability. Indeed, a single 60 nanometer gold particle scatters the equivalent photons as the fluorescence emission of 500,000 fluorescein molecules. Silver PRPs are known to be approximately 8 times as efficient as gold although chemically less stable. PRPs have been proposed for use in diagnostics and several companies have been formed to commercialize PRP and related technology.

Spherical PRP optical properties are well known:

1. For very small PRPs (under 40 nm for gold), the scattering cross section is proportional to the particle radius to the sixth power, while the peak scattering wavelength remains constant. In this regime, gold scatters primarily at 520 nm, while silver scatters at 380 nm.

2. As the PRPs become larger (greater than 40 nm for gold), the scattering cross section continues to increase while the peak scattering wavelength shifts to longer wavelengths. For example, the following scattered colors are apparent:

| Gold PRP Diameter | Scattered Color |
|---|---|
| 40 nm | green |
| 78 nm | yellow |
| 118 nm | orange |
| 140 nm | red |

3. Unlike transparent dielectric scattering particles (glass, plastic beads, etc.), PRPs show no reduction of scattering parameters with media refractive index matching. Indeed, while scattering from conventional particles may be essentially eliminated by matching the immersion media refractive index to the intrinsic particle refractive index, scattering from PRPs increase with increasing media refractive index as well as undergo a distinct red shift in peak scattering wavelength.

Characterization of non-spherical (rod shaped, etc.) PRPs are considerably less developed. Published data on rod shaped PRPs indicate essentially a two axis scattering parameter, where scattering wavelength depends on the instantaneous PRP orientation to the illumination light. For example, PRP rods with a diameter of less than 40 nm display a 520 nm scattering peak and a potentially stronger, longer wavelength peak associated with their length.

Characterization of assemblies of spherical PRPs indicate resonant interaction between closely spaced PRPs. That is to say, a linear array assembly of closely spaced spherical PRPs shows long wavelength scattering characteristics similar to an equivalent rod. An assembly of two closely spaced particles will show a fundamental scattering wavelength based on PRP diameter (for instance, 520 nm for <40 nm gold) as well as a longer wavelength associated with resonant interaction between the mutually resonant Plasmon states. A linear assembly of three PRPs will show the fundamental wavelength as well as a unique longer wavelength associated with the long dimension of the three spherical PRP assembly. Much like FRET, this resonant assembly of PRPs is a very short-range process and may be useful for exacting analysis of proximity binding events.

In the methods described herein, when the analyte is a nucleic acid, plasmon resonant assembly (PRA) detection may allow nucleic acid structural analysis. As previously described, a detectable tracer such as multiple probe binding can be used to distinguish specific from non-specific binding events. While the above described multiple probe technique successfully allows discrimination of (NSB) from true target molecules, nucleic acid sequence information is somewhat less certain. Assume a target molecule with a single nucleotide polymorphism (SNP). Additionally, assume 10 probes are synthesized to specifically bind to the 250 base region containing the SNP (assume 10 probes each 25 bases long). Each probe contains a fluorescent reporter means (microbead, quantum dot, highly fluorescent tag, biotin for sequential labeling, etc.) The probe actually coding for the SNP displays measurable and predictable binding deviation (melt temperature, etc.) when compared to the binding on a non-SNP target molecule. Theoretically, it is possible to identify the SNP by anomalous fluorescence intensity changes during probe-target molecule melting or binding under high stringency conditions. Practically speaking, Nucleic Acid Counting (NAC) detectors operate with comparatively low signal to noise ratios consistent with digital molecular detection and cannot reliably detect a 1 of 10 deviation in fluorescence intensity as described in the above example. Fewer probes (say 3 rather than 10) certainly make the fluorescent intensity differences greater for SNP detection, but potentially increase false positives due to NSB.

It would be advantageous if multiple probe binding could be specifically and unambiguously detected at low signal to noise ratios. For instance, fluorescent resonant energy transfer (FRET) is widely used, wherein multiple binding within a small region is detected by unique wavelength emission. A similar system, but with characteristics amenable to NAC detection (high detectability, unique multiprobe signature, etc) may allow SNP identification without molecular multiplication.

PRA detection is capable of distinguishing assemblies of multiple (2, 3, 4 etc.) PRPs uniquely based on optical scattering parameters. For example, a 5-probe system can be used for SNP detection. In one aspect, the probes can be designed to be contiguous with the SNP location under the center (#3) probe. In this case, an assembly of 5 PRPs undergoing predictable melting in the absence of the SNP and an assembly of 5 PRPs melting into 2 assemblies of 2 PRPs for nucleic acids containing the SNP in question is expected. The loss of #3 probe during melting results in a major scattering wavelength shift from the far red (1×5-40 nm gold PRP assembly) to yellow (2×2-40 nm gold PRP assembly). Other schemes are possible, depending on spherical PRP diameter, material, and PRP assembly parameters. Additionally, it is well known silver enhancement can be used to "grow" PRPs in solution starting with very small gold particles. In one aspect, these small gold particles (<2 nm diameter) may prove less prone to NSB on Anopore membranes. Silver enhancement of PRAs, based on small gold nucleation sites may result in more rod like structures and unique detection.

ii. Detection

Once the target analyte is localized, the analyte can then be detected by a detection system. In one aspect, the localized analyte is labeled. Depending upon the detection technique, the analyte can be labeled prior to or after localization. In one aspect, as known in the art, an analog type detection scheme may be employed, where labeled analytes each contribute to an ensemble signal that needs to be of sufficient strength for detection. In another aspect, a digital molecular counting (MC) or digital nucleic acid counting (NAC) detection system can be used to interrogate molecule size zones on the assay target surface for the presence or absence of fluorescence.

Digital detection of the localized analyte can be accomplished with high sensitivity detectors, such as high sensitivity, high spatial resolution fluorescent detectors that interrogate the surface of the microporous material in small regions (e.g. about 1-10 micron areas) for the presence or absence of fluorescent signal from the labeled analytes. The interrogation area is sufficiently small, and the localized analyte surface concentration is sufficiently low so as to practically allow only 0 or 1 labeled analytes within the interrogation area. An analyte is considered counted when the detected signal exceeds a preset or dynamically calculated threshold determined by the relative magnitude of the fluorescent signal from the labeled target analyte and the background signal.

In another aspect, detection of the analyte can be accomplished with other techniques including, but not limited to, fluorescence, phosphorescence, chemilumenescence, bioluminescence, Raman spectroscopy, optical scatter analysis, plasmon resonant particle (PRP) analysis, etc. and other techniques generally known to those skilled in the art.

In the case of digital nucleic acid detection, some or all of the following nucleic acid detection requirements should be met depending on the type of detection system utilized.

1. Unambiguously isolate the fluorescence from an interrogation zone approximately 1 to 10 microns in area.
   2. Measure fluorescent emissions from the interrogation zone with high efficiency and sensitivity consistent with the fluorescent labeling system used.
   3. Measure approximately 5,000 to 500,000 discrete interrogation zones per second.
   4. Maintain focus on the target surface during measurement.
   5. Maintain intensity-location relationship (image formation) for background subtraction.

Examples of suitable detection devices that can be used herein include, but are not limited to, high speed scanning confocal epifluorometers, high sensitivity fluorescent confocal microscopes, charge coupled device (CCD) arrays such as CCD array based fluorescent microscopes, image intensified cameras, and the like. High speed scanning confocal epifluorometers are able to detect a few fluorescent labels on each nucleic acid. Several labeling schemes previously discussed (e.g., fluorescent microbeads, nucleic acid dyes, enzymes, quantum dots, etc.) produce substantially greater signal and are detectable with less sophisticated equipment.

Recent advances in ultra high sensitivity optical detection have resulted in the ability to identify single fluorescent molecules, which permits numerical counting of single molecules localized to surfaces. In one aspect, a labeled analyte that is localized near the surface of the microporous material can be detected by optical detection. Optical detection generally involves detection methods employing electromagnetic radiation in the wavelength range of about 200 nm to about 20,000 nm. In one aspect, for ultra low concentration nucleic acid detection, such as found in ultra sensitive viral load assays, and the like, optical detection can be used in any of the methods described herein for the direct determination of nucleic acid concentrations without molecular amplification.

In one aspect, when a sequential fluorescent staining approach as described above is used to label a localized nucleic acid, and the two dyes (A and B) are the same, the optical surface is measured twice, once after initial staining and again after complimentary specific binding oligonucleotide probe addition. In one aspect, the detector used in this case is an imaging detector such as a confocal fluorescent microscope, CCD camera, or the like. The images obtained from these respective measurements are simply subtracted to derive the true target nucleic acid count. This is true even if the true target nucleic acid partially stains during the initial staining.

An example of this type of technique is an HIV viral load nucleic acid detection assay using the dye Picogreen. This dye is known to preferentially stain double strand DNA or DNA-RNA hybrids. The nucleic acids in a patient sample, including single strand HIV RNA, are localized near the surface of a microporous material, such as an Anopore membrane. Picogreen solution is added and fluorescently stains all localized double strand nucleic acids, including self hybridized (hairpin, etc) regions of the HIV RNA. The membrane filter is fluorescently imaged to produce a background image measurement. Oligonucleotide probes, complimentary to the HIV RNA, are added and allowed to specifically hybridize to the single strand HIV RNA. Picogreen solution is again added (or simply not removed from the first staining and hybridization steps) and the membrane filter is reimaged. The previously taken background image is subtracted from this second image to create a difference image. This difference image represents the HIV RNA regions that specifically hybridized with the complimentary oligonucleotide probes. Target HIV RNA is then detected as fluorescent spots or pixels on the difference image.

In the example above, if dyes A and B are spectrally independent, only the dye B measurement is required. Dye A may be nonfluorescent so that it simply blocks non-target nucleic acid binding sites for fluorescent dye B. In this case, non-imaging detectors may be employed for nucleic acid detection since fluorescent images need not be subtracted.

a. Scanning Confocal Epifluorometer

Figure 8:
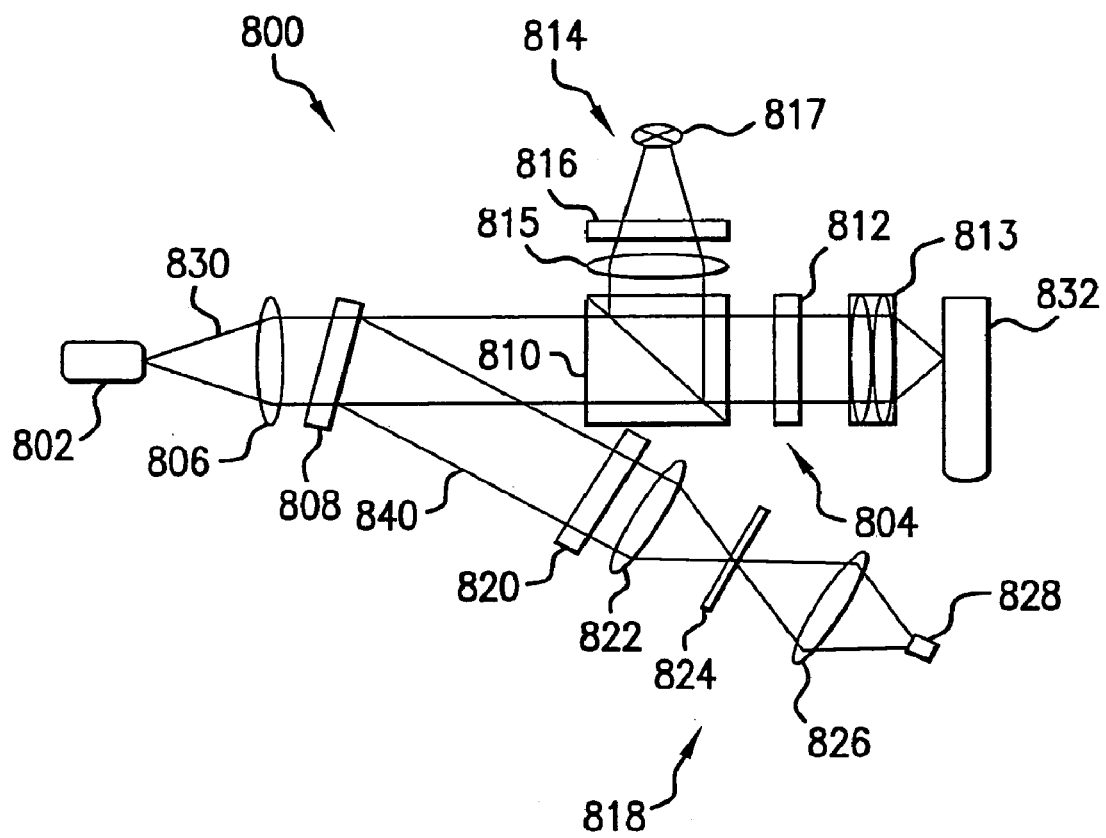
FIG. 8 depicts a device for the detection of localized analytes.

One aspect of a suitable scanning detection system for use in molecular counting is shown schematically in FIG. 8. The detection system, designated generally as 800, includes a laser light source 802 that is in optical communication with a light beam delivery and collection module 804, which can include various optical components for directing laser light to the sample to be measured and collecting the fluoresced light. As shown in FIG. 8, the optical components of delivery and collection module 804 include a collimating lens 806, a fluorescence beam splitter 808, a polarizing beam splitter 810, a quarter wave plate 812, a dynamic focus objective lens 813, and a focus detector 814. The focus detector 814 includes a focus lens 815, a cylindrical lens 816, and a quadrant photo-diode detector 817. The interaction of these optical components with a laser beam from light source 802 will be discussed in further detail below. The delivery and collection module 804 is in optical communication with a detector module 818, which includes an interference filter 820, a first focus lens 822, a spatial filter 824, a second focus lens 826, and a photon counting avalanche photodiode (APD) 828.

During operation of detection system 800, a laser beam 830, such as a linearly polarized continuous wave (cw) laser beam, is expanded and collimated to a preselected diameter, such as up to about a 6 mm diameter. The laser beam traverses fluorescence beam splitter 808, polarizing beam splitter 810, quarter wave plate 812, and is focused onto the interior surface of sample container 832 by dynamic focus objective lens 813. The fluorescence beam splitter 808 transmits laser beam 830 and reflects all other wavelengths of light. The fluorescence beam splitter 808 can be set at an angle such as approximately 15 degrees incidence to minimize polarization effects and improve the signal-to-noise ratio. The polarizing beam splitter 810, in conjunction with quarter wave plate 812, forms a traditional optical isolator. The linearly polarized laser light traverses polarizing beam splitter 810 and is converted into circularly polarized light by quarter wave plate 812. Specular reflection of this light reverses the direction of the circular polarization (right hand into left hand circularization). This opposite hand polarized light is converted into linearly polarized light upon returning through quarter wave plate 812. This return light is linearly polarized orthogonally to the original laser beam, and is reflected at 90 degrees through polarizing beam splitter 810 to focus detector 814.

The dynamic focus objective lens 813 maintains laser beam and fluorescence detector focus on the target surface during scanning. Scanning can be accomplished by rotating sample container 832 (e.g., disposable polystyrene culture tubes, inorganic optical membrane filters, etc.) while moving the container or detector along the container axis. Alternative scanning schemes use scanning mirrors (not shown) between quarter wave plate 812 and objective lens 813 to scan in orthogonal directions. The objective lens numerical aperture (NA) can be limited to about 0.6 to allow enough depth of focus for the auto focus system to work, as well as allow a convenient working distance between objective lens 813 and sample container 832.

The objective lens 813 can be placed in a linear motor (voice coil) and translated towards or away from sample container 832 under closed loop control of the focus system to maintain focus on the interior surface of sample container 832 during scanning. As is well known to those skilled in optical design, optical reflection will occur at the interface between two transparent materials of different refractive indexes. For example, the reflection from a glass-to-water interface is approximately 0.5%, while the reflection from a glass-to-air interface is approximately 4%. The detection system 800 can be configured to dynamically focus on a dry surface (interface), or on the interface formed between a solid and a fluid. Accordingly, the weakly reflected laser light (about 0.5%) from the container-fluid interface traverses cylindrical lens 816 of focus detector 814 and illuminates photodiode detector 817. The optics are such that when objective lens 813 is in focus with the container-fluid interface, a circular spot is generated on focus detector 814. Deviation from the ideal focus location results in elongation of the circular spot. This elongation is measured by photodiode detector 817 and used as an error signal in a feedback loop focus controller for objective lens 813.

Fluorescence from the interior surface of sample container 832 follows a return path along that of the laser excitation and is reflected by fluorescence beam splitter 808. In this location, most specularly reflected excitation light has been removed from the fluorescence signal by polarizing beam splitter 810. Depending on fluorescence polarization, some fluorescent signal may also be lost. In an alternative configuration, fluorescence beam splitter 808 may be located between quarter wave plate 812 and objective lens 813. In this alternative location, the fluorescent signal will be greatest, but also will have additional reflected excitation light. As shown in FIG. 8, a reflected fluorescence beam 840 from fluorescence beam splitter 808 traverses inference filter 820, which can be a very high efficiency, multicavity interference filter. The fluorescence beam 840 is focused onto spatial filter 824 by lens 822. The spatial filter 824 is located at an image plane of the container-fluid surface and improves spatial resolution and signal-to-noise ratio by eliminating light from other areas. The light traversing spatial filter 824 is focused by lens 826 onto a small area of photon counting avalanche photodiode 828. Depending on the active photodiode area and image magnification, the spatial filter system may be simplified by directly focusing the fluorescent light onto a small area photodiode. As is well known to those skilled in the art, images may be constructed by tracking signal intensity versus scan position. Such images can be visually displayed on an output display such as a computer monitor or the like, or further analyzed by a computer to count the detected nucleic acids. It will be understood by those skilled in the art that detection system 800 may be configured for use with many different geometries, such as filter membranes, flowcells, multiwell plates, and the like.

b. Camera Based Dark Field Fluorometer

Figure 9:
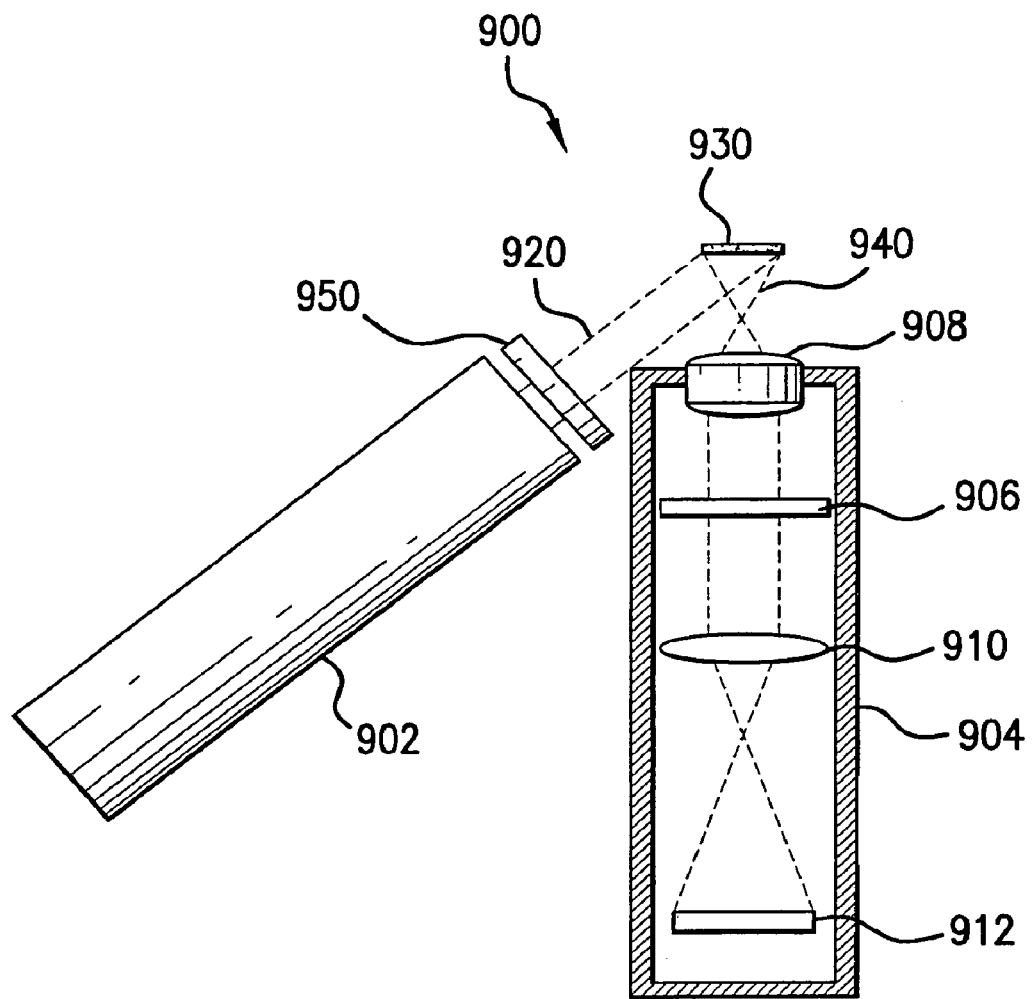
FIG. 9 depicts an alternate device for the detection of localized analytes.

Another suitable detection system that can be used in the molecular counting methods described herein is shown schematically in FIG. 9. The detection system, designated generally as 900, is particularly suited for detecting nucleic acids localized on a microporous material. The detection system 900 includes a light source 902 including excitation filter 950, that is in optical communication with a detector module 904 such as a charge coupled device (CCD) camera. The detector module 904 includes one or more interference filters 906 to isolate labeled nucleic acid fluorescence. The detector module 904 can have a flat field objective lens 908, such as a lens having an NA of about 0.1 to about 0.3 to achieve a depth of focus of about 5 microns to about 15 microns. This large depth of focus allows latitude in sample filter membrane location. Alternatively, higher NA objective lenses may be used to collect additional signal, but with smaller depth of focus. The detector module also includes a detector lens 910, and CCD array 912, such as a cooled high quantum efficiency back thinned CCD detector, for exposures of several seconds to several minutes. Other optical designs involving through the lens and fiber optic illumination can also be employed in alternative embodiments.

During operation of detection system 900, an illumination beam 920 is directed to the surface of the microporous material 930 having nucleic acids localized thereon. The illumination beam 900 causes fluorescently labeled analyte to fluoresce. A localized analyte, even labeled with many fluorescent microbeads, is still a very small object. Each labeled analyte will typically generate a single bright pixel on CCD array 912 from a fluorescence beam 940. Assuming detector system 900 is designed for a 3 mm diameter target surface with a 1000×1000 CCD array, each pixel represents an area of about 3×3 microns on the membrane filter. The detector system 900, unlike the previously described scanning confocal system of FIG. 8, can be designed for analytically uniform illumination and detection. This should allow pixel signal intensity to be correlated with fluorescent nucleic acid concentration per pixel. Accordingly, closely spaced analytes (within the same pixel) may be resolvable by step functions in pixel intensity, improving detector counting dynamic range. The images produced by the CCD array can be visually displayed on an output display such as a computer monitor, or further analyzed by a computer to count the detected analytes.

c. Scanning Darkfield Spectrometer

Figure 10:
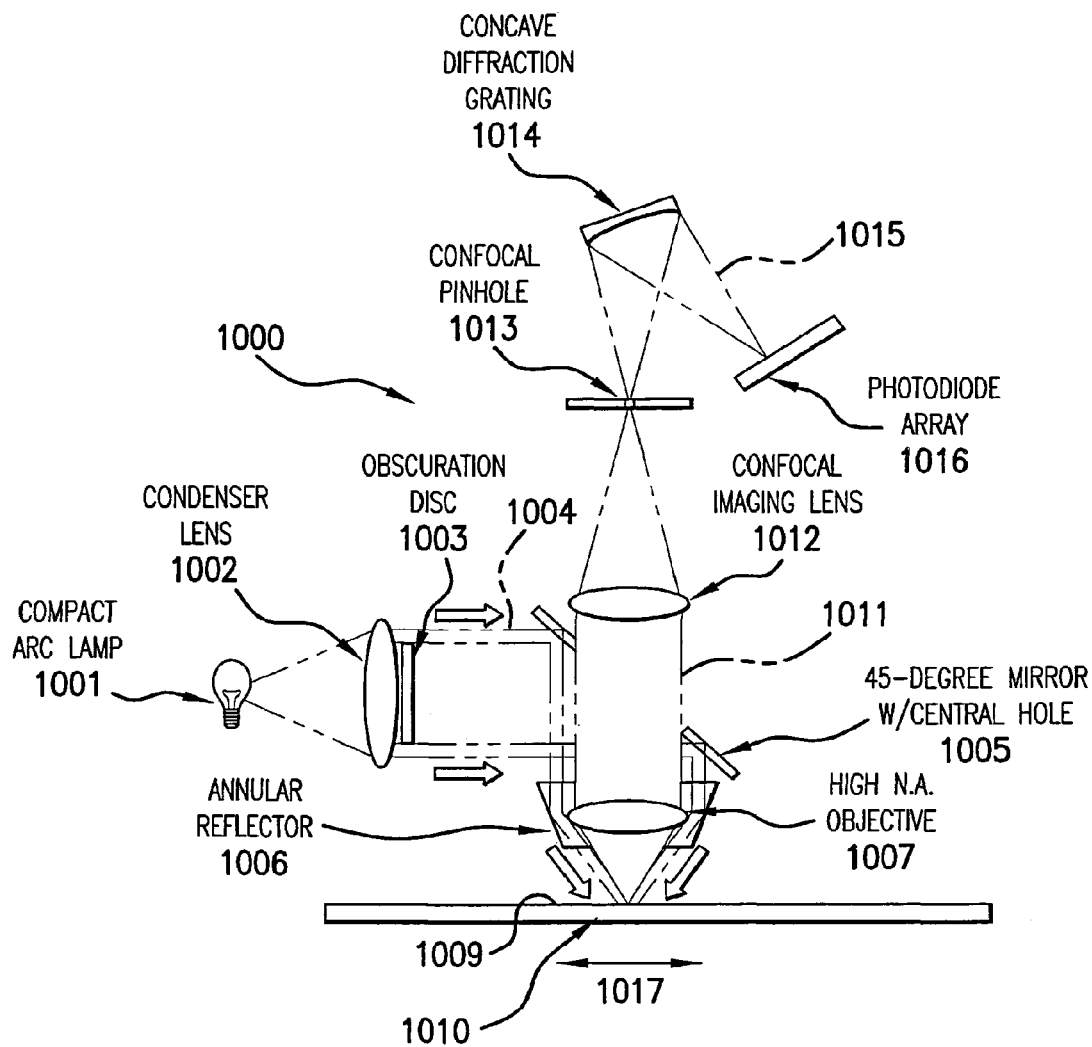
FIG. 10 depicts an alternate device for the detection of localized analytes.

In one aspect, a detector suitable for molecular counting based on Plasmon resonance assembly (MC-PRA) detection is shown in FIG. 10 and generally identified as 1000. It is best characterized as a dark field, confocal scanning spectrometer. Unlike fluorescent-based systems previously described for molecular counting, this detector operates with substantial light levels and does not require high sensitivity detection.

Illumination should be from a white light source and be positioned such that direct reflections are not detected by the detector. This is typically accomplished using a high intensity, compact arc lamp with suitable optics to illuminate the microporous material at an angle greater than the total collection angle of the detection objective. This may be done with conventional microscope dark field illumination equipment or dark field metallographic microscope objectives and related hardware. Compact arc lamp 1001 emits broadband (multiwavelength) light which is collimated by condenser lens 1002. This light impinges on obscuration disc 1003, which forms annular illumination beam 1004. This annular beam of illumination light is reflected by mirror 1005, containing a central hole for detected light to pass through. The annular illumination is reflected by annular reflector 1006 at an angle greater than the maximum optical collection angle of objective 1007 to illuminate nucleic acids containing suitable labels 1009 localized on the microporous material 1010. In this way, specularly reflected illumination light, for instance from a first surface reflection from the microporous material, cannot enter the collection optics. Optical signal is collected by objective 1007 relatively free from first surface reflection and passes through the hole in mirror 1005 and is imaged onto confocal pinhole 1013 by lens 1012. Confocal pinhole 1013 assists in lowering spurious scattered light, etc. The light that traverses the pinhole is directed to concave grating 1014, where it is dispersed into separate wavelengths 1015 and is detected by photodiode array 1016. This array simultaneously detects multiple wavelengths present in the scattered signal from the PRA labeled nucleic acids. As previously discussed, the intensity of these scattered wavelengths may be used to determine labeling parameters of the localized nucleic acids. In this example, scanning may be accomplished by moving the membrane assembly under a stationary detector as shown by 1017, or alternatively moving the detector assembly while keeping the membrane assembly stationary.

Scattered light from the PRA originates within a very small area near the surface of the microporous material. It is advantageous to employ high numerical objectives and confocal geometry to limit extraneous scatter from reaching the detector.

The MC-PRA detector should simultaneously detect multiple wavelengths. FIG. 10 depicts one embodiment of this, where it is accomplished by employing an optical grating to disperse the scattered light traversing the confocal pinhole onto a linear array photo detector. Light levels are sufficiently high to allow conventional photodiode detectors rather than more expensive photon counting and cooled CCD systems.

d. Melting Curve Analysis

When the analyte is a nucleic acid, melting curve analysis (MCA) is a technique based on the reversible nature of nucleic acid hybridization. Double strand nucleic acids, as well as single strand nucleic acids with extensive secondary structure (self hybridization), revert to simple single strand configurations under well-defined conditions of temperature and solvent composition. This process is referred to as melting. Many nucleic acid stains show large fluorescence enhancement when bound to double strand nucleic acid segments, and will lose fluorescence when these double strand segments melt. A melting curve is generally a plot of the fluorescence versus temperature of a fluorescently stained nucleic acid. The shape of the curve contains information regarding the structure of the melting nucleic acid and may be used as a specific, although low resolution, indicator of nucleic acid identity. This technique is widely used in real time PCR analysis and molecular biology.

In one aspect, MCA can be used to differentiate target nucleic acids in a mixture of a few different nucleic acids. In one aspect, nucleic acid localization and labeling is carried out as described above, with the MC detection system modified to control and vary membrane filter temperature or other factors known to cause nucleic acid melting. This may be accomplished by controlling the temperature of the fluid flowing through the microporous material, controlling the temperature of the entire disposable, solvent composition, etc. A nucleic acid counting melting curve analysis (NAC-MCA) is performed by taking NAC measurements at several microporous material temperatures and correlating fluorescence changes versus temperature to known properties of the target nucleic acid.

For example, a target nucleic acid may have a melting point of 80° C. The detection instrument is set to make NAC measurements from about 75° C. to about 85° C. in 0.5° C. increments. Target nucleic acid will undergo a specific fluorescence reduction as the melting temperature is reached. Non target nucleic acids will most likely melt at a different temperature. The detection instrument is set to only count nucleic acids that melt within a predefined range. For applications involving limited numbers of contaminating non target nucleic acid types, this added specificity can eliminate the complication of developing complimentary probes, stains, etc. It is contemplated that single strand RNA with extensive secondary structure (e.g., HIV, HCV, entrovirus, etc.) can be analyzed by NAC-MCA, with the stained secondary structure melting at a predictable, unique temperature. Additionally, multiple complementary nucleic acid binding probes may be designed for a specific target nucleic acid, for instance HIV, that all melt at a uniform temperature. In this case, localized HIV hybridized to multiple probes and stained with a suitable nucleic acid dye will melt at a well defined temperature unique to the specific probe design.

Figure 11:
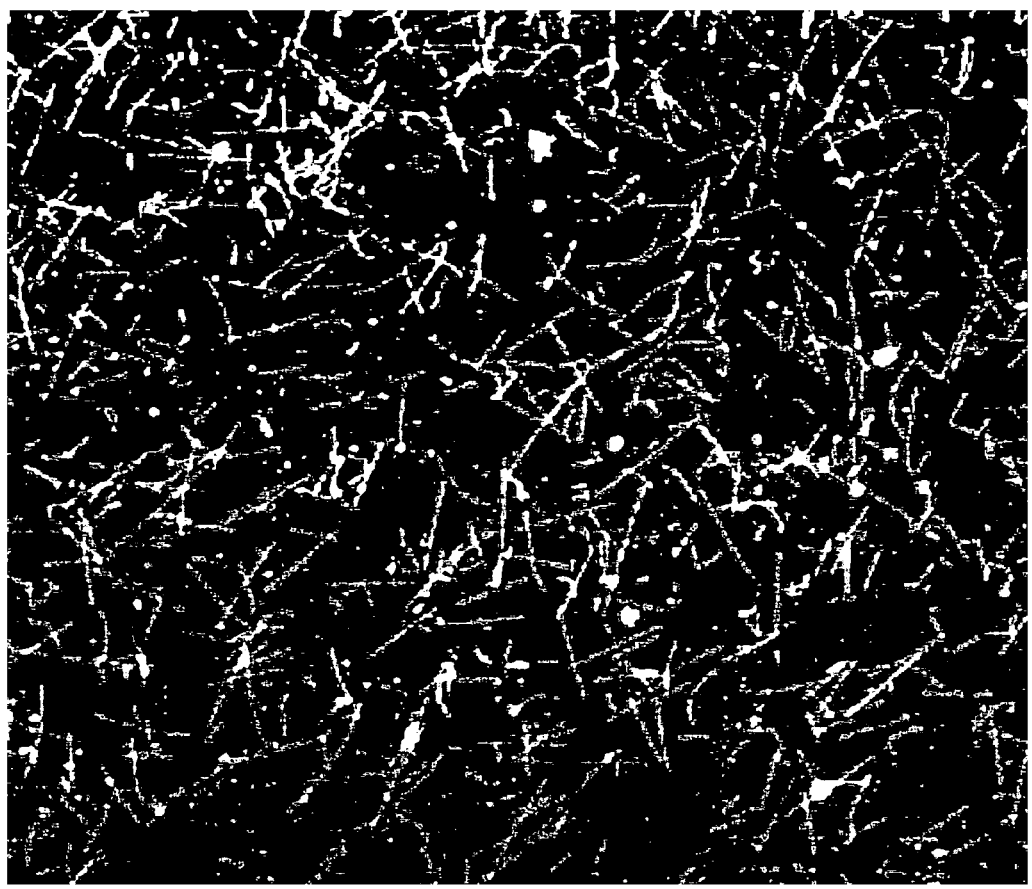
FIG. 11 shows human genomic DNA localized on a nickel/boron Anopore surface and stained with Syber Gold dye.
Figure 12A:
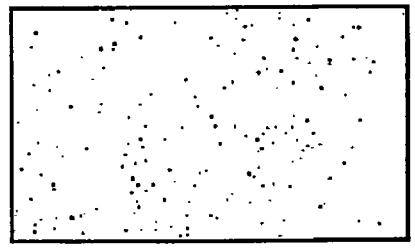
FIG. 12a depicts processed, negative images of the YOYO-1 labeled calf thymus DNA that was optically detected.
Figure 12B:
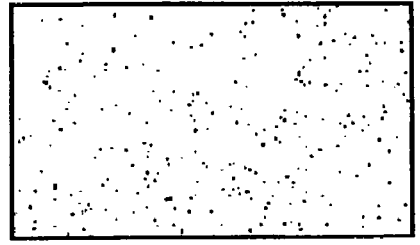
FIG. 12b depicts processed, negative images of the YOYO-1 labeled calf thymus DNA that was optically detected.
Figure 12C:
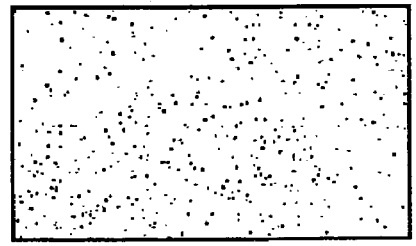
FIG. 12c depicts processed, negative images of the YOYO-1 labeled calf thymus DNA that was optically detected.
Figure 12D:
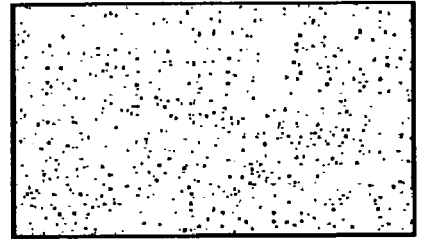
FIG. 12d depicts processed, negative images of the YOYO-1 labeled calf thymus DNA that was optically detected.
Figure 12E:
FIG. 12e depicts processed, negative images of the YOYO-1 labeled calf thymus DNA that was optically detected.
Figure 12F:
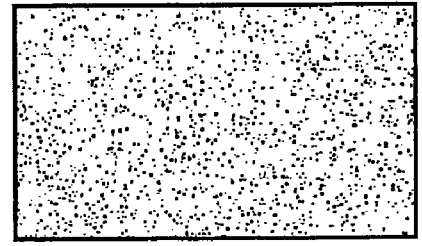
FIG. 12f depicts processed, negative images of the YOYO-1 labeled calf thymus DNA that was optically detected.
Figure 12G:
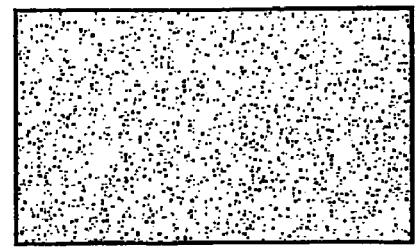
FIG. 12g depicts processed, negative images of the YOYO-1 labeled calf thymus DNA that was optically detected.
Figure 12H:
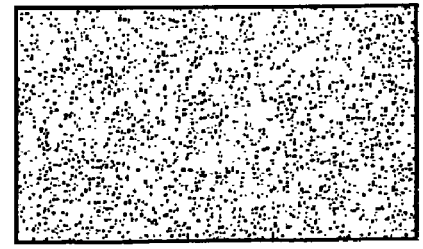
FIG. 12h depicts processed, negative images of the YOYO-1 labeled calf thymus DNA that was optically detected.

In certain circumstances, localized nucleic acid morphology can be used to improve detection SNR. As previously discussed, nucleic acids are molecules of exceptionally high aspect ratio. Many target nucleic acids are localized with clearly identifiable morphology. FIG. 11 shows human genomic DNA localized on a nickel boron Anopore membrane stained with Syber Gold dye and imaged with the detector shown in FIG. 9 according to Example 12. The rod shaped DNA is clearly visible. In this case, although the pixel brightness of the DNA is greater than the surrounding background pixels, the DNA is identified primarily by shape. Image analysis techniques are available to aid in identifying particular shapes, correct for overlapping regions, improve image quality, etc. and improve counting accuracy. Certain nucleic acids and staining techniques can result in optically identifiable structures that do not easily fit within a compact detection zone, may present substantial image overlap, and otherwise require image analysis techniques to identify individual nucleic acids. These techniques are widely used and known to those skilled in the art.

iii. Counting

Immobilization of relatively pure analytes near the surface of the microporous material, which is accomplished by the techniques described herein, is an important variable with respect to counting the analyte. The term "counting" is defined herein as determining the number of individual analyte particles localized near the surface of the microporous material at a particular area of the microporous material. Single molecule counting, even for relatively large, multilabeled analytes, requires exceptional detectability. Consequently, single molecule counting requires immobilizing substantially purified analytes free of competing or interfering substances. The following principles demonstrate how surface immobilization as accomplished by the techniques described herein enhance molecular counting.

For optical systems, it can be mathematically shown that the light gathering ability of an instrument is proportional to the depth of focus. That is to say, detected fluorescent signals in an instrument optimized to interrogate fluorescent particles localized in a 1 micron deep region will be at least 100 times greater than an equally well optimized instrument interrogating the same fluorescent particles localized in a 100 micron deep region. The 1 micron depth of focus instrument could be used to stepwise interrogate the 100 micron deep region, but would take 100 times as long.

Optical molecular counting requires isolating exceptionally small volumes for optical interrogation. The most straightforward approach to counting the analyte is to interrogate a very small detection volume for the presence or absence of a target molecule. As the detection volume becomes larger, molecular resolution is lost, the background signal derived from nonspecific sources within the detection volume becomes greater, and specific signal derived from the presence of the target molecule may be lowered, thereby lowering the practical ability to discern when a target molecule is within the detection volume.

Although small detection volumes result in increased molecular resolution and improved optical signal to noise ratio, such volumes also affect assay time. Given a detection volume (for instance based on required resolution and counting signal to noise ratio), the required counting time is proportional to the total volume that must be interrogated. For example, a 200 microliter (μl) patient sample may contain only 10 target nucleic acid molecules. Assuming a detection volume of 10 cubic microns, a 200 microliter volume will have to be interrogated 20 billion times to count the 10 target molecules. If the 10 target molecules are localized to a surface 5 millimeters in diameter, the surface will have to be interrogated approximately 1 million times. Localizing the target molecules to a filter surface as disclosed herein represents an effective concentration improvement of 20,000 based on detection, which translates to an equivalent savings in assay time.

Molecular location should be known during optical counting. Interrogating millions to billions of detection volumes within a sample can take minutes to complete. Freely diffusing molecules can be counted multiple times by high speed scanning detectors, or not at all with integrating charge coupled device (CCD) array detectors. Thus, target molecule location is most easily controlled by immobilization near the surface of the microporous material. In the case of nucleic acid counting, it is preferable that the microporous material be nonfluorescent and able to immobilize target nucleic acids under conditions where hybridization and/or fluorescent staining can occur.

For an acceptable analyte counting assay, the following conditions should be considered:

1. Signal-to-Noise Ratio (SNR): target analytes should be sufficiently fluorescent to achieve an instrument signal-to-noise ratio consistent with acceptable error rates. In the case of nucleic acids, calculations show a SNR of greater than 3 or from about 3 to about 50, from about 3 to about 40, from about 3 to about 30, from about 3 to about 20, or from about 3 to about 10 is desirable for unambiguous, low error rate nucleic acid counting.

2. Assay Specificity: non target analytes should be nonfluorescent consistent with acceptable assay specificity requirements.

3. Dynamic Range: target analytes should be localized near the surface of the microporous material as resolvable, discrete fluorescent entities. That is to say, each target analyte should be individually countable from all others. Thus, each pixel or detection zone that the detector interrogates should contain either 1 or 0 fluorescent target analytes, or signal processing technologies may be employed to identify the boundaries of individual molecules to prevent miscounting.

The ratio of detected signal when a target analyte is present in the interrogation volume to the detected signal in the absence of a target analyte is defined as the signal-to-noise ratio (SNR). The detected signal can be based simply on intensity at a certain wavelength, or a complex parameter involving intensity, multiple wavelengths, phase, timing, etc. The required SNR is a function of instrumentation design and assay requirements. Example 14 below presents calculations for a scanning confocal epifluorometer based nucleic acid counter, including estimates of required SNR, design interrogation area, required scan times, and hardware assumptions.

When the analyte is a nucleic acid, a limiting factor for achieving high SNR in a nucleic acid counting assay is non-specific tracer binding. Tracers, whether nucleic acid stains or oligo-based fluorescent probes, will likely be present near the surface of the microporous material unassociated with target nucleic acids. This nonspecific tracer will generate a fluorescent signal when interrogated that must not be miscounted as target nucleic acid.

For example, when localized target nucleic acids are to be labeled with an oligonucleotide based fluorescent probe, if each localized target nucleic acid hybridizes with only one fluorescent probe in the detection region, and the relative fluorescence characteristics (quantum yield, wavelength, etc.) are the same for specific and non specifically bound probes, the target nucleic acid is indistinguishable from randomly located nonspecifically bound probes. This is true regardless of the degree of fluorescent labeling on the probe, which can include fluorescent bead labels, quantum dots, surface plasmon resonance particles, multiple labels, etc. In this case, a true SNR of 10 requires a minimum of 10 probes specifically bound to the target nucleic acid in one detection region, assuming the probe nonspecific binding (NSB) remains as isolated, individual molecules that are not clumped together.

The above situation is based on simple intensity measurements of detection zone fluorescence employing multiple probes each labeled with a common fluorescent tag. If each probe is labeled with a clearly separate fluorescent tag to form a separate, identifiable detectable tracer, higher effective SNR at lower probe numbers may be possible. For example, the required SNR for a counting assay is based on the allowable frequency of miscounting a non specific event. In a simplified case, this is similar to determining the probability a non specific event will be identical (as detected by the instrument detector) to the desired specific event. Suppose a common tag (for instance intensity measurement of one fluorescent wavelength) system operates with 5 probes. The probability a non specific event will be as intense as five combined probes is low. A system based on five probes with separately identifiable tags (for instance wavelength and intensity) has an even lower probability a non specific event will be as intense and contain all the required wavelengths in the correct ratios. Accordingly, more complex detection schemes may be employed to maintain high effective SNR with reduced probe numbers.

High effective SNR may also be achieved with lower probe numbers by employing techniques where non specifically bound probes do not elicit the same optical response as those specifically bound to a target nucleic acid. This is similar to the use of nucleic acid stains that undergo substantial quantum yield increase on binding to nucleic acids. Enzymes are known to frequently lose substantial activity when in contact with surfaces. As disclosed herein, specifically bound probes labeled with enzymatic tags may be considered suspended over the microporous surface on the localized nucleic acid rather than in direct surface contact as are the non specifically bound probes. Accordingly, enzyme labeled probes may exhibit high effective SNR with low probe numbers.

iv. Correlating the Analyte Concentration

The term "correlating" as used herein is defined as quantifying the concentration of the analyte present in a known volume of sample based on the number of analyte particles counted on the microporous material and corrected for known relationships such as the localization efficiency of the microporous material, labeling efficiency, detection efficiency, field of view, etc.

In one aspect, qualitative nucleic acid counting or detection may be advantageously performed. In this aspect, final correlation of detected signal to the initial sample concentration is of lesser importance. For instance, identification of the presence or absence of a pathogen, rather than exact concentration, is frequently sufficient for diagnosis. Examples include, but are not limited to, identification of biological warfare agents, identification of Strep A bacteria in throat swabs, identification of the MecA gene in S. Aureus cultures to determine drug resistance, etc. The microporous materials, methods, and articles described herein provide qualitative analysis through speed, ease of use, elimination of molecular amplification steps (such as PCR), simplified hardware requirements, the ability to use multiple sample types without preprocessing, etc. without consideration of final result correlation to initial concentration.

In another aspect, the ability to correlate the counted nucleic acids with an initial sample nucleic acid concentration is important to quantitative analysis. Indeed, methods of counting immobilized nucleic acids have existed for many years. For instance, it is well known in the art nucleic acids may be immobilized to quartz surfaces by simply contacting a relatively high concentration sample with a clean surface. Some of the nucleic acids will "stick" to the quartz and may be counted by Atomic Force Microscopy (AFM), Scanning Electron Microscopy (SEM), etc. In one aspect, the microporous materials, methods, and articles described herein improve the current state of the art by the ease and speed with which nucleic acids may be localized to the microporous material, the wide variety of sample types and purity allowed for localization to the microporous material, and the ability to correlate the counted nucleic acids to the initial nucleic acid sample concentration.

The microporous materials described herein permit the localization of analytes through a process similar to mechanical filtration. This localization step is essentially quantitative for certain analytes such as certain sizes of nucleic acids, with nearly 100% of all target nucleic acids localized near the surface of the material for identification by detection such as counting or additional processing steps such as PCR, etc. This very high localization efficiency permits the analysis of very low concentration substances that may only occur as a few copies per milliliter of sample.

The repeatability of localization also effects correlation. For example, if the microporous material always captures 2% of the nucleic acids, a correlation between nucleic acid count and initial sample concentration may be established, although certainly with lower sensitivity than if 100% of target nucleic acids are always captured and available for analysis. The microporous materials, methods, and articles described herein permit localization that is both exceptionally efficient and repeatable.

Instrumentation, hardware, and processing parameters should be predictable for successful correlation. For example, if a quantitative assay for a circulating virion is desired, the following parameters should be known in order to correlate the final detected nucleic acid count with initial virion concentration.

1. Virion lysis efficiency
2. Initial sample volume across the capture membrane
3. Nucleic acid capture efficiency
4. Nucleic acid labeling efficiency
5. Labeled nucleic acid detection efficiency
6. Percent of membrane interrogated by detector
7. System linearity versus detected signal Unlike existing analyte counting methods, correlation between final analyte count and initial sample volume through efficiency and repeatability of the above defined parameters is improved substantially. FIGS. 12a-12h depict processed, negative images of the YOYO-1 labeled calf thymus DNA that was optically detected according to Example 13. Relative DNA concentrations in the filtered test samples were increased from 1 in FIG. 12a up to 128 in FIG. 12h. As seen in FIGS. 12a-12h, individual nucleic acids can be easily counted in the range of interest for high sensitivity diagnostic assays.

Figure 13:
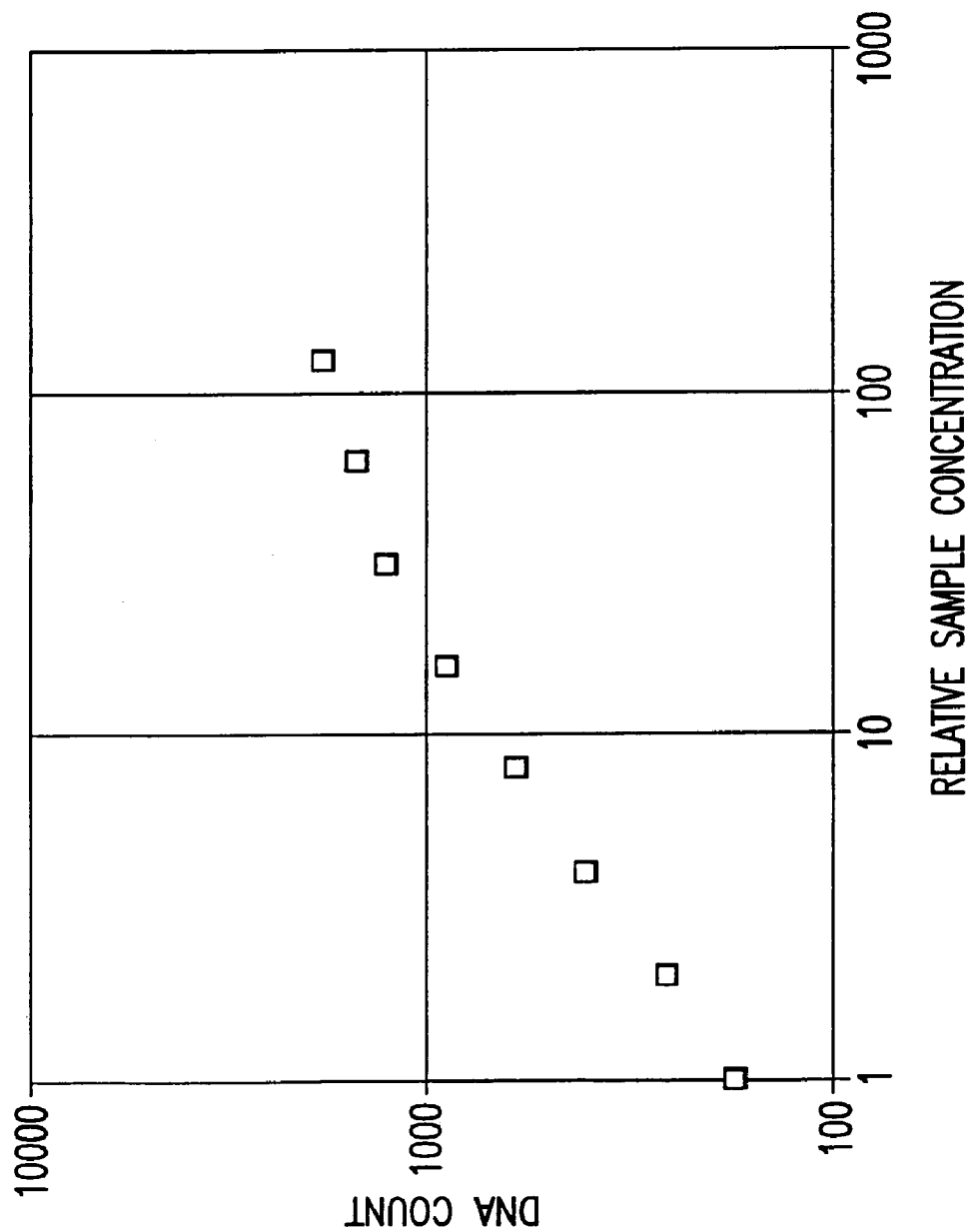
FIG. 13 is a graph of an uncorrected nucleic acid counting (NAC) assay calibration curve.

FIG. 13 is a graph of uncorrected nucleic acid count vs. nucleic acid concentration, showing a curve of the counted calf thymus DNA labeled with YOYO-1 that was localized to the Anopore membrane surface from an initial sample volume of 100 microliters. The curve count values correspond to the processed images depicted in FIGS. 12a-12h. The graph of FIG. 13 is an example of an uncorrected NAC assay calibration curve using the techniques described herein.

Figure 14:
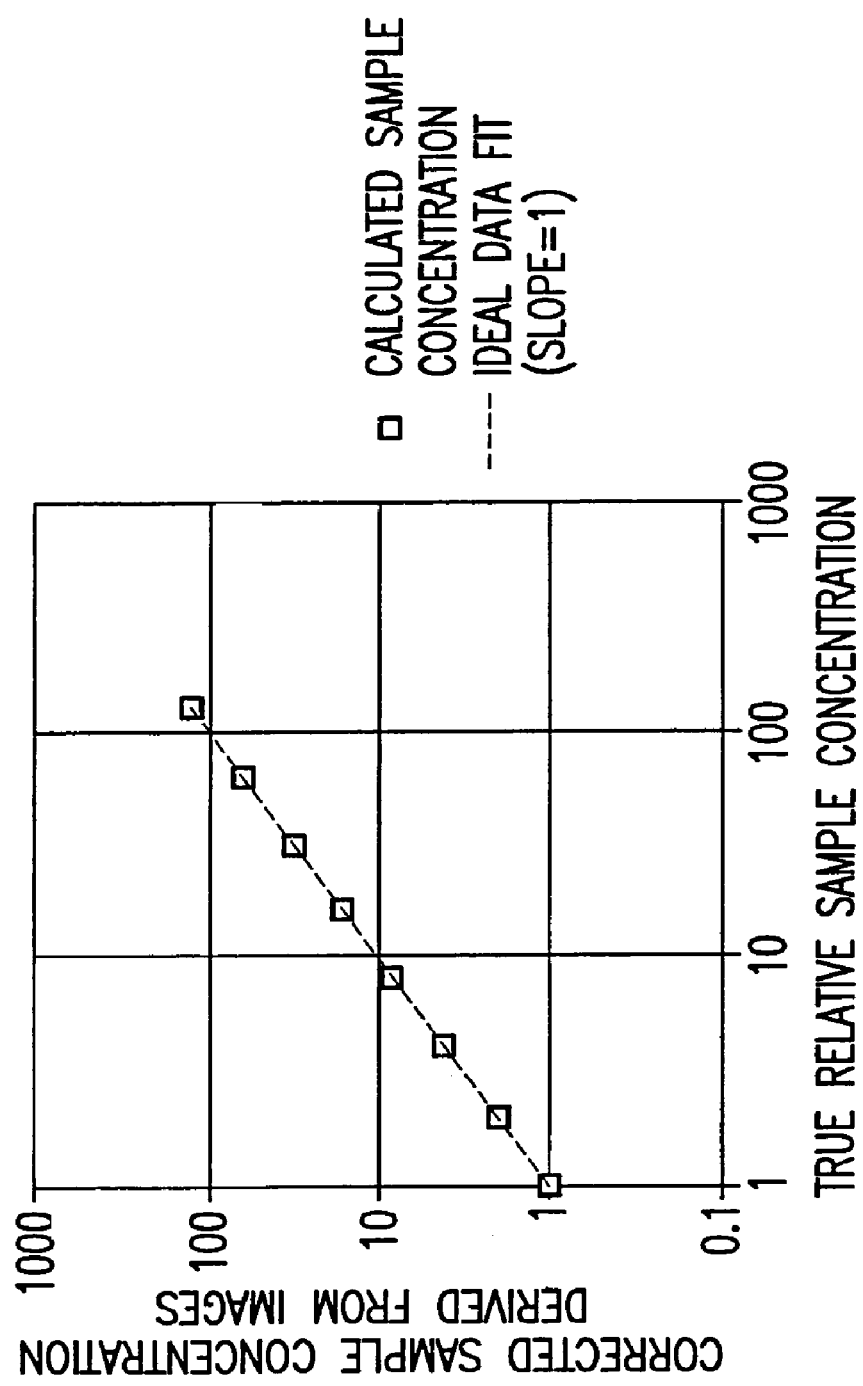
FIG. 14 is a graph showing the corrected nucleic acid count with respect to nucleic acid concentration.

FIG. 14 is a graph showing the corrected nucleic acid count with respect to nucleic acid concentration (i.e., corrected sample concentration derived from images vs. true relative sample concentration) derived from FIG. 13 and corrected for detector and immobilization efficiency.

D. Destabilization and Manipulation of Localized Analytes

In one aspect, once the analyte is localized on the microporous material or substrate, the localized analyte can be destabilized for further manipulation. The term "destabilized" as used herein is defined as any process that weakens the interaction between the analyte and the surface of the microporous material or substrate so that the localized analyte becomes more accessible for chemical manipulation. Typical interactions that can occur between the analyte and the microporous material or substrate include, but are not limited to, ionic or charged-charged interactions, hydrophobic/hydrophilic interactions, and mechanical/physical entanglement of one or more analytes. Varying degrees of destabilization of the analyte are possible, and will vary depending upon the analyte, the microporous material/substrate, and destabilizing technique that is employed. For example, destabilization of the analyte can completely remove the localized analyte from the microporous material and solubilize the analyte. Alternatively, a portion of the analyte can be destabilized while another portion of the analyte can interact with the microporous material.

In one aspect, described herein are methods for detecting an analyte involving the steps
(a) passing a fluid sample containing the analyte through or into a microporous material, wherein the analyte is localized near the surface of the microporous material;
(b) destabilizing at least some of the localized analyte; and
(c) detecting the destabilized analyte.

Any of the analytes, microporous materials, suspension matrices, and detection techniques described above can be used in this aspect.

In one aspect, the destabilizing step includes (1) contacting the localized analyte with a base; (2) agitating the localized analyte; (3) heating the localized analyte; (4) contacting the localized analyte with one or more ionic species; (5) contacting the localized analyte with one or more enzymes; (6) applying an electrical charge or ionizing energy to the localized analyte; (7) contacting the localized analyte with an organic solvent, or a combination of any of the steps above. It is contemplated that the destabilization step can involve one of the techniques described above or two or more techniques that are performed concurrently/simultaneously or sequentially.

In one aspect, the destabilizing step involves contacting the localized analyte with a base. In one aspect, the base has a pH of greater than 9. In another aspect, the base has a pH of 9 to 14, 9 to 13, 9 to 12, or 10 to 12. Any base known in the art can be used in this aspect. Examples of bases include, but are not limited to, an inorganic base or a buffer. In one aspect, the base can be NaOH, tris, carbonate/bicarbonate, and the like.

In another aspect, the destabilizing step involves agitating the localized analyte. The term "agitating" as defined herein includes any technique for destabilizing the localized analyte by physical force. Examples of techniques useful for agitating the localized analyte include, but are not limited to, sonication, vortex mixing, or pumping.

In a further aspect, the destabilizing step heating the localized analyte above 25° C. In another aspect, the localized analyte is heated from 60° C. to 100° C. In one aspect, the microporous material or substrate containing the localized analyte is submersed in a solution followed by heating the solution.

In another aspect, the destabilizing step involves contacting the localized analyte with one or more ionic species. Any ionic species known in the art can be used herein. Depending upon the analyte to be destabilized, the ionic species can be positively or negatively charged. Not wishing to be bound by theory, it is believed that the ionic species compete with the localized analyte for binding sites present on the microporous material or substrate. In one aspect, when the analyte is a nucleic acid, examples of ionic species useful herein include, but are not limited to, phosphate ions, borate ions, or a combination thereof.

In another aspect, the destabilizing step involves contacting the localized analyte with one or more enzymes. The selection of the enzyme will vary depending upon the localized analyte. In one aspect, when the analyte is a nucleic acid, the enzyme can be a restriction endonuclease, a nick enzyme, or a helicase.

Other methods for destabilizing a localized analyte involve contacting the localized analyte with an organic solvent that can solubilize a portion or all of the analyte. For example, a hydrocarbon solvent can be used to destabilize a hydrophobic analyte. In another aspect, when a suspension matrix is localized on the microporous material or substrate, an organic solvent can destabilize the suspension matrix as well.

Alternatively, in another aspect, an electric current can be applied to a microporous material or substrate containing the localized analyte in order to destabilize the analyte. For example, electrodes can be attached to the microporous membrane and an electrical charge can be applied. In another aspect, ionization energy can be used to delocalize the analyte. The amount of charge or energy that is applied can vary depending upon the localized analyte. By varying the amount of current or energy, it is contemplated that the degree of destabilization can be varied as well.

Once the analyte has been destabilized, the destabilized analyte can be chemically manipulated using any of the techniques described above. In one aspect, when the destabilized analyte is a nucleic acid, the destabilized nucleic acid can be detected, isolated, purified, and/or identified using any of the techniques described above. In one aspect, the destabilized analyte can be detected by amplification and hybridization. It is believed that after the destabilization step, the destabilized analyte is more accessible for manipulation. Thus, the detection and identification of the analyte such as a nucleic acid can be greatly enhanced compared to an analyte that is localized and not destabilized.

In one aspect, when the analyte is a nucleic acid, the detection of the destabilized nucleic acid by PCR amplification is from 5 to 75%, 10 to 60%, or 20 to 50% higher than the localized nucleic acid. For example, PCR amplification of localized nucleic acids is approximately 1-5% as efficient as fully dissolved nucleic acid, but this figure jumps to approximately 10-20% when destabilization reagents composed of, for example, Tris(tris (hydroxymethylaminomethane) (pH 11) are used. Not wishing to be bound by theory, it is believed the localized nucleic acid is not being eluted from the membrane surface into solution directly by the destabilization reagent, but can improve PCR amplification efficiency by either allowing the localized nucleic acid to enter solution under PCR thermal cycling conditions or simply improving reagent access to the localized nucleic acid.

In another aspect, mild ultrasonic mixing of destabilization reagent results in the PCR amplification efficiency jumping from approximately 10% (without sonication) to over 50% with sonication. In another aspect, the combination of pH and ultrasonic mixing causes a measurable amount of localized nucleic acid to destabilize.

In one aspect, a suspension matrix is localized on the surface of the microporous material prior to contacting the microporous material with the analyte. In this aspect, the analyte can then be localized on the suspension matrix. Upon destabilization, the suspension matrix and/or the localized analyte can be destabilized. In one aspect, when DNA is used as the suspension matrix, the matrix can be destabilized for improved detection. Alternatively, the suspension matrix can be mixed with the analyte prior to localization on the microporous substrate.

In another aspect, a method for detecting a nucleic acid involves
(a) contacting a fluid sample comprising the nucleic acid with a surface, wherein the nucleic acid is localized near the surface;

(b) destabilizing at least some of the localized nucleic acid; and (c) detecting the destabilized nucleic acid.

The surface in this aspect, the surface can be any material that can form an interaction with the analyte that is capable of being destabilized using the methods described herein. Examples of surfaces include, but are not limited to, glass, plastic, metals, ceramics, a microporous material described herein, and the like.

E. Articles and Kits

Any of the microporous materials and composites described herein can be part of a filtration device. The phrase "filtration device" as referred to herein is defined as any device that contains at least one microporous material described herein.

Figure 15A:
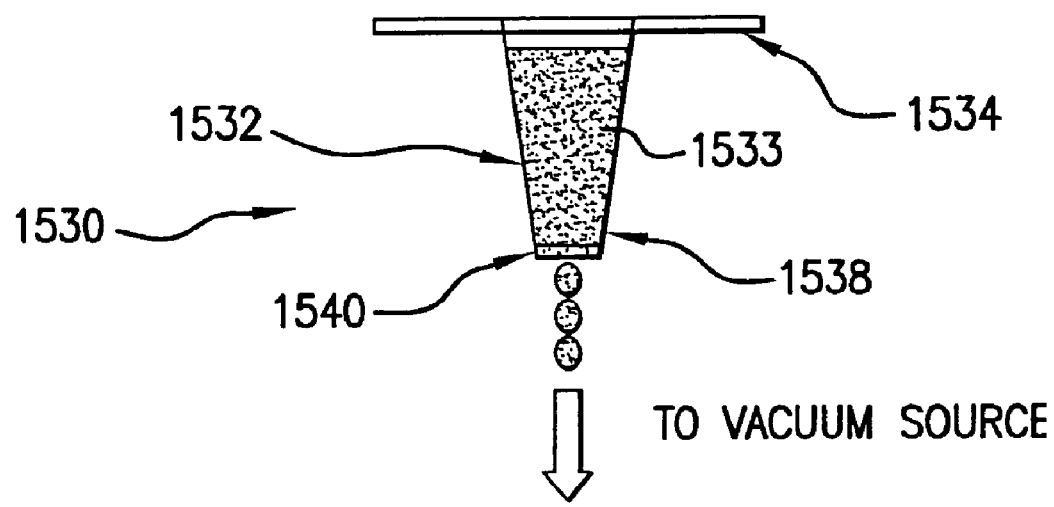
FIG. 15a depicts a filtration device for the localization of an analyte.

In one aspect, a filtration device is depicted in FIG. 15a. A filter assembly 1530 includes a well 1532 for holding a test sample 1533 containing an analyte. While only one well is shown in FIG. 15a, it should be understood that a plurality of wells can be used that are part of a filter plate 1534, which can have a multiwell format, such as a 96 or 384 well filter plate. A bottom opening 1538 of well 1532 is covered with a microporous material 1540 for analyte localization. In one aspect, a 0.2 micron Anopore membrane filter can be heat fused to a bottom portion of well 1532. The bottom opening 1538 is in fluid communication with a vacuum source (not shown), which can provide a differential of about 5-10 psi to aid in filtering test sample 1533 through analysis filter 1540. In addition, analysis filter 1540 may be configured for optical molecular detection of analyte. For example, analysis filter 1540 can be removably attached to a bottom portion of well 1532, to allow removal of filter 1540 for use in an optical detection system. Additionally, filter assembly 1530 may be designed, in conjunction with a suitable detector, to permit optical molecular detection on analysis filter 1540 without removal.

Figure 15B:
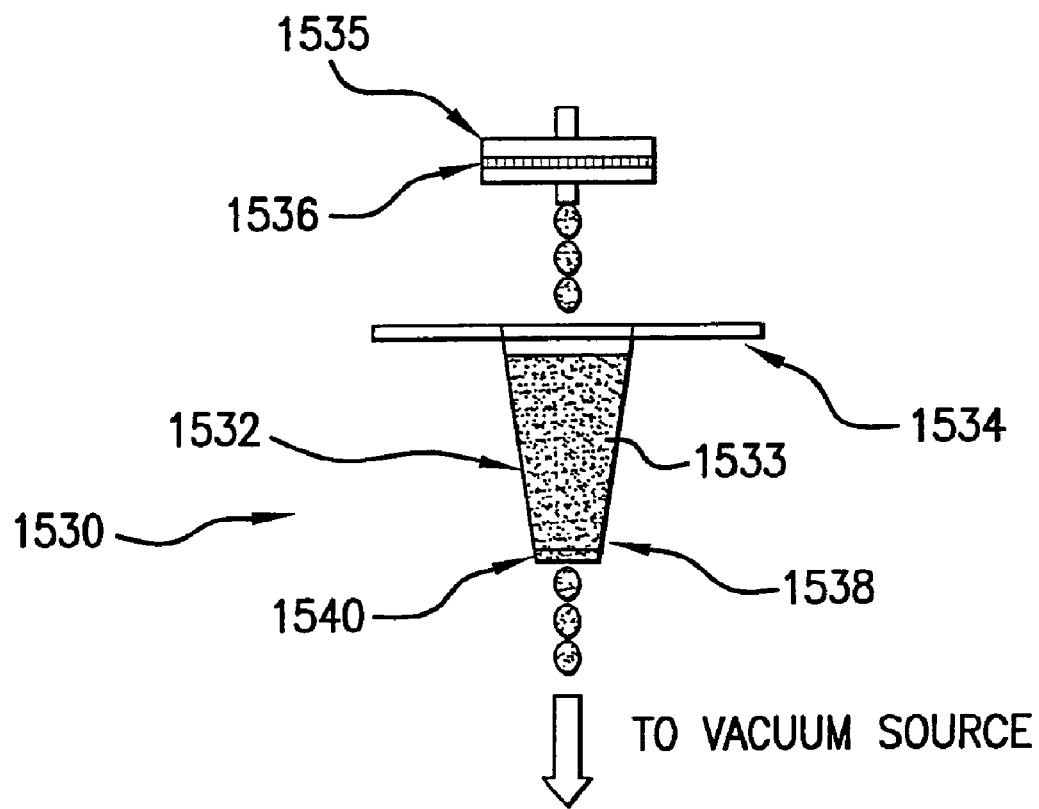
FIG. 15b is a schematic depiction of a filter system.

In another aspect, FIG. 15b is a schematic depiction of a filter system that employs filter assembly 1530 with prefiltration according to an alternative embodiment. As depicted in FIG. 15b, filter assembly 1530 can be used in conjunction with a prefiltration device 1535, such as a syringe type filter (shown) or filter plate (fixed or removable, not shown). The prefiltration device 1535 contains a prefilter 1536 that is configured to retain contaminants or impurities larger than the micropores in prefilter 1536, while allowing particles containing analytes in the fluid to pass through the first filter. In one aspect, when the analyte is a nucleic acid, the nucleic acid can include virions, bacteria, spores, and the like. The prefilter 1536 can be a surface filter such as a membrane filter, or prefilter 1536 can be a depth filter.

During use, test sample 1533 is filtered through prefilter 1536 into well 1532. Additional reagents, such as virion lysing agents, dyes, buffers, etc., may be added to the filtered test sample in well 1532. The filtered test sample is incubated and then filtered through analysis filter 1540 to effect nucleic acid capture and localization.

In one aspect, filter assembly 1530 is a rapid viral load assay, such as in testing for HIV, hepatitis C, or other infectious diseases. In this aspect, only the infectious virion particles are to be counted. That is to say, many virus-like particles are empty of nucleic acid and are noninfectious. Likewise, freely circulating viral nucleic acid (unencapsulated) is also noninfectious. In using the filter system shown in FIG. 15b, intact, unlysed virions will pass through prefilter 1536, while larger impurities and free nucleic acids will be retained. The filtrate virions in well 1532 are then treated to release nucleic acids for capture on analysis filter 1540, while proteins, viral capsule debris, other small impurities, etc. will pass through filter 1540. The only nucleic acids captured on analysis filter 1540 are those that were contained within intact virions. This way, only infectious virions are counted.

For example, an analysis of HIV viral load may be performed with filter assembly 1530 as part of a high sensitivity assay that requires approximately 200 µl patient samples to capture sufficient nucleic acids to be statistically meaningful. In order to obtain such a sample, a 200 µl human plasma sample is prefiltered using prefilter 1536, as shown in FIG. 15b, to remove large impurities and free nucleic acids. An intact HIV virion is known to be approximately 0.1 microns in diameter and will pass through a 0.2 micron prefilter. The prefiltered sample is then processed in well 1532 to lyse the virions to release viral RNA, and the viral RNA is then captured on analysis filter 1540 according to the disclosed methods. Alternatively, the prefiltered sample can be deposited into a sterile, clean container (not shown), and then accurately pipetted along with lysing reagents, etc. into well 1532. The viral RNA localized onto the surface of filter 1540 can then be subjected to analysis such as optical molecular counting or conventional PCR type analysis.

In one aspect, the filtration device is composed of a well body having an inlet and an outlet, wherein the well body has an inner wall and outer wall, and (b) a filter composed of any of the microporous materials including composites and modified-microporous materials described herein, wherein the filter is attached to the inner wall of the well body. In one aspect, the filter can be attached to the inner surface of the well body directly with an adhesive. In another aspect, the filter can be attached to the inner surface of the well body by with the use of a filter holder. In one aspect, the well body is composed of any material that is chemically inert and that can be subjected to heat without altering the dimensions or structure of the well body. In one aspect, the well body is composed of a plastic such as polypropylene.

Once the sample containing the analyte is passed through the inlet of the well body, contacted with the filter and the analyte is localized near the surface of the microporous material, and the remaining solution is passed through the filter and exits the outlet, the localized analyte can be further manipulated. In one aspect, the inlet and outlet of the well body can be receptive to a cap or seal. For example, the inlet and/or outlet can be threaded to receive a screw-on cap. Alternatively, the inlet and/or outlet can contain edges or contours that permit a cap to be snapped on the inlet or outlet. In one aspect, the cap or seal can be any of the materials that the well body is composed of.

Figure 16A:
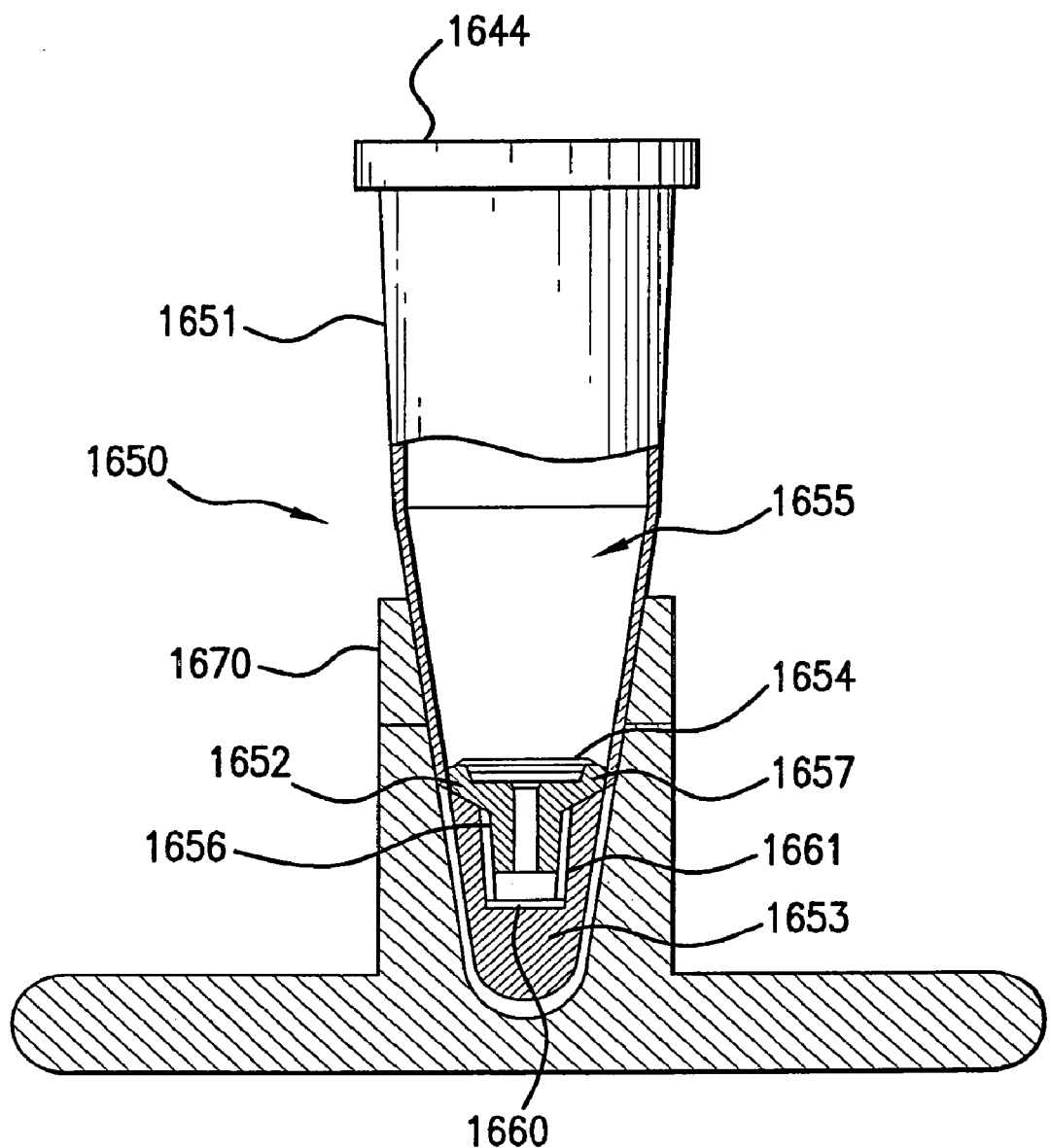
FIG. 16a depicts an alternate filtration device for the localization of an analyte.
Figure 16B:
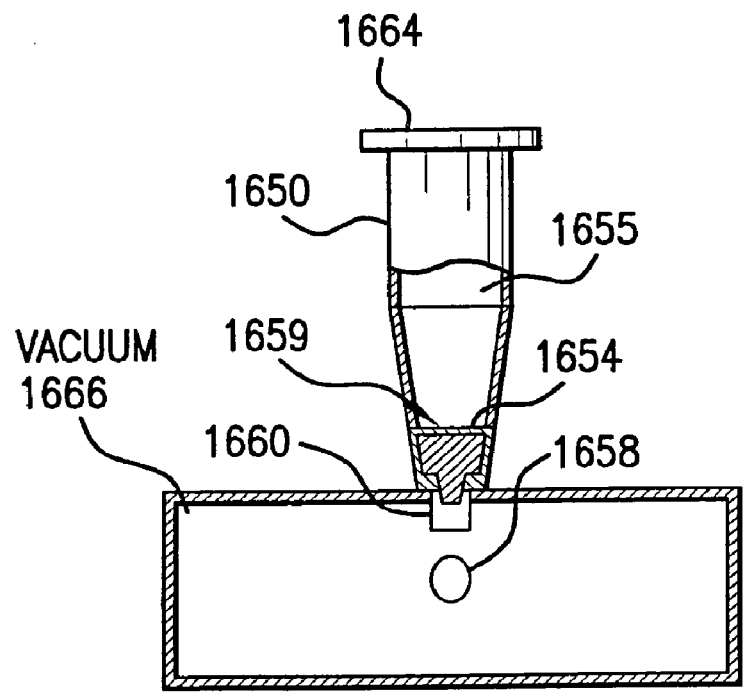
FIG. 16b depicts a filter assembly during use.

Several aspects of the filtration device described above are depicted in FIG. 16. In one aspect, FIG. 16a depicts a filter assembly, generally designated as 1650, designed to fit within a commercially available thermal cycler 1670. The filtration device is composed of well body 1651, filter holder 1652, and outlet cap 1653. Analysis filter 1654 is attached to filter holder 1652 by heat fusing or other means to ensure sample 1655 is filtered through analysis filter 1654 during operation. During assembly, filter holder 1652, including attached analysis filter 1654, is placed within well body 1651 and secured by mechanical interference between tapered surfaces generally shown as 1656. Alternatively, these surfaces may be adhesively bonded or otherwise affixed in a leak free manner. Clearance 1657 between well body 1651 and filter holder 1652 is allowed so as not impose undue stress on attached analysis filter 1654, but must be minimized to prevent sample contamination and carryover. During use, as shown in FIG. 16b, sample 1655 is placed in filter assembly 1650 and outlet cap 1653 has not been installed. Mild vacuum 1666, pressure, or centrifugal force is used to effect fluid flow of sample 1655 through analysis filter 1654. Filtrate 1658 flows from filter assembly 1650 to waste (not shown) through outlet 1660 while nucleic acids 1659 are retained on analysis filter 1654 for further processing. Localized analytes 1659 and analysis filter 1654 may be rinsed or otherwise processed at this point to minimize effects of NSB, carryover, etc. The outlet 1660 of relatively dry filter assembly 1650 containing analytes 1659 on analysis filter 1654 is capped with outlet cap 1653 (FIG. 16*a*) to prevent further fluid flow from the assembly during further processing. The fluid seal for outlet 1660 is affected by mechanical interference between tapered surfaces generally shown as 1661 present on outlet 1660 and outlet cap 1653. Other methods of sealing outlet 1660 known to those skilled in the art are also contemplated, such as valves, plugs, etc.

Figure 16C:
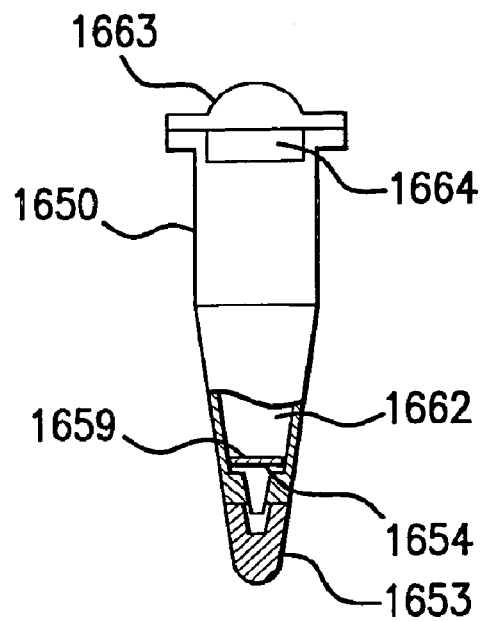
FIG. 16c shows filter assembly configured for further processing.

FIG. 16*c* shows filter assembly 1650 configured for further processing. For example, reaction reagents 1662 such as PCR master mix or hybridization reagents for nucleic acid labeling have been added and are in contact with nucleic acids 1659 on analysis filter 1654. Cap 1663 has been added to seal the top opening 1664 of filter assembly 1650. Alternatively, top opening 1664 may be sealed with film as is known to those skilled in the art. In this configuration, the assembly may be subjected to thermal cycling or other processes as required for conventional PCR, RT-PCR, hybridization, etc. processes for analysis. Additionally, this embodiment may be useful for other detection schemes such as molecular counting. In this case, well body 1651 may be shorter to accommodate certain detector optical designs. In all cases, however, the ability to retain liquids in contact with the membrane during processing by reversibly capping openings is important.

Figure 17A:
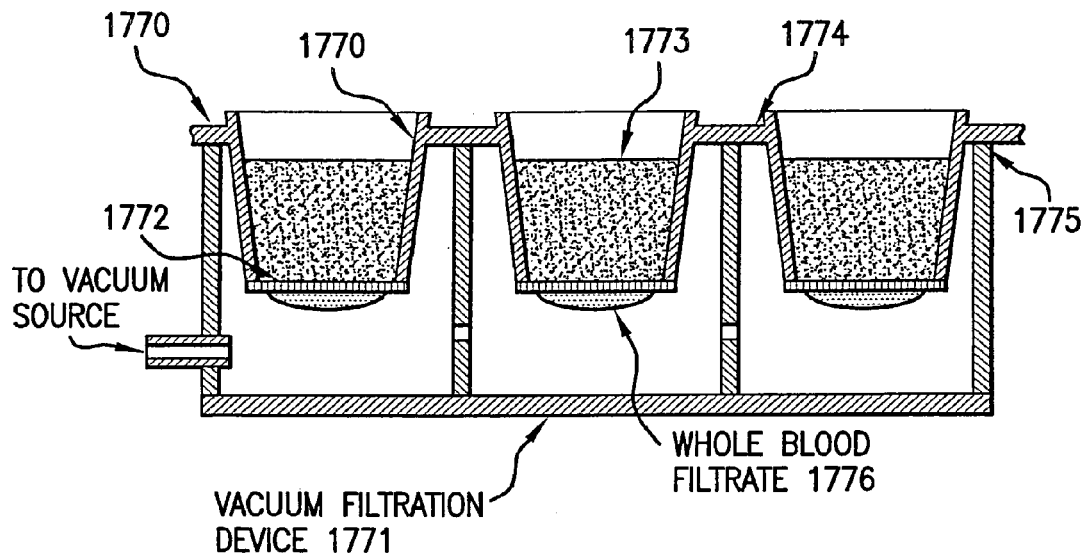
FIG. 17a depicts an alternate filtration device for the localization of an analyte.
Figure 17B:
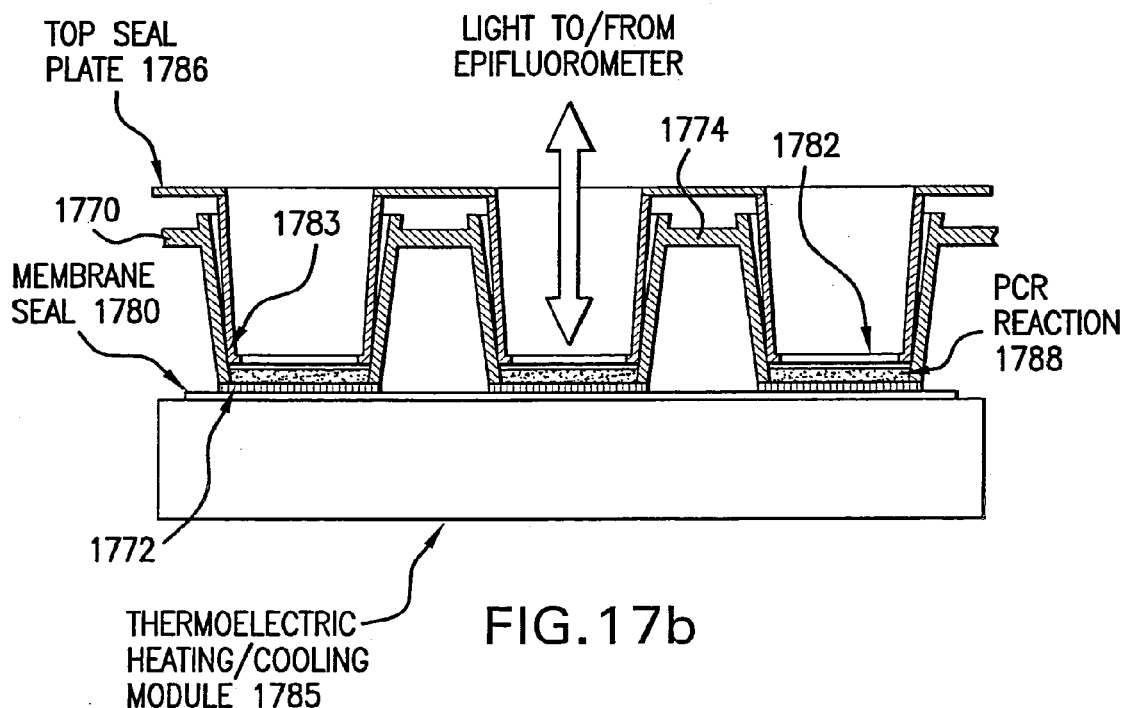
FIG. 17b shows filter assembly 1770 during RT-PCR processing.

Another filter assembly is shown in FIGS. 17*a* and 17*b*. This filter assembly, generally designated 1770, is designed to operate with flat surface heat transfer for thermal cycling rather than the well type format described for the filter assembly shown in FIG. 16. In one aspect, the microporous material is composed of aluminum oxide, which has excellent heat transfer properties compared to the walls of a plastic well as found on most PCR thermal cyclers. Accordingly, thermal cycling time improvements may be realized by providing a filter assembly and thermal cycler designed to transfer heat across the analysis membrane.

In another aspect, the filtration device contains two or more well bodies, wherein each well body has a top opening and a bottom opening, and (b) a filter composed of any microporous material described herein, including composites and modified-microporous materials, wherein the filter covers the bottom opening of each well body. FIG. 17 depicts certain aspects of this embodiment. The well body can be composed of any of the material described above.

FIG. 17*a* shows filter assembly 1770 during sample preparation installed in vacuum filtration device 1771. Alternatively, any device that facilitates the movement of fluid through the filter of the filtration device can be used in this embodiment. Examples of such devices include, but are not limited to, filtration by pressure, centrifugation, or fluidic pumping. Filter assembly 1770 is shown as a three well assembly, but generally may contain any number of wells. For instance, currently used multiwell plates frequently contain 96 or 384 separate wells. Filter assembly 1770 contains analysis filters 1772 attached by heat sealing or other means so as to allow for analyte localization to the filter surface during filtration as previously described. Solutions to be analyzed, in this case whole blood lysate 1773, are contained in the wells of filter assembly 1770. During vacuum filtration, a vacuum seal is established at vacuum sealing surface 1775. Filter assembly 1770 is shown with a compliant support plate 1774 that allows the assembly to deform under vacuum to affect a more uniform vacuum seal on vacuum sealing surface 1775. In one aspect, the vacuum causes whole blood lysate 1773 to filter through analysis filters 1772. In this aspect, nucleic acids present within the whole blood lysate 1773 are localized on the microporous material 1772, while whole blood filtrate 1776 traverses the analysis filters 1772 and eventually to waste (Not shown). As described in the previous examples, the analysis membranes 1772 may be rinsed prior to further processing.

FIG. 17*b* shows filter assembly 1770 during RT-PCR processing. In this aspect, prior to processing, the disposable wells can be sealed to prevent leakage, contamination, and evaporation. The analysis filter 1772 can be sealed as shown with a sheet of thin (1 mil) plastic, either by adhesive bonding (sticky film) or by heat sealing to the membrane or the housing around the membrane periphery as shown as membrane seal 1780. This membrane should be thin to allow rapid heat transfer through the combined sealing/filtration membranes. In one aspect, heat transfer analysis indicates the thermal resistance of the Anopore filter is negligible compared to typical sealing films. Nevertheless, even employing conventional plastic sealing materials (polypropylene films, etc), this thermal resistance is less than the glass capillaries used in the Lightcycler RT-PCR instrument (Roche), and many times less than plastic well based thermal cyclers. Prior to filtration membrane sealing, an optional clean blotting step can be performed to remove any hanging filtrate drops or liquid. This may be advantageously accomplished with disposable blotting material (not shown), where the filtration assembly 1770 is removed from the vacuum filtration device 1771, quickly blotted against a disposable blotting surface (for instance blotting paper) then membrane sealed either with adhesive or thermal sealing membranes.

In this aspect, the top opening of the disposable wells can be sealed. Additionally, sealing should be accomplished so as to allow optical detection of the reactions. A top seal plate 1786 is shown in FIG. 17*b* as a separate molded piece containing an integral thin optical window 1782 for optical analysis. Although shown in gray with transparent windows, the top seal plate can be composed of a clear low fluorescent material with integral windows. As shown, the top seal plate 1786 forms a seal 1783 with filter assembly 1770 within the well just above the PCR reaction 1788 liquid level. During thermal cycling, PCR reaction 1788 solution temperature must be homogenous (isothermal), liquid evaporation must be minimized to maintain consistent reaction conditions, and condensation should be controlled on the optical window 1782 to allow accurate optical measurements. Accordingly, the distance between the PCR reaction 1788 liquid surface and optical window of the seal plate 1786 should be minimized consistent with ease of use, materials of construction, and desired heat and mass transfer conditions of the optical window to minimize condensation.

Referring to FIG. 17*b*, thermal cycling is accomplished by direct conductive heat transfer through the membrane seal 1780/analysis filter 1772 from a thermoelectric module 1785 operated in a temperature sensing feedback loop. That is to say, a thermoelectric module 1785 (TEM, peltier heater/cooler) is in intimate contact with the membrane seal 1780 with no intervening circulating air or water baths, dead air gaps associated with slip fits into aluminum block heaters, etc. Thermal contact is improved by using a compliant multiwell plate design, in that the compliant support plate 1774 of filter assembly 1770 has sufficient deformability to allow the bottom membrane seal 1780 to conform to the flat surface of the thermoelectric heating/cooling module 1785. In this way, excellent thermal performance with better accuracy and speed compared with existing thermal cycling equipment is anticipated.

An embodiment of FIG. 17b is shown in FIGS. 18 and 19. In these embodiments, filtration device comprises (a) a plate having a first surface and a second surface, wherein the plate has at least one hole, wherein the hole has a fixed width at the first surface and the second surface of the plate, and (b) a microporous material having a first surface and a second surface, wherein the first surface of the microporous material is adjacent to the second surface of the plate, wherein the microporous material covers each hole in the plate. The term "adjacent" as referred to herein is defined as the plate and any microporous material described herein that are in physical contact with one another. The term "adjacent" also refers to the plate and microporous material that is separated by another material. For example, a prefilter can be placed between the plate and the microporous material.

Figure 18A:
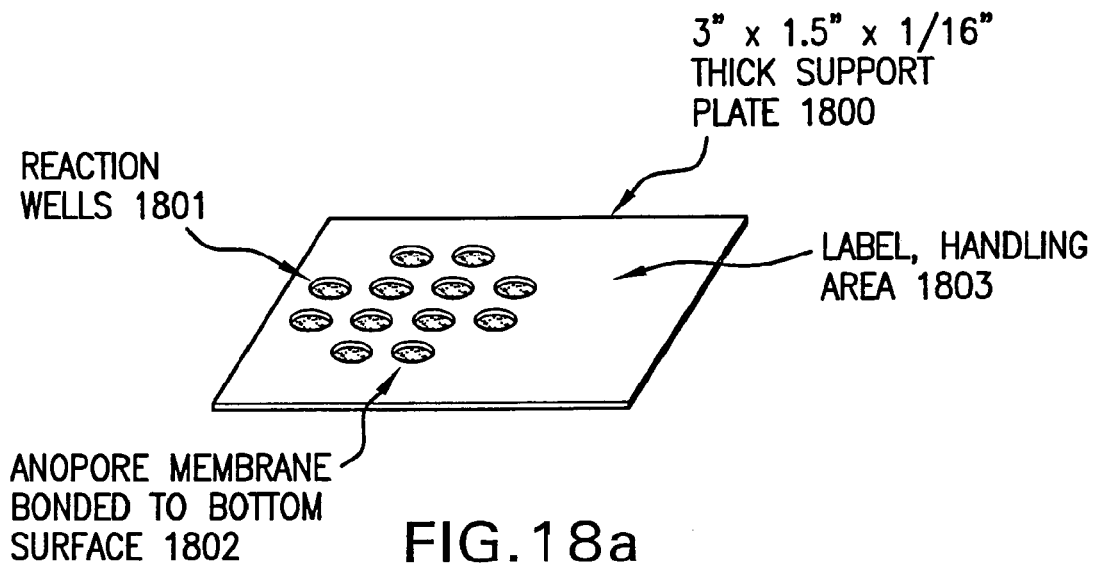
FIG. 18a depicts an alternate filtration device for the localization of an analyte.
Figure 18B:
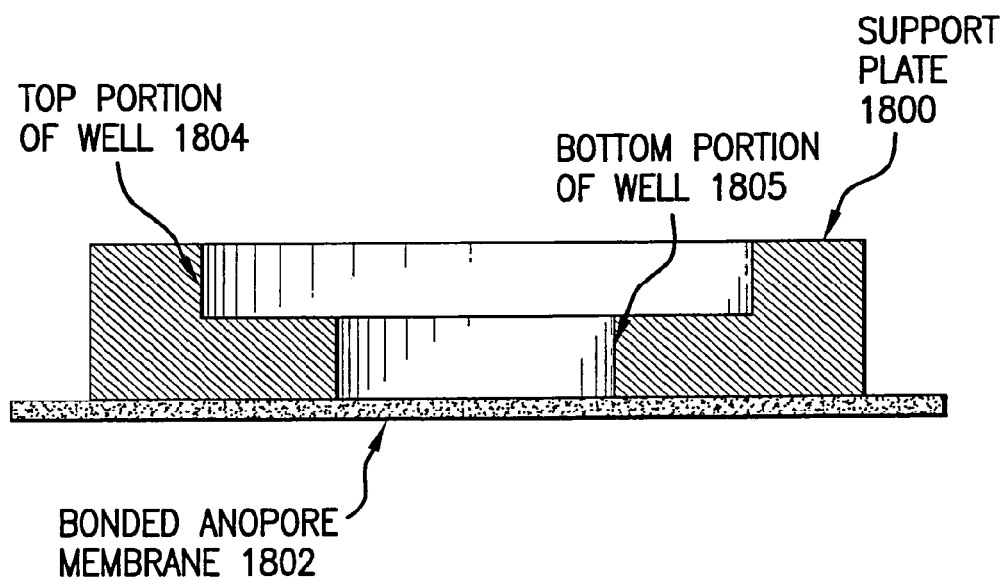
FIG. 18b depicts an alternate filtration device for the localization of an analyte.
Figure 19A:
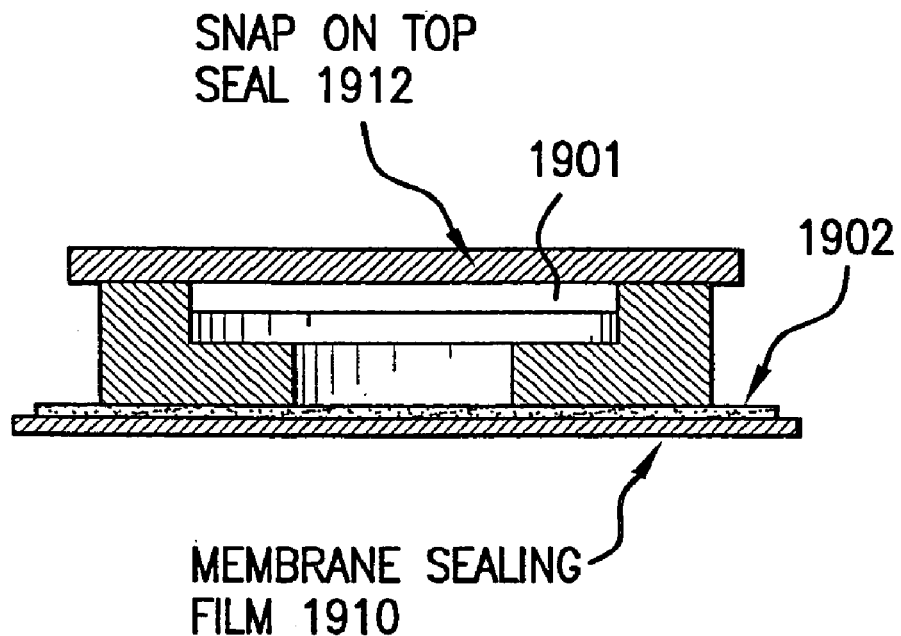
FIG. 19a depicts an alternate filtration device for the localization of an analyte.
Figure 19B:
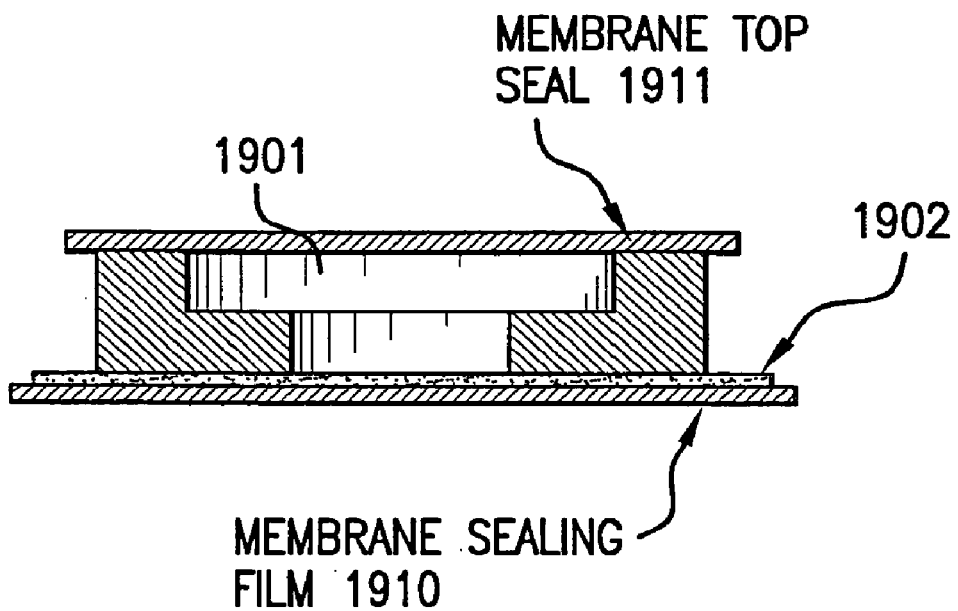
FIG. 19b depicts an alternate filtration device for the localization of an analyte.

In FIG. 18, plate 1800 is composed of any material that possesses rigidity, low fluorescence, ease of manufacture, and thermal conductivity. In one aspect, the plate is composed of anodized aluminum or plastic. In FIG. 18a, 12 reaction wells 1801 have been formed through plate 1800; however, any number of holes, including only one hole, can be present in the plate. In one aspect, Anopore membrane 1802 has been bonded to the bottom surface of plate 1800, thereby forming the bottom of the reaction wells 1801. The membrane may be bonded with liquid adhesives such as epoxy, acrylic, etc. or with adhesive tapes. The microporous material covers each hole in the plate. Referring to FIG. 18b, the wells may have a larger top portion 1804 and a smaller bottom portion 1805 to aid in optical detection, sealing, liquid handling, etc. In one aspect, the larger top portion 1804 can receive a prefilter that can remove impurities. An analyte containing sample is filtered and rinsed through the microporous material, thereby localizing the analyte for further processing and detection. In one aspect, referring to FIG. 19a, when the analyte is a nucleic acid, the dried bottom surface of the microporous material 1902 containing localized analyte can be sealed by heat welding polypropylene heat sealing film 1910 directly onto the dry membrane. Reaction liquid 1913 such as, for example, PCR master mix, can then added into wells 1901. The tops of wells 1901, containing the reaction liquid 1913 can then be sealed by clear adhesive tape 1911 (FIG. 19b) or clear snap-on top 1912 (FIG. 19a). This assembly can then processed as described in, for example, FIG. 17.

Figure 20:
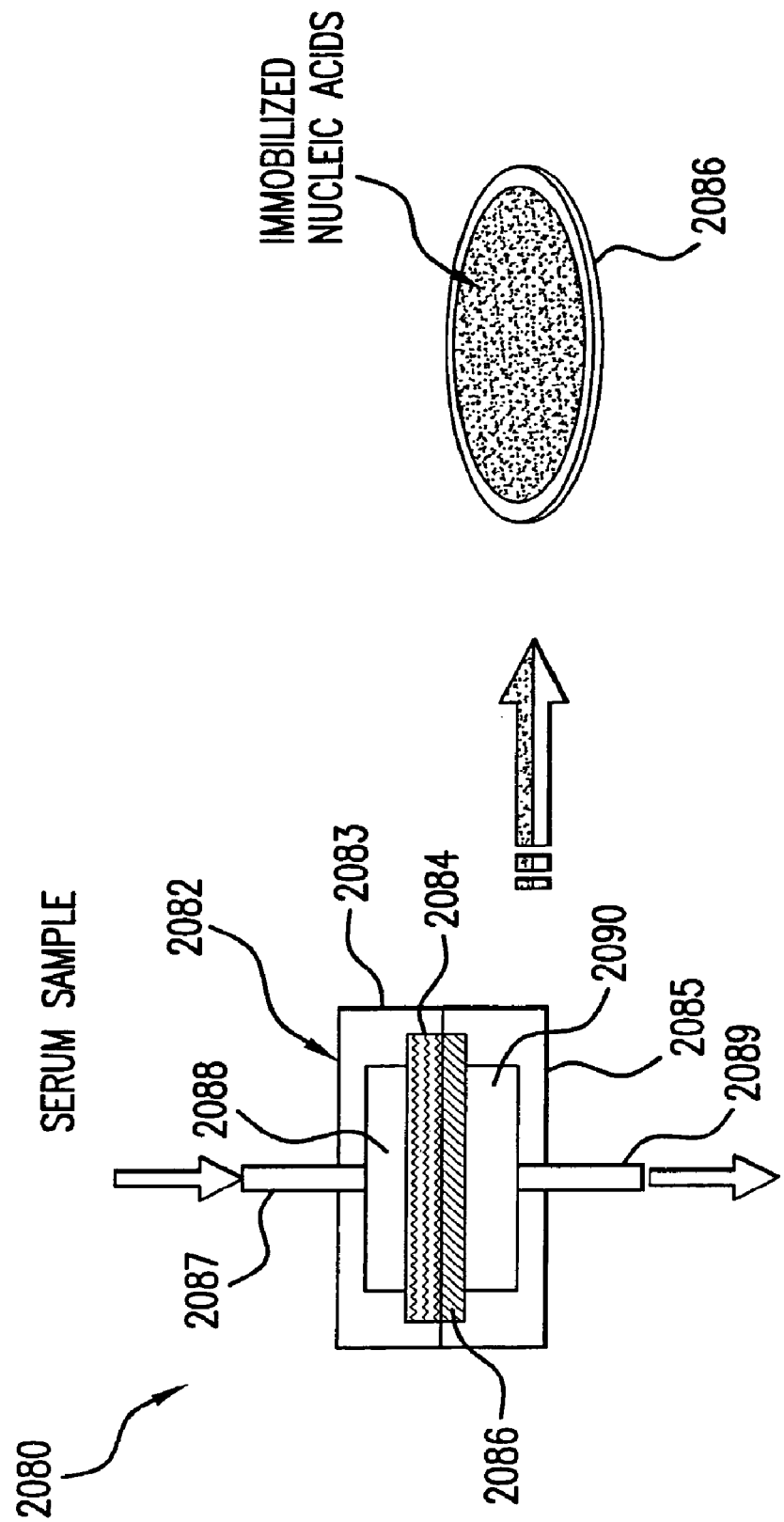
FIG. 20 depict an alternate filtration device for the localization of an analyte.

In another aspect, the microporous material used for concentration and localization of nucleic analytes can be part of a cascade filter assembly 2080 in FIG. 20. The filter assembly 2080 includes a removable housing 2082 for receiving a sample containing the analyte. A first portion 2083 of housing 2082 is configured to contain a first filter 2084, such as a 0.2 micron Anopore membrane filter for prefiltering the test sample. A second portion 2085 of housing 2082 is configured to contain a second filter 2086 for analyte localization, such as a 0.2 micron Anopore membrane filter. The filters 2084 and 2086 are arranged in an in-line filter type configuration within housing 2082 such that filter 2084 is adjacent to and precedes filter 2086. A sample entrance tube 2087 is in fluid communication with a first chamber 2088 in first portion 2083, and an exit tube 2089 is in fluid communication with a second chamber 2090 in second portion 2085 of housing 2082.

In one aspect, during use of filter assembly 2080, a preprocessed patient sample such as a serum sample is deposited through tube 2087 into chamber 2088 and onto filter 2084. As the sample flows through filter 2084 and then filter 2086, nucleic acids are localized to the surface of filter 2086. As shown in FIG. 20, filter 2086 including the captured nucleic acids can then be physically removed from housing 2082 for further processing and/or optical nucleic acid counting such as described hereafter.

Figure 21:
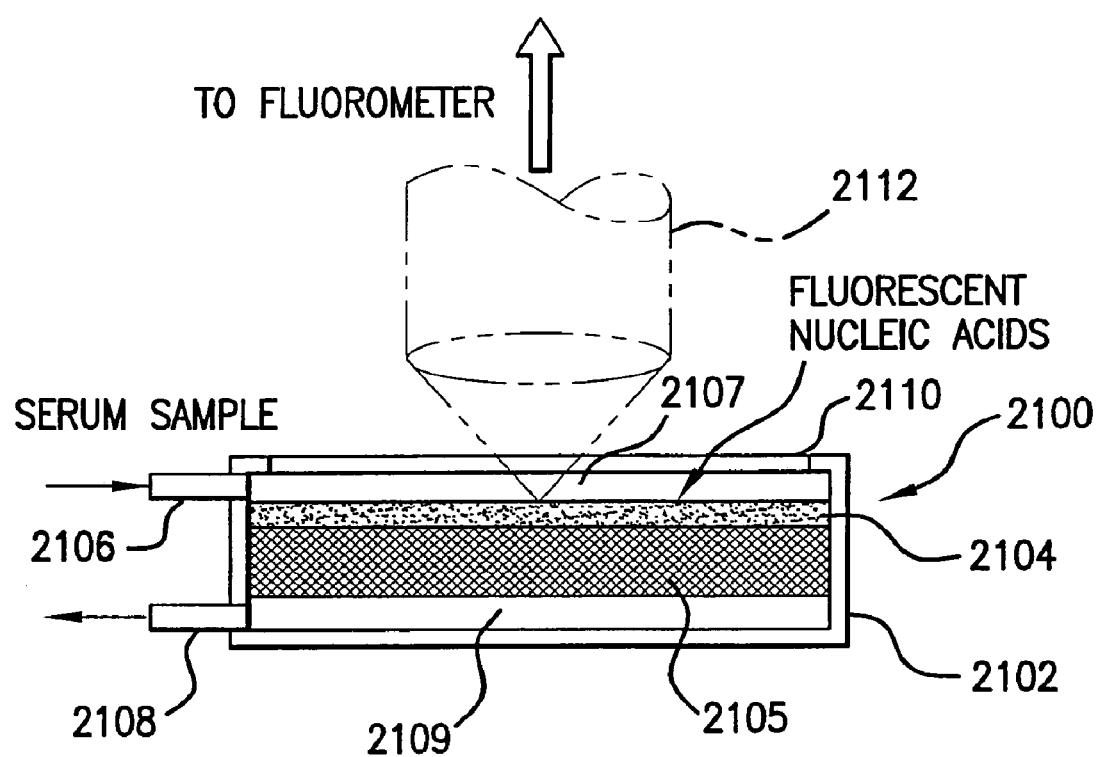
FIG. 21 depict an alternate filtration device for the localization of an analyte.

In a further embodiment, the membrane filter used for concentration and localization of analytes can be part of a flowcell filter assembly 2100 as depicted in FIG. 21. The flowcell filter assembly 2100 includes a housing 2102 for receiving a sample or other sample containing the analyte. The housing 2102 is configured to hold an analysis filter 2104. In one aspect, the analysis filter 2104 is a 0.2 micron Anopore membrane filter for nucleic acid localization. The filter 2104 rests on an optional porous filter support 2105. If filter 2104 has a sufficiently small diameter, then porous filter support 2105 may be omitted. An entrance tube port 2106 is in fluid communication with a first chamber 2107 adjacent to filter 2104, and an exit tube port 2108 is in fluid communication with a second chamber 2109 adjacent to filter support 2105 in housing 2102. An optical window 2110 is located on a surface of housing 2102 to allow transmission of light 2112 to and from a detector (not shown) to the surface of filter 2104. The light 2112 is operatively connected to a detector such as a fluorometer (not shown).

During use of flowcell filter assembly 2100, a sample is injected through tube port 2106 into chamber 2107 and onto filter 2104. As the sample flows through filter 2104, analytes are localized on the surface of filter 2104. In one aspect, when the analyte is a nucleic acid, the nucleic acids in the sample are labeled prior to injection of the sample into flowcell filter assembly 2100. However, the nucleic acids can be labeled after localization to the surface of filter 2104. In this aspect, the nucleic acids on filter 2104 may be counted in flowcell filter assembly 2100 through optical window 2110 by use of a fluorometer simultaneously with sample fluid flow and filter membrane processing. This potentially improves nucleic acid detectability thru better background signal rejection. Sample prefiltering, if required, is done prior to injection of the sample into flowcell filter assembly 2100. Ports 2106 and 2108 may be capped or otherwise constricted to allow further processing of the localized nucleic acids, such as hybridization, PCR reactions, etc. to occur.

Figure 22:
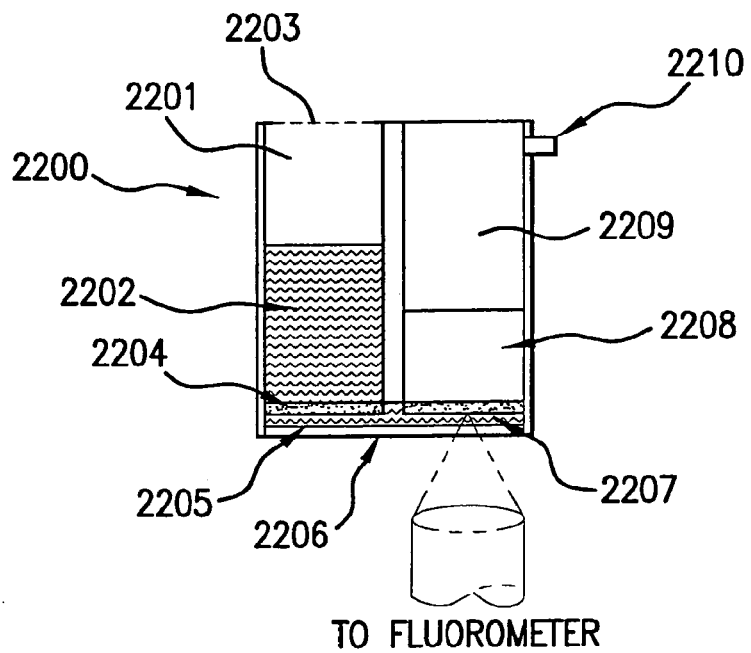
FIG. 22 depict an alternate filtration device for the localization of an analyte.

FIG. 22 shows a modification of a generalized well type format that provides for particulate prefiltration immediately prior to analyte localization. In some cases, environmental dust, mold, bacteria, etc. may settle into the well containing the analyte sample to be analyzed and create erroneous signals for analyte counting. A filter assembly to minimize this effect is designated generally as 2200. The filter assembly 2200 has a housing defining a first chamber 2201 having an opening 2203, which allows deposition of an analyte sample 2202 within chamber 2201. The bottom of chamber 2201 contains a prefilter 2204, which is selected so as to retain particles larger than about 0.2 microns and pass the analytes. Below prefilter 2204 is a fluid passageway 2205 that conveys a prefiltered analyte sample to an analysis filter 2207, which is disposed in the housing at one end of a second chamber 2209. At least part of one surface of passageway 2205 is defined by an optical window 2206, which allows the surface of analysis filter 2207 in fluid communication with passageway 2205 to be detected.

During use of filter assembly 2200, analytes contained within sample 2202 are localized on analysis filter 2207 as the sample flows thru filter 2207 to form liquid waste 2208 located in chamber 2209. A vent port 2210 may be connected to a vacuum source to aid and control fluid flow, or chamber 2201 may be slightly pressurized as is well known to those skilled in the art. The waste 2208 may be contained within chamber 2209 as shown, or may be removed from chamber 2209 to a central waste container (not shown). The filter assembly 2200 may be used with additional prefiltration as described herein to remove intrinsic nucleic acids, particles, and other impurities prior to sample processing (e.g., virion lysis, etc.) in chamber 2201. The filter 2204 simply removes potentially interfering particulate immediately prior to nucleic acid immobilization on filter 2207.

Figure 23A:
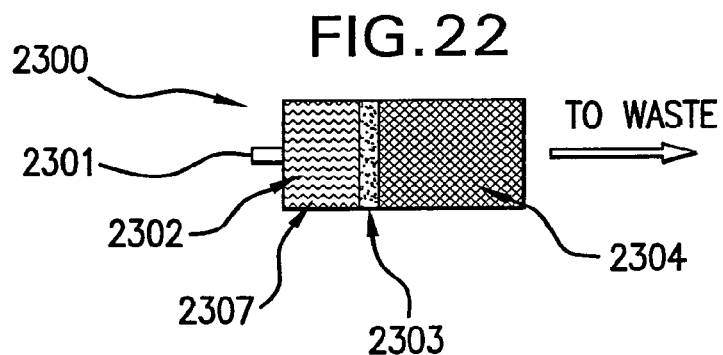
FIG. 23a depicts an alternate filtration device for the localization of an analyte.
Figure 23B:
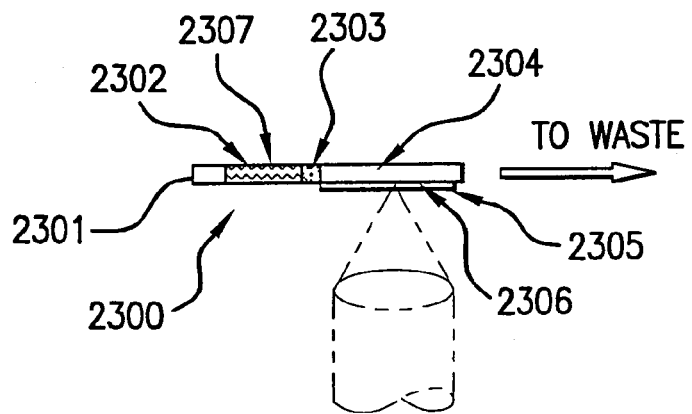
FIG. 23b depicts an alternate filtration device for the localization of an analyte.

FIGS. 23*a* and 23*b* depict a flowcell device for analyte counting with greatly reduced diffusion distance, which can be used with solid surface (non-filter) localization. Low concentrations of analytes require considerable time to diffuse to solid surfaces. FIG. 23*a* shows a plan view and FIG. 23*b* shows a side view of a solid surface localization flowcell device 2300. The flowcell device 2300 has an inlet tube 2301 for introduction of an analyte containing sample 2302 into an inlet chamber 2307 defined by a first portion of a housing. At least part of one wall of chamber 2307 is formed by a flow distribution structure 2303, which is between chamber 2307 and a localization passageway 2304 defined by a second portion of the housing. Referring to FIG. 23*b*, at least one of the major surfaces of the second portion of the housing defining localization passageway 2304 is composed of an optical window 2305. In addition, the interior of at least one of these major surfaces has been treated to localize the analyte from the sample as a localization surface 2306. The localization surface 2306 can be on optical window 2305, on a surface opposite optical window 2305, or on both.

The distribution structure 2303 is generally composed of a porous material providing sufficient pressure drop to cause substantially uniform flow downstream in localization passageway 2304. Under certain circumstances, flow distribution structure 2303 may be configured as a narrow opening into localization passageway 2304. The localization passageway 2304 is generally of flat construction with dimensions of about 1 to about 10 mm width and length, and a thickness of about 10 to about 50 microns. That is to say, the analyte containing sample 2302 flows through a passage about 1 to about 10 mm wide, about 10 to about 50 microns high, and about 1 to about 10 mm long.

During operation of flowcell device 2300, the analyte containing sample flows into the device, where it is uniformly introduced into localization passageway 2304. As the sample slowly flows through this passageway, analytes are localized onto localization surface 2306 relatively rapidly due to the very small diffusion distance (about 10-50 microns) afforded by the passageway height. The remaining fluid passes out of localization passageway 2304 as waste. Localized analyte is then optically detected on surface 2306. This flowcell device 2300 can be configured with gravity, pressure, or vacuum flow control, and may be part of a disposable device. Additionally, flowcell device 2300 can be configured to process samples remotely from an optical detector for an extended period. Such samples are then quickly optically analyzed after localization is complete.

Any of the articles and filtration devices described above can be incorporated into a kit. The kit also includes any of the detection means described above for detecting the localized analyte. In one aspect, an optical detector is used to detect a labeled nucleic acid.

F. General Terms

Before the present compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

A. Materials

In a rapid viral load assay, nucleic acids tested may be RNA or DNA having about 8,000 bases or base pairs. Nucleic acid (DNA and RNA) ladders in this size range were tested for localization. Unless otherwise specified, EcoR I digest of lambda phage DNA with fragments of 3,530, 4,878, 5,643, 5,804, 7,421, and 21,226 base pairs was used as the model nucleic acid. Comparison to other DNA and RNA ladders with fragments between 50 and 10,000 bases or base pairs indicated similarity between RNA and DNA localization. Gel electrophoresis on filtered nucleic acid ladders indicated higher retention for molecules larger than about 1,500 bases or base pairs. Purified Calf Thymus DNA of 13,000 average base pair length was filtered under varying conditions and the results noted in the Examples below. Filtration was done with a filter assembly including Millipore multiwell filter plates modified to include 0.2 micron Anopore membrane filters similar to the well assembly shown in FIG. 15a with modified and unmodified 0.2 micron Anopore membrane filter surfaces of approximately 5 millimeter diameter.

1. Example 1

Figure 24A:
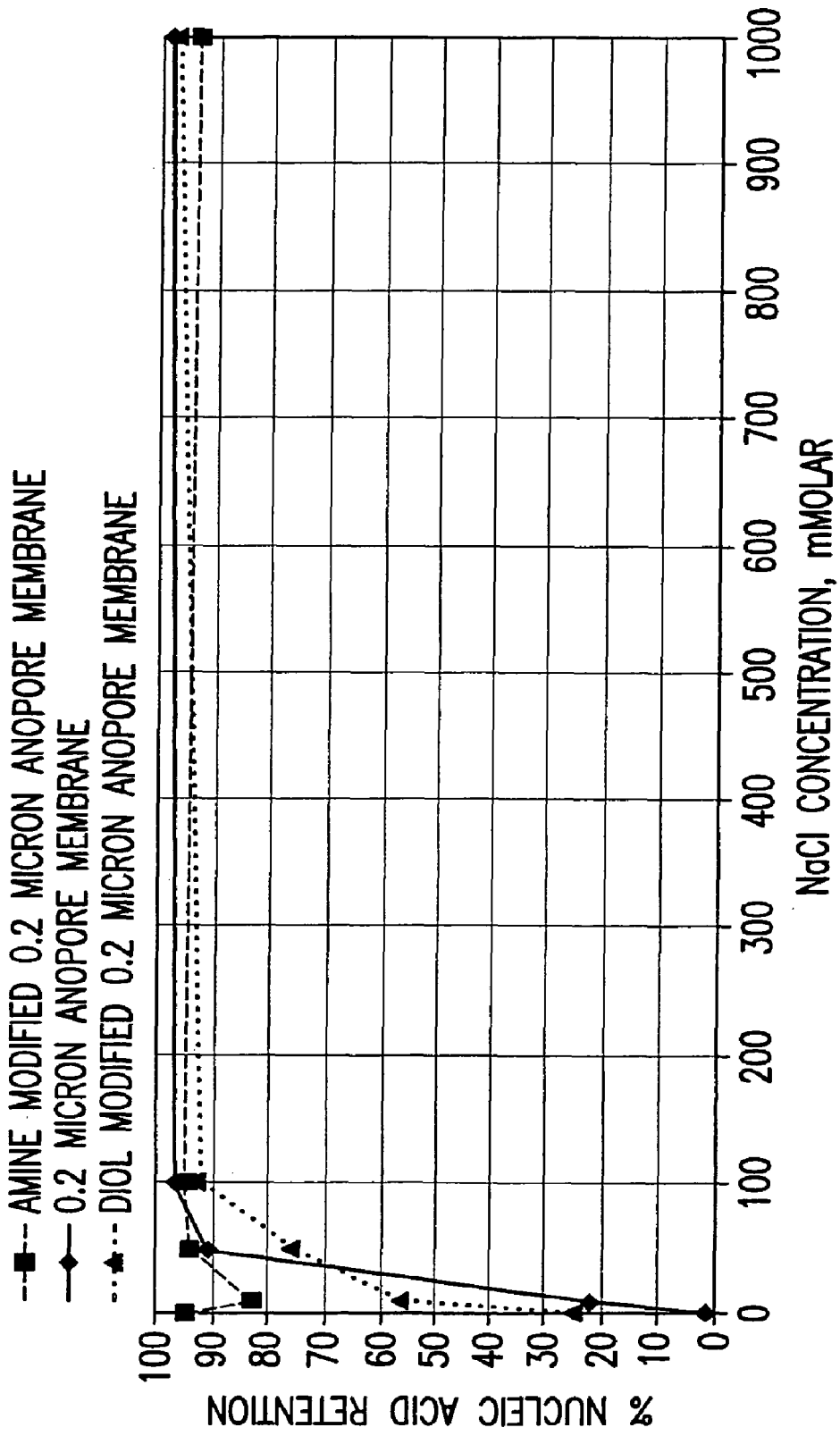
FIG. 24a is a graph of nucleic acid retention vs. NaCl concentration for plain unmodified, diol (acid hydrolyzed glycidoxypropyltrimethoxysilane) modified, and amine (aminopropyltrimethoxysilane) modified 0.2 micron Anopore membranes.
Figure 24B:
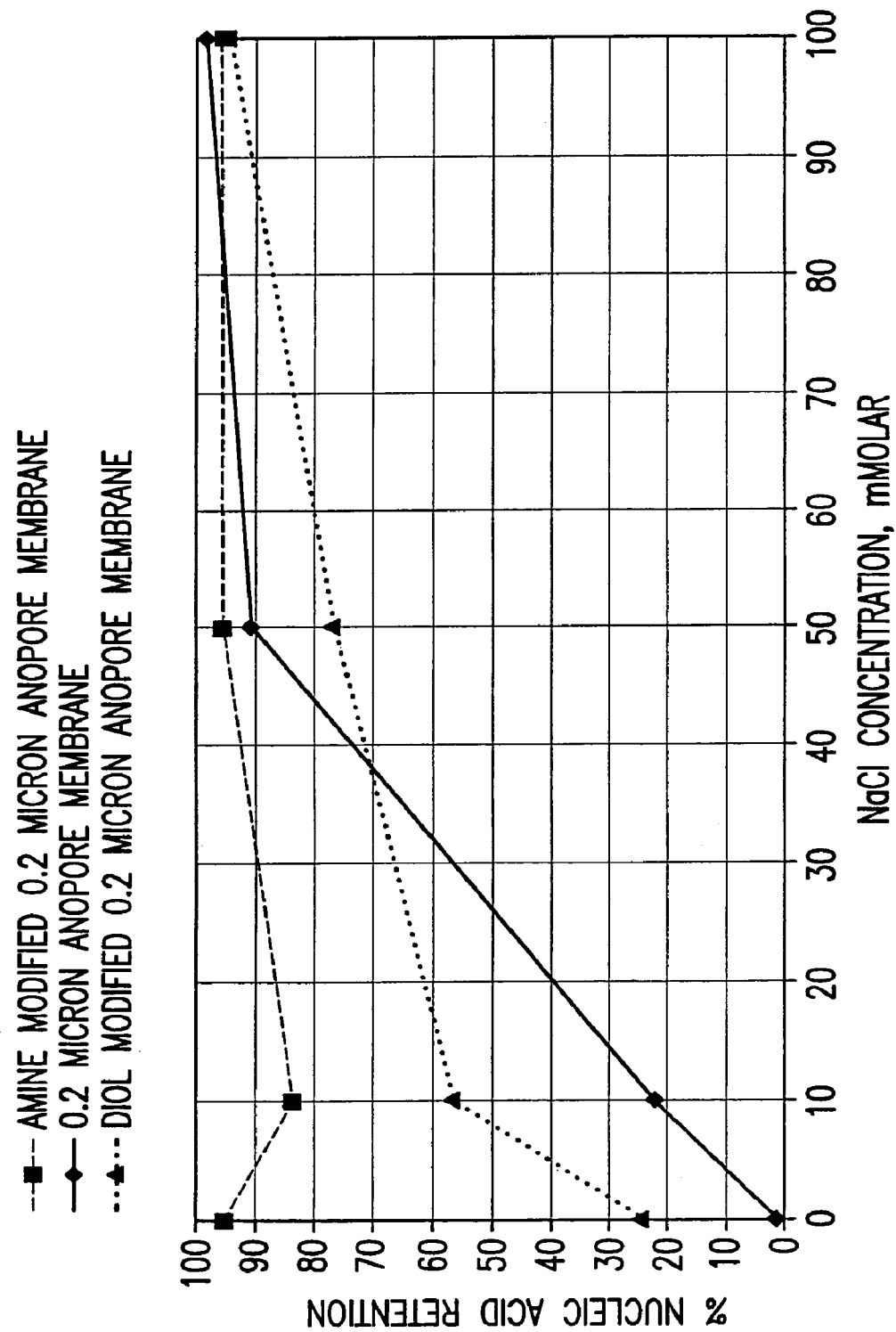
FIG. 24b is a graph of nucleic acid retention vs. NaCl concentration for plain unmodified, diol (acid hydrolyzed glycidoxypropyltrimethoxysilane) modified, and amine (aminopropyltrimethoxysilane) modified 0.2 micron Anopore membranes.

FIGS. 24a and 24b are graphs of nucleic acid retention vs. NaCl concentration for plain unmodified, diol (acid hydrolyzed glycidoxypropyltrimethoxysilane) modified, and amine(aminopropyltrimethoxysilane) modified 0.2 micron Anopore membranes. FIG. 24a shows a 0 to 1000 mM NaCl range, while FIG. 24b shows an expanded 0 to 100 mM range from FIG. 24a. These results were generated in 1 mM Tris buffer, pH 8.0. As is apparent from the graphs, 100 mM of salt is required for substantially complete nucleic acid retention on the plain and diol modified membranes, with substantially no salt effect noted for the amine modified membrane.

2. Example 2

Figure 25A:
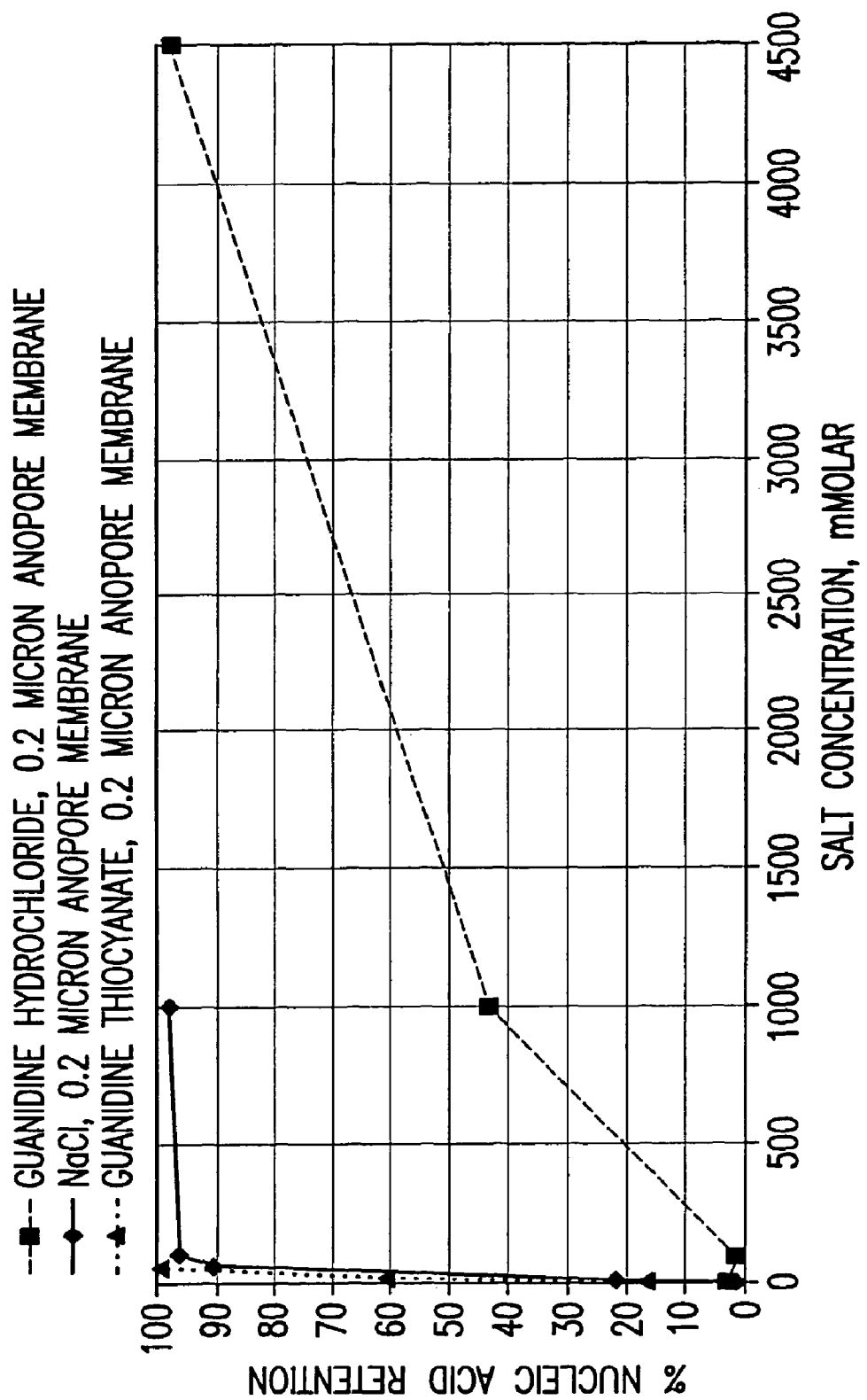
FIG. 25a is a graph of nucleic acid retention vs. salt concentration (chaotropic and NaCl) for plain unmodified Anopore membranes.
Figure 25B:
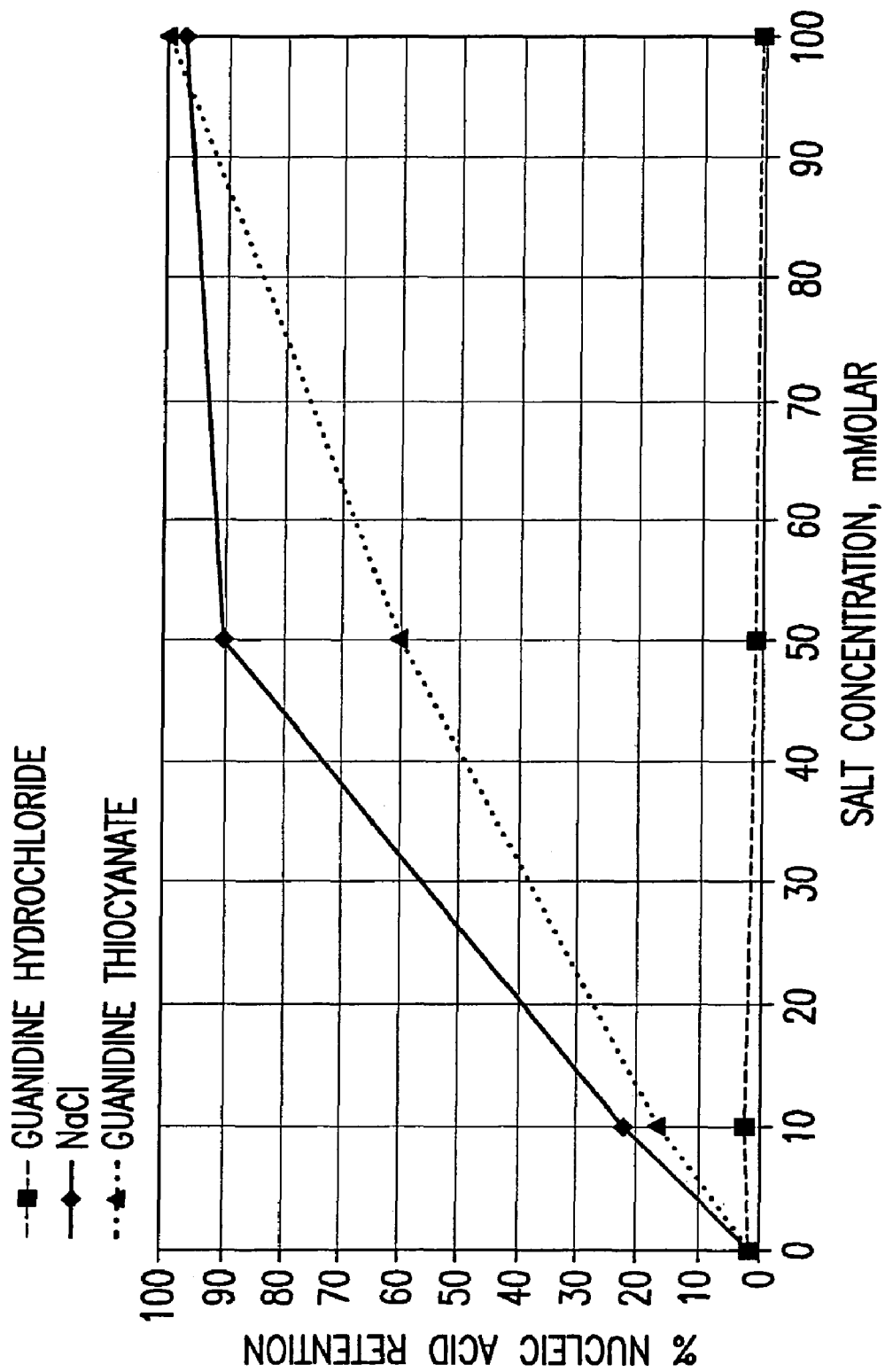
FIG. 25b is a graph of nucleic acid retention vs. salt concentration (chaotropic and NaCl) for plain unmodified Anopore membranes.

FIGS. 25a and 25b are graphs of nucleic acid retention vs. salt concentration (chaotropic and NaCl) for plain unmodified Anopore membranes. FIG. 25a shows a 0 to 4500 mM salt range, while FIG. 23b shows an expanded 0 to 100 mM range from FIG. 25a. These results were generated in 1 mM Tris buffer, pH 8.0, using the DNA digest cited above. As indicated in the graphs of FIGS. 25a and 25b, NaCl (not a chaotropic salt) was as effective as guanidine thiocyanate in promoting nucleic acid retention on plain 0.2 micron Anopore membranes, and much more effective than guanidine hydrochloride.

3. Example 3

Figure 26:
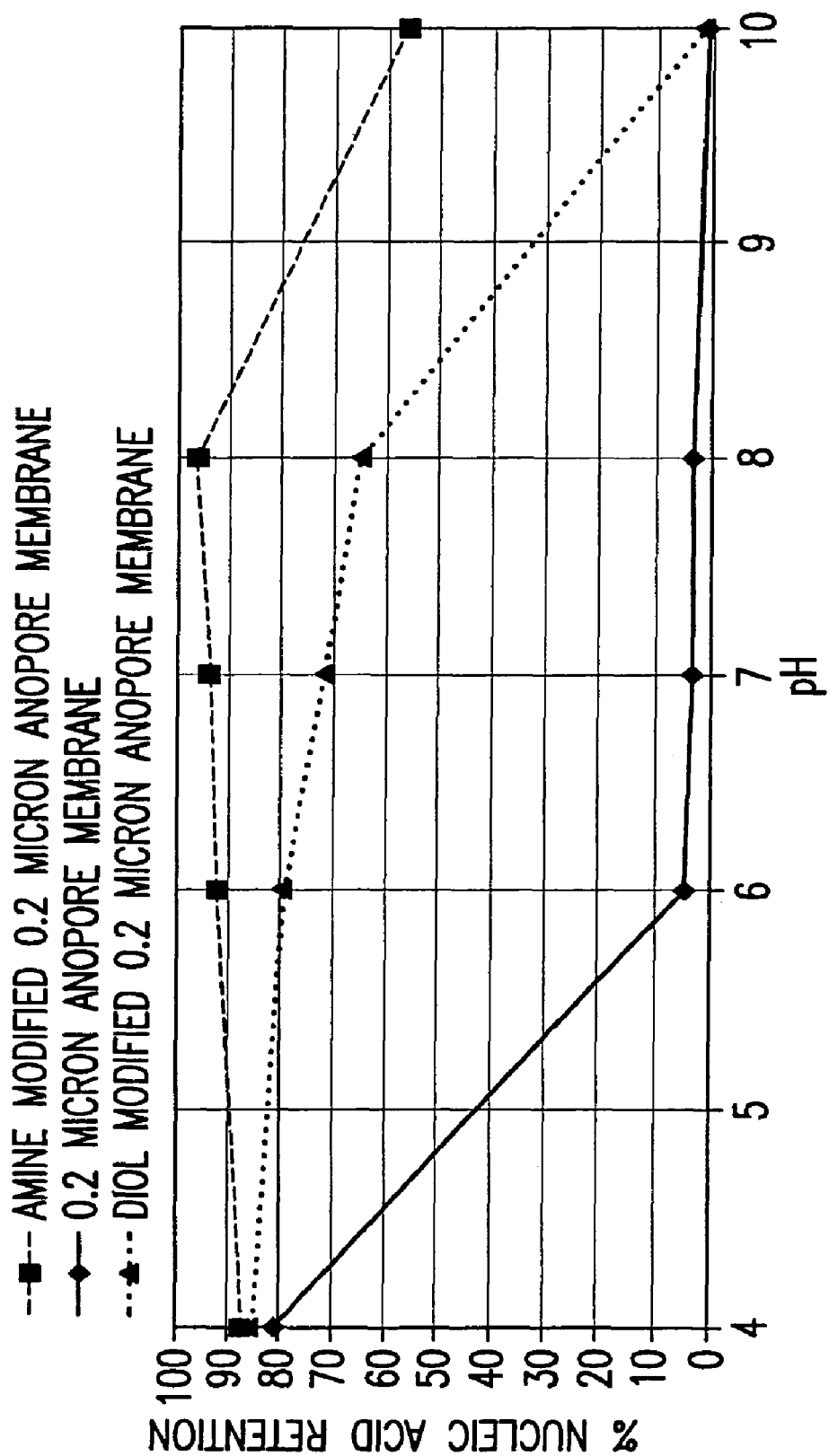
FIG. 26 is a graph of nucleic acid retention vs. pH for plain unmodified, diol modified, and amine (APS) modified 0.2 micron Anopore membranes.

FIG. 26 is a graph of nucleic acid retention vs. pH for plain unmodified, diol modified, and amine (APS) modified 0.2 micron Anopore membranes. The results were generated in 1 molar NaCl, 50 mM phosphate buffer, and DNA digest as previously described. As shown in the graph of FIG. 26, nucleic acid retention was uniformly high and independent of surface modification at pH 4, but significant surface modification effects were indicated at pH 6 thru 8, with the plain membrane dropping to below 5% nucleic acid retention, and the diol modified membrane dropping to about 65% retention. At high pH (10), nucleic acid retention fell to essentially 0 for the plain and diol modified membranes, but was still above 50% for the amine modified membrane.

4. Example 4

Figure 27:
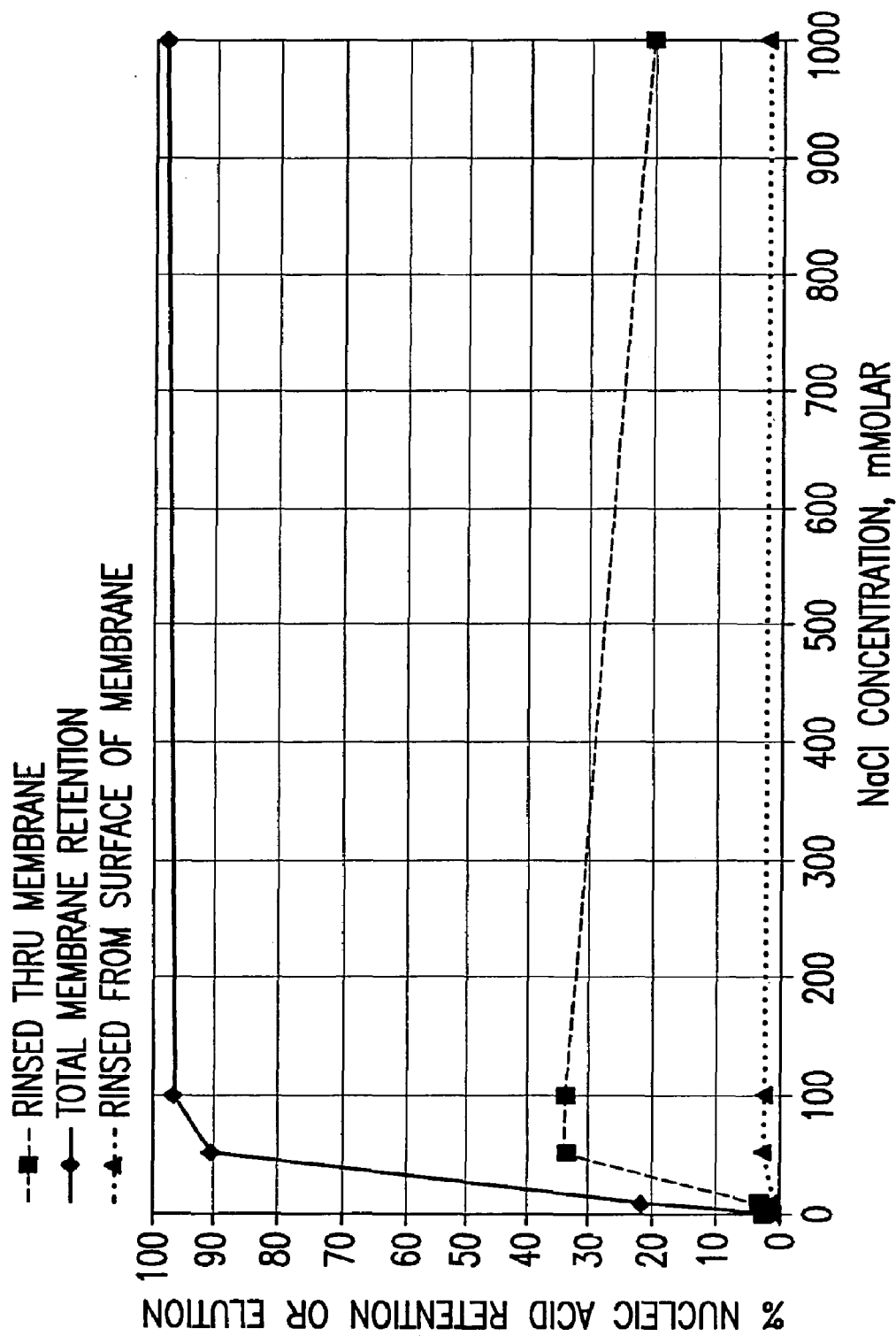
FIG. 27 is a graphs showing the nature of nucleic acid retention on a plain unmodified Anopore membrane in variable NaCl, with 1 mM Tris buffer, pH 8.0.
Figure 28:
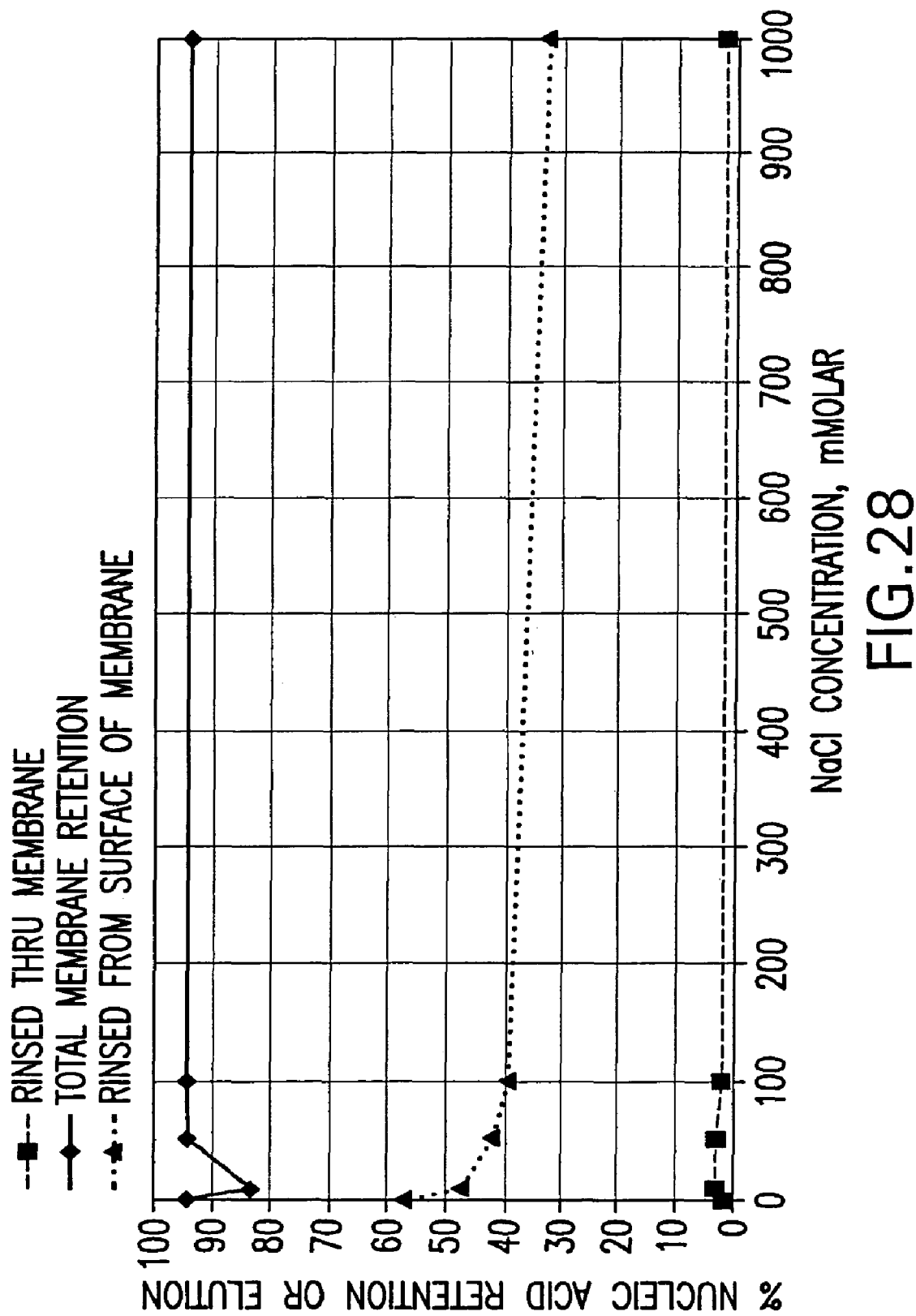
FIG. 28 is a graph showing the nature of nucleic acid retention on an amine (APS) modified Anopore membrane in variable NaCl, with 1 mM Tris buffer, pH 8.0.
Figure 29:
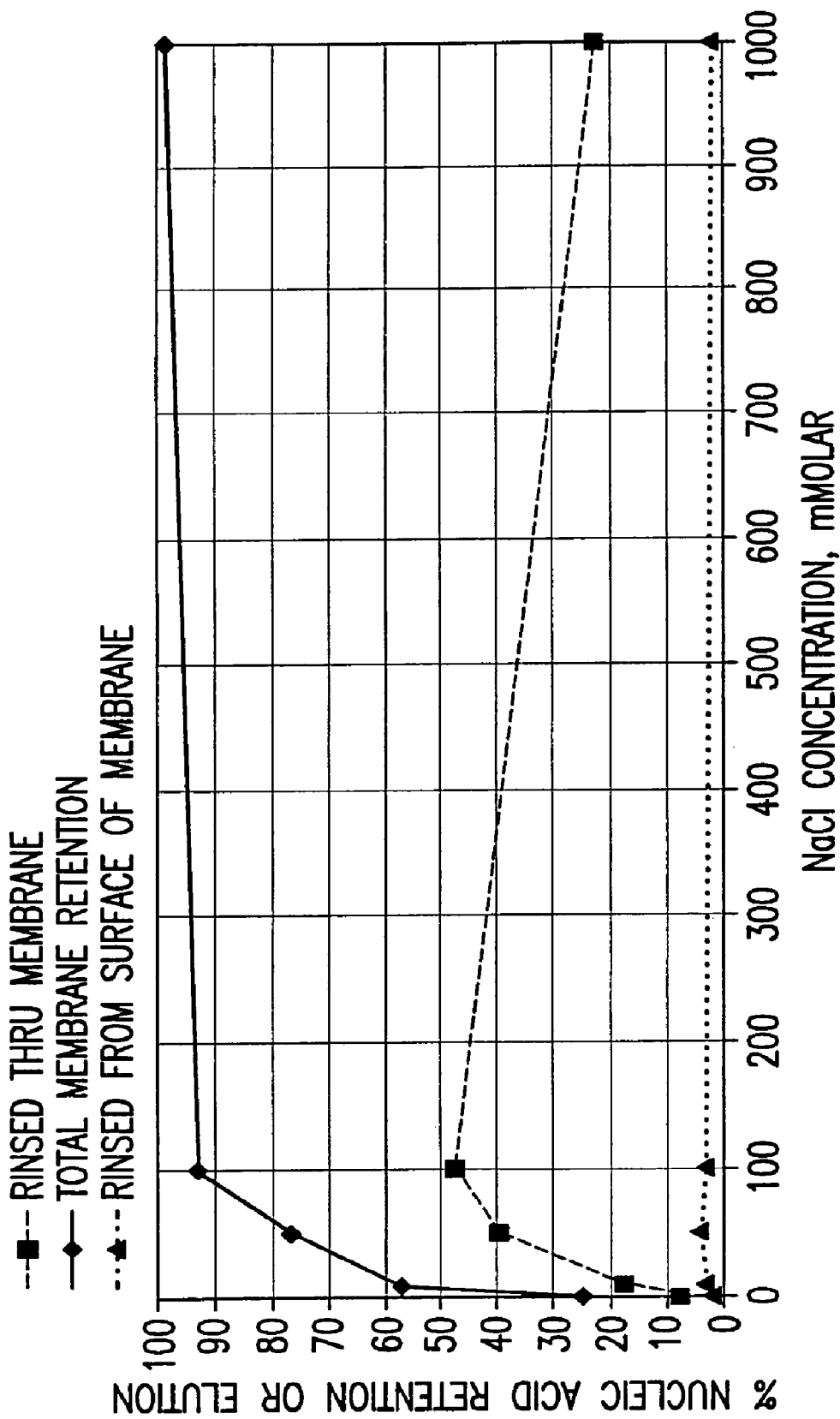
FIG. 29 is a graph showing the nature of nucleic acid retention on a diol modified Anopore membrane in variable NaCl, with 1 mM Tris buffer, pH 8.0.

The graphs of FIGS. 27-29 show the nature of nucleic acid retention on plain unmodified, amine (APS) modified, and diol modified Anopore membranes in variable NaCl, with 1 mM Tris buffer, pH 8.0. Each of these graph plots % nucleic acid retention or elution vs. NaCl concentration for three cases:

Total Membrane Retention (plot is identical to FIG. 24a);

Rinsed Thru Membrane—after the specified buffer containing nucleic acid was filtered thru the membrane, an equal volume of identical buffer, without nucleic acid, was filtered thru the membrane and analyzed.

Rinsed From Surface of Membrane—after the membrane was rinsed (Rinsed Thru Membrane, above), an equal volume of identical buffer, without nucleic acid, was placed in the well above the membrane. This buffer was aspirated and dispensed approximately 10 times onto the membrane to rinse localized nucleic acids from the surface. This surface rinse was analyzed by absorbance and eluted nucleic acids were calculated.

Plain and diol modified Anopore membranes (FIGS. 27 and 29, respectively) showed an appreciable thru rinse fraction where nucleic acids were apparently retarded rather than retained as they flowed thru the filter. Little nucleic acid was rinsed from the filter surface after this thru rinse. Amine modified Anopore membranes (APS, FIG. 28) showed different behavior. Thru rinse removed little nucleic acid from the modified membrane, while in some cases nearly 60% of the starting nucleic acid was able to be rinsed from the surface of the membrane.

5. Example 5

Figure 30:
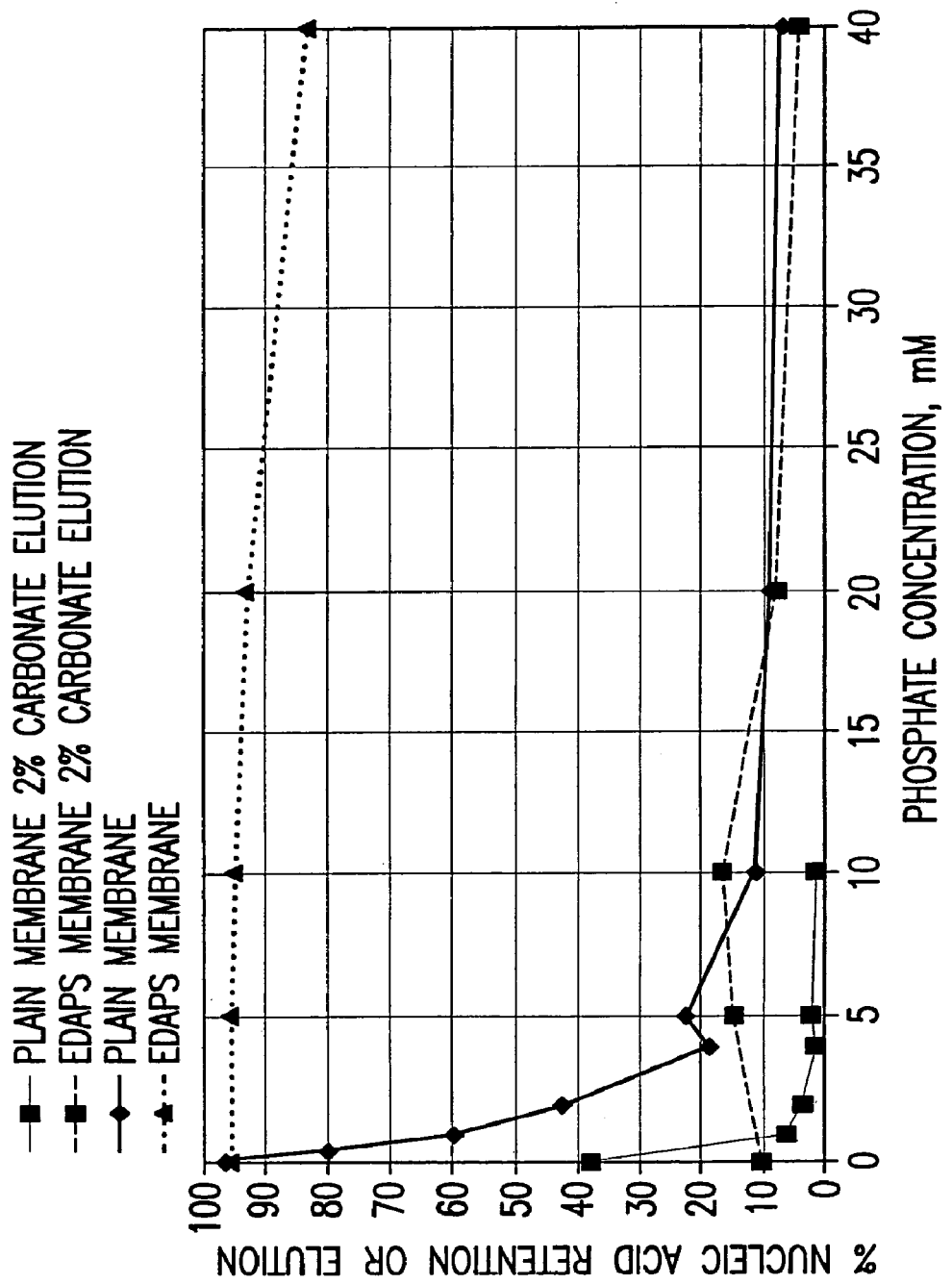
FIG. 30 is a graph showing the effect of phosphate buffer concentration on nucleic acid retention or elution for plain unmodified and amine (ethylenediaminopropyltrimethoxysilane, EDAPS) modified membranes.

The graph of FIG. 30 shows the effect of phosphate buffer concentration on nucleic acid retention or elution for plain unmodified and amine (ethylenediaminopropyltrimethoxysilane, EDAPS) modified membranes. Disodium phosphate was added to 1 M NaCl in the listed concentrations on the graph and the pH was adjusted to 8.0. Phosphate ions are known to bind to aluminum oxide chromatography packings and may compete for the same weak binding sites on Anopore membranes as nucleic acids. As shown in the graph of FIG. 30, nucleic acid localization by EDAPS modified Anopore membranes was not nearly as sensitive to phosphate concentration as plain membranes.

Other buffers are also capable of lowering nucleic acid localization on unmodified Anopore membranes. Table 2 shows the percent retention of DNA in 1000 mM NaCl containing the indicated buffers.

TABLE 2

| Buffer | % Nucleic Acid Localization |
| --- | --- |
| 1 mM Tris | 98.3% |
| 50 mM Tris-Borate-EDTA | 17.8% |
| 50 mM Phosphate | −2.6% |
| 50 mM Bicarbonate | 4.6% |
| 50 mM Borate | 5.7% |

6. Example 6

Surface properties are frequently affected by adsorption of species that block weak interactions. Such species can be used as membrane coating materials and include surfactants and components of plasma that may be present in some applications described herein Table 5 shows the percent localization of DNA under conditions that may be found in viral load assays, including 1 mg/ml Proteinase K enzyme, 2% Tween 20 surfactant, added salt as noted, and with and without 65% EDTA human plasma.

TABLE 3

| Membrane | Salt | Plasma % | Nucleic Acid Localization |
|---|---|---|---|
| Amine-EDAPS | None | 65% | 99% |
| Amine-EDAPS | None | 0% | 99% |
| Amine-EDAPS | 200 mM NaCl | 65% | 96% |
| Amine-EDAPS | 200 mM NaCl | 0% | 98% |
| Amine-EDAPS | 200 mM GTC | 65% | 100% |
| Amine-EDAPS | 200 mM GTC | 0% | 96% |
| Unmodified | None | 65% | 42% |
| Unmodified | None | 0% | 28% |
| Unmodified | 200 mM NaCl | 65% | 56% |
| Unmodified | 200 mM NaCl | 0% | 97% |
| Unmodified | 200 mM GTC | 65% | 13% |
| Unmodified | 200 mM GTC | 0% | 96% |

As indicated in Table 3, nucleic acid localization by EDAPS modified membranes remained consistently high under the varying salt and plasma conditions, while the unmodified membranes had inconsistent nucleic acid localization under the varying conditions.

7. Example 7

In a high sensitivity viral load assay, very small amounts of nucleic acids are quantitized. Table 4 below shows the percent localization of HIV RNA obtained from pooled clinical samples vs. virion lysis/plasma digestion reaction conditions. All samples contained a 135 µl patient sample (EDTA plasma), 2 mg/ml proteinase K, 2% Tween 20, and 400 mM guanidine thiocyanate. The samples were incubated for 30 minutes under the conditions listed in Table 4.

TABLE 4

| Incubation | Membrane | RNA Concentration | % Localization |
|---|---|---|---|
| Room Temp | None | 321k copies/ml | — |
| Room Temp | Plain | 274k copies/ml | 14.6% |
| Room Temp | EDAPS | 5.7k copies/ml | 98.2% |
| 55° C. | None | 542k copies/ml | — |
| 55° C. | Plain | 427k copies/ml | 21.2% |
| 55° C. | EDAPS | 4.1k copies/ml | 99.2% |
| RT Sonicated | None | 481k copies/ml | — |
| RT Sonicated | plain | 388k copies/ml | 19.3% |
| RT Sonicated | EDAPS | 5.8k copies/ml | 98.8% |

As indicated in Table 4, RNA localization by EDAPS modified membranes remained consistently high under the varying incubation conditions, while the plain unmodified membranes had much lower RNA localization under the varying incubation conditions.

8. Example 8

The effect of test sample digestion on human plasma filtration was investigated by use of 300 µl total incubation mixtures containing the ingredients and subject to the conditions listed in Table 5 below. The filter assembly used included unmodified, 0.2 micron Anopore membrane filters approximately 5 mm in diameter heat fused to the bottom of modified Millipore 96 well filter plates, such as shown in the embodiment of FIG. 15a.

TABLE 5

| Sample[1] | Proteinase K Enzyme[2] | Surfactant[3] | Chaotrope | Incubation Temp.[4] | Incubation Time | Filtration Time[5] |
|---|---|---|---|---|---|---|
| 1 (200 µl Plasma) | None | None | None | RT | None | Plugged |
| 2 (As Above) | 2.3 mg/ml | None | None | 55° C. | 20 min. | Plugged |
| 3 (As Above) | 2.3 mg/ml | None | 0.5M GITC | 55° C. | 20 min. | Plugged |
| 4 (As Above) | 2.3 mg/ml | 0.5% Triton | 0.5M GITC | 55° C. | 20 min. | 15 sec. |
| 5 (As Above) | 2.3 mg/ml | 0.5% Triton | None | 55° C. | 20 min. | 18 sec. |
| 6 (As Above) | 2.3 mg/ml | 2.0% Tween | None | 55° C. | 20 min. | 15 sec. |
| 7 (As Above) | 1.7 mg/ml | 1% SDS | None | 55° C. | 30 min. | 15 sec. |
| 8 (As Above) | 1.0 mg/ml | 2% Tween | None | RT | 30 min. | 14 sec. |
| 9 (As Above) | None | 2% Tween | None | RT | 30 min. | 4+ min. |

[1]Sample - Fresh or frozen EDTA human plasma
[2]Proteinase K Enzyme - Liquid concentrate (23 mg/ml), Sigma-Aldrich Co.
[3]Surfactant - Molecular Grade Triton X-100, Tween 20, or SDS (Sodium Dodecyl Sulfate)
[4]Incubation Conditions - RT (Room Temperature) 25° C. benchtop; 55° C. water bath.
[5]Filtration Time - The number of seconds to filter 250 µl of incubate thru the localization membrane filter.

As indicated in Table 5, sample digestion allowed 200 µl plasma samples to be filtered through 0.2 micron filters in a few seconds in a convenient multiwell format when a surfactant was used.

9. Example 9

Figure 31:
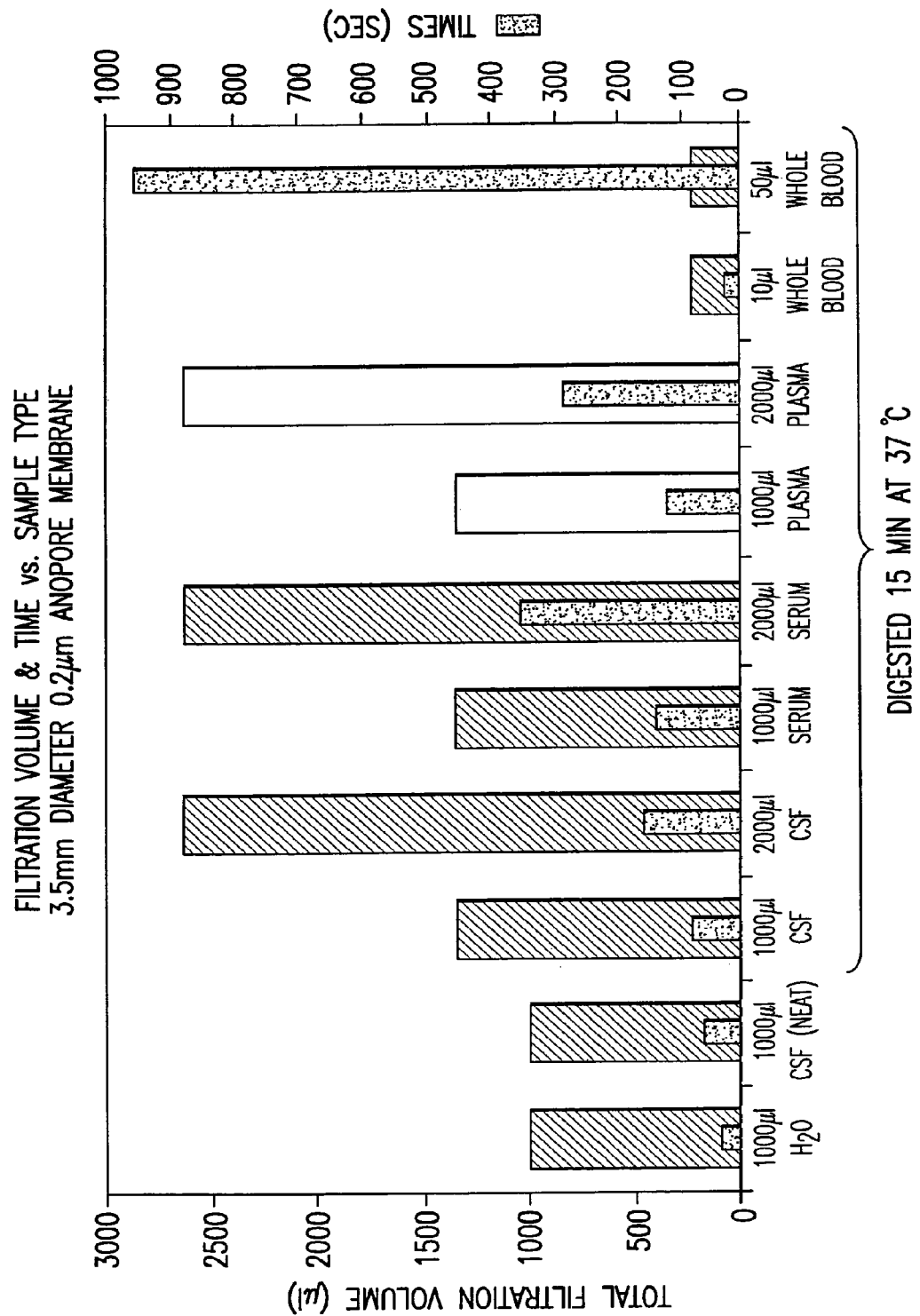
FIG. 31 is a bar graph of a sample digestion/filtration study for cerebral spinal fluid (CSF), human serum, and whole blood.

FIG. 31 is a bar graph of a sample digestion/filtration study for cerebral spinal fluid (CSF), human serum, and whole blood. Total filtration volume is shown on the left axis, while time to filter the total volume through an unmodified 0.2 micron Anopore filter of approximate 3.5 millimeter diameter is shown on the right axis. Various samples and digestion conditions are shown, including water (control), neat (undigested) CSF, and digested CSF, serum, plasma, and whole blood. Digestion conditions were 15 minutes at 37° C. in a total digestion volume as shown containing the following:
  CSF, serum, plasma
  31 mM Tris HCl, 10 mM EDTA
  800 mM Guanidine Isothiocyanate
  0.5% Triton X-100

5.2% Tween 20
0.9 AU Proteinase
Whole Blood
18 mM Tris HCl, 6 mM EDTA
500 mM Guanidine Isothiocyanate
0.3% Triton X-100
3.0% Tween 20
2.0 mg/ml Proteinase K As is seen, practical volumes of various biological samples are filterable through small area Anopore filters in reasonable times.

10. Example 10

Genomic nucleic acid extraction and purification from whole blood including PCR amplification was carried out using the following procedure. Initially, 10 microliters of EDTA anticoagulated human whole blood was diluted into 180 microliters of molecular grade water containing 10 microliters of a solution of 10% sodium dodecyl sulfate (SDS) for a final concentration of 0.5%. The mixture was briefly mixed, then incubated at room temperature for approximately 15 minutes. The entire sample was placed into a multiwell filter plate (modified Millipore filter plate as previously described) with an integral untreated 0.2 micron Anopore membrane. The mixture was vacuum filtered over about 30 seconds to dryness then rinsed with about 100 microliters of distilled water that was again vacuum filtered to dryness through the membrane. The rinsed membrane was essentially white, with very little bound hemoglobin apparent. Thereafter, 20 microliters of PCR master mix, including primers for the amplification of nucleic acid sequences involved in the genetic coding for human beta globin protein, was dispensed onto the filter and briefly allowed to resuspend any localized genomic DNA that was captured from the initial SDS lysed blood sample. The resuspension was aided by repeatedly dispensing and aspirating the 20 microliter master mix onto the membrane. The master mix was aspirated and transferred to a PCR capillary tube and analyzed by real time PCR (Roche Lightcycler) for nucleic acid sequences involved in the genetic coding for human beta globin protein. Positive results were obtained.

Figure 32:
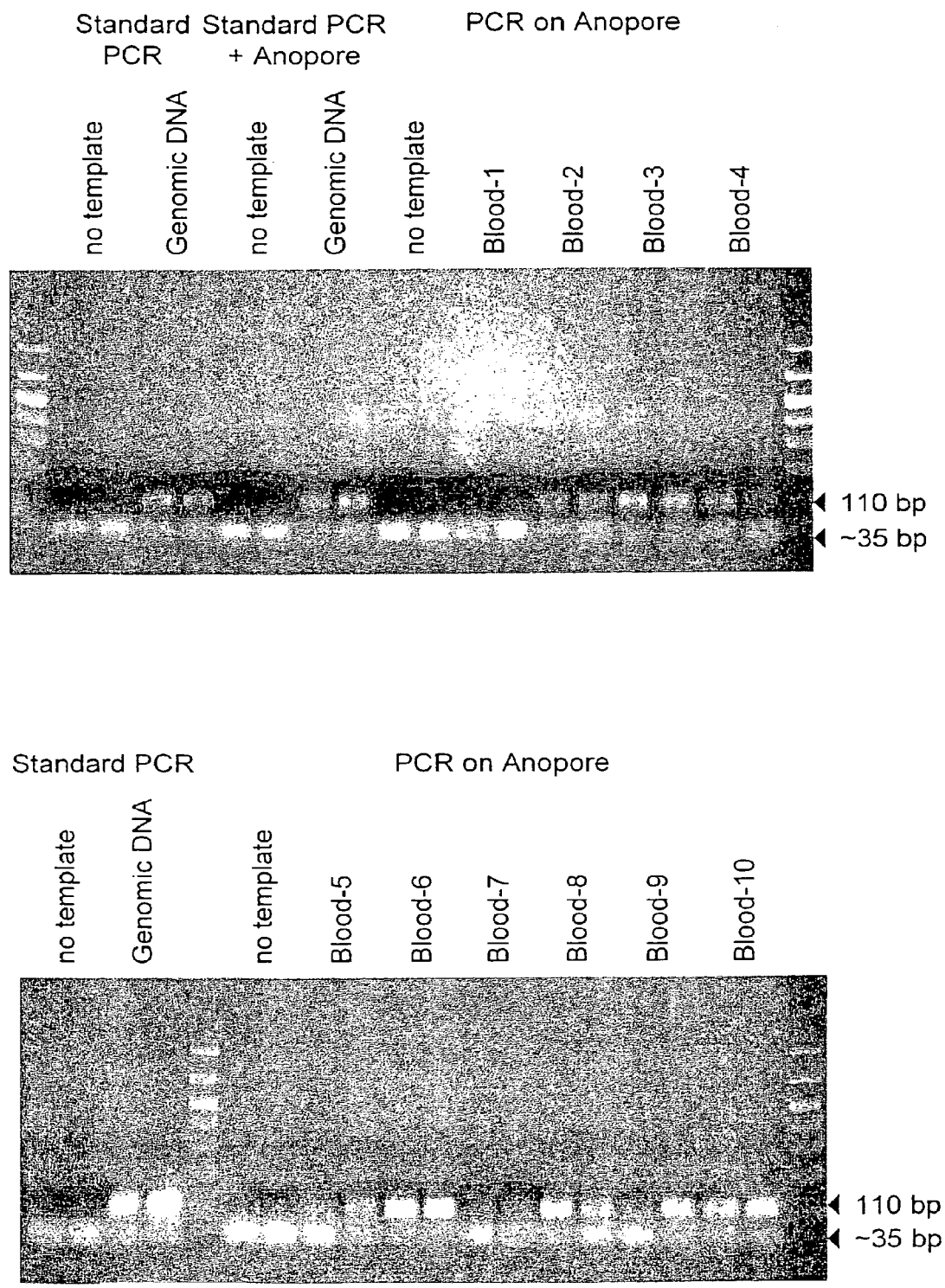
FIG. 32 is a photograph of the electrophoretic gel showing amplicons generated by PCR multiplication of beta globin target regions present on the localized genomic DNA contained within the whole blood samples.

10 ul whole blood from various de-identified samples was lysed in 200 ul total volume containing 500 mM Guanidine Isothiocyanate, 0.5% Triton-X 100, 20 mM Tris-HCl, pH 6.5, 10 mM EDTA and 0.25 mg/ml Proteinase K (>500 U/mg) for 15 minutes at room temperature (~25 C). The lysate was subsequently filtered through an unmodified Anopore membrane (d=~3.8 mm) by vacuum and then washed with 100 ul of 200 mM NaCl. The filter was then dried and the backside passivated with a 1-3 ul bead of DYMAX OP-21 flexible plastic bonder which was UV cured for 5 seconds after application. The membrane containing the surface localized DNA derived from the whole blood samples was then added to 50 microliters of PCR master mix in a conventional PCR tube containing: 1×PCR buffer (Roche), 4 mM $MgCl_2$ (Roche), 2 mM dATP, dCTP, dGTP and 4 mM dUTP (Perkin Elmer), 500 ug/ml BSA (Idaho Technology), 0.5 uM each $PCO_3$ and $PCO_4$ primers, 1U Heat Labile Uracil N-Glycosylase (Roche) and 3U FastStart Taq Polymerase (Roche). PCR thermal cycling performed in a conventional thermal cycler as follows: 50 degrees C.×5 min. (UNG), 95 degrees C.×5 min (taq activation), 40 cycles of [95 degrees C.×3 secs, 55 degrees C.×45 secs, 72 degrees C.×60 secs], followed by a final extension at 72 degrees C. for 5 min. 10 ul of each 50 ul PCR reaction was then loaded onto a 2% agarose, TBE gel and electrophoresed. Bands representing β-Globin (~10 bp) or primer dimer (~35 bp) were visualized after staining gel in ethidium bromide and viewing under UV light. Positive results indicating the presence of human genomic DNA were obtained. FIG. 32 is a photograph of the electrophoretic gel showing amplicons generated by PCR multiplication of beta globin target regions present on the localized genomic DNA contained within the whole blood samples. As is seen, PCR amplification occurred in all cases.

11. Example 11

The ability to use whole blood samples in real time PCR (RT-PCR) for genetic analysis would simplify laboratory workflow and potentially reduce costs and offer other advantages. The whole blood PCR amplification of Example 10 has been expanded to include real time detection of generated amplicons by performing the analysis in a system similar to that of FIG. 17b, using the simplified disposable format shown in FIGS. 18 and 19 as previously described. 10 ul whole blood was lysed then filtered and rinsed through unmodified Anopore filters as generally shown in FIG. 18 and as described in Example 10. The dried bottom surface of the Anopore, containing localized genomic DNA derived from the whole blood sample, was sealed by heat welding polypropylene heat sealing film 1910 directly onto the dry membrane, as shown in FIG. 19. 50 microliters of PCR master mix was then added into wells 1901, of formulation as previously described, but included 1:6000 dilution of Sybergreen I dye (Molecular Probes). The tops of wells 1901, containing PCR reaction liquid 1913, was then sealed by clear adhesive tape 1911 or clear caps 1912. This assembly was thermally cycled in a real time PCR instrument designed to transfer heat directly across the Anopore-sealing film surface as depicted in FIG. 17b. Changes in fluorescence within the wells was monitored during thermal cycling by a simplified fluorometer composed of an ultra bright blue light emitting diode, photodiode detector, and suitable interference filters, electronics and software. Fluorescence data was evaluated by Lightcycler (Roche) software. Thermal cycling was accomplished by employing a Perkin Elmer 480 instrument modified to allow remote operation of a custom built flat thermal cycling area. Thermal cycling profile was similar to Example 10 (99 degrees C.×20 sec., 50 degrees C.×3 secs., 75 degrees C.×60 seqs.). Melting analysis was done by ramping the temperature from 65 degrees C. to 99 degrees C. over a one hour period.

Figure 33:
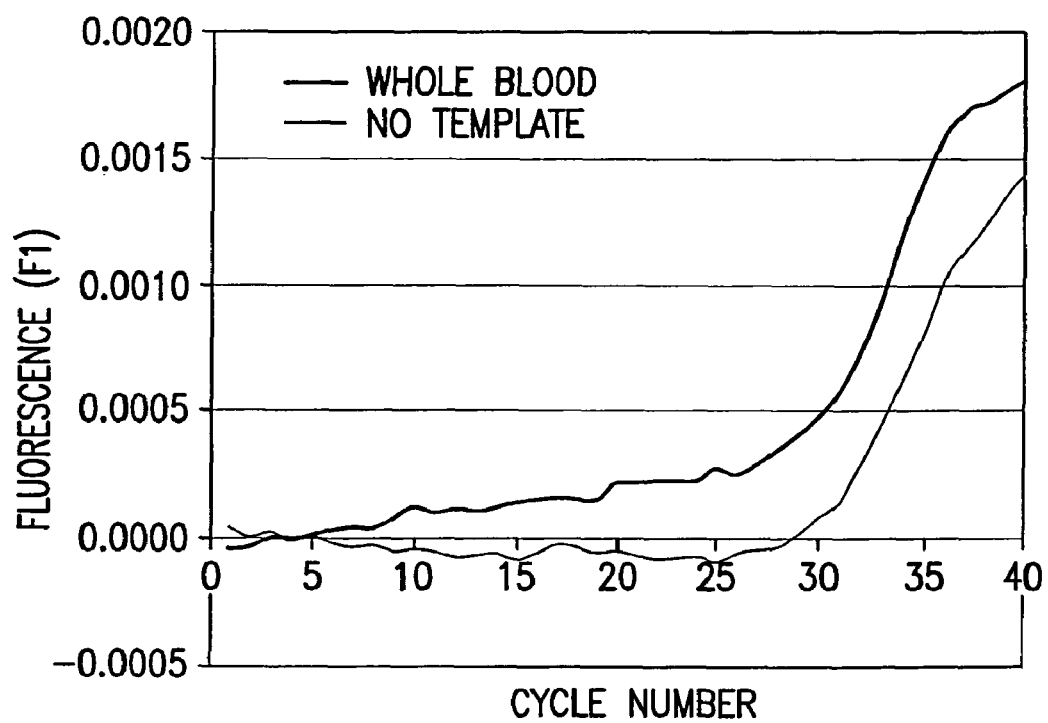
FIG. 33 is a real time amplification curve for β globin PCR amplification/detection of nucleic acids from lysed blood.
Figure 34:
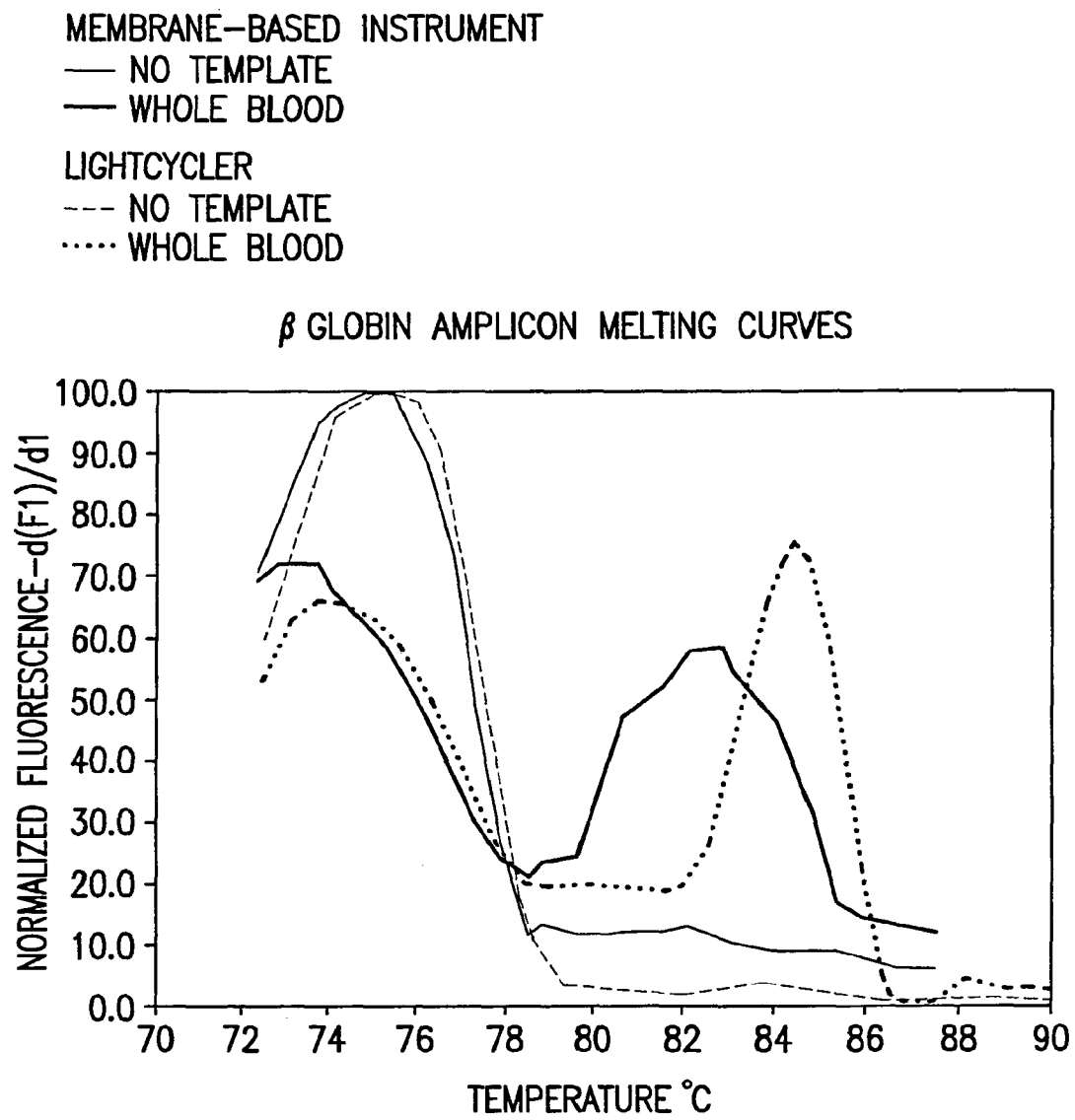
FIG. 34 shows β globin amplicon melting curves of nucleic acids from lysed blood.

A real time amplification curve for Example 11 is shown in FIG. 33, while a melting curve is shown in FIG. 34. Similar results are shown for a lightcycler in FIG. 34. The figures show unequivocal evidence of specific PCR amplification and identification of the beta globin gene from membrane localized DNA from digested whole blood in a simplified real time format.

12. Example 12

Human genomic DNA can be directly visualized by fluorescent staining. 10 ul of purified human white blood cells, concentration greater than 1 million cells/ml, was added to 190 ul of TE buffer containing 0.5% sodium dodecyl sulfate and incubated for 20 minutes at 56 degrees C. to lyse the white blood cells and release DNA. This solution was diluted to a final concentration, based on the starting 10 ul of cell solution, of 1 to 400,000 in a solution composed of 1 to 10,000 dilution of Syber Gold in TE buffer. The dilute DNA solution was incubated in the Syber Gold solution for a few minutes, then 50 ul filtered across a Nickel-Boron modified Anopore membrane according to Example 22. The membrane, containing localized human genomic DNA, was briefly rinsed with TE buffer then visualized on an instrument similar to shown in FIG. 9 and further described in Example 13. A typical image of human genomic DNA according to this example is shown as FIG. 11.

13. Example 13

Nucleic acids were optically analyzed. Purified calf thymus DNA of approximately 13,000 base pairs was serial diluted at the relative concentrations of 1 to 128 into filtered 10 mMolar Tris-HCl, 1 mMolar EDTA, pH 7.5 buffer containing 100 nanomolar YOYO-1 nucleic acid dye. After 5 minutes of room temperature incubation, 100 microliters of the dyed nucleic acid samples were filtered through an unmodified 0.2 micron Anopore membrane of approximately 3 mm active filter diameter that had been heat fused onto a black polypropylene holder. The filter was imaged with a fluorescence microscope of the configuration shown in FIG. 9, using a 20 milliwatt air cooled argon laser operating single line at 488 nm, and a 1024×1058 pixel backthinned CCD camera cooled to −10° C. with a 0.3 NA 10× flat field microscope objective. The DNA is easily visualized with approximately 5 second exposure. The images were signal processed to sharpen edges, remove obvious non nucleic acid defects, corrected for background fluorescence, etc., then the remaining processed DNA spots were numerically counted. The processed images are shown in FIG. 12, the resulting simple dilution curve in FIG. 13, and the dilution curve corrected for instrument and system parameters in FIG. 14.

14. Example 14

Theoretical modeling was carried out to evaluate various detection parameters for a confocal scanning detection system such as depicted in FIG. 8. The following assumptions were made for the theoretical modeling.

1. Nucleic acids contained in a 1 ml sample can be bound to a 1 $cm^2$ area.
2. A false positive rate due to counting error of 1 per $cm^2$ is acceptable.
3. Nucleic acids are stained with 25 or 100 dye molecules/nucleic acid.
4. Each fluorescent dye molecule generates a detected signal of 50,000 photons/second when in the detection zone. This is achieved at illumination densities of 100 $kW/cm^2$.
5. Noise is from background sources such as instrumentation noise, Raman scattering, plastic fluorescence, etc. Additionally, surface nonspecific binding (NSB) from nucleic acid staining results in uniformly distributed, isolated (non-clumped) dye molecules with a very low probability of multiple dyes/scanning area. Inadvertent staining of surface bound nonspecific nucleic acids, etc. that gives a clumped fluorescent signal has not been considered.

The theoretical modeling was based on the following detection conditions. A fluorescently labeled nucleic acid is bound to an optical surface. A confocal scanning epifluorometer intensely illuminates the bound nucleic acid causing it to fluoresce. Emitted fluorescent photons from the nucleic acid are captured and counted. Additionally, the epifluorometer detects a background count rate from scattered light, instrument noise, NSB, etc. The specific signal from the fluorescent nucleic acid is present as a small burst of photons occurring in an interval defined by the scanning speed and spot size. As a typical example, bursts of 3 to 20 photons occurring in 0.5 to 10 microseconds were calculated. The background or noise signal follows a Poisson distribution and has a finite probability of occurring in bursts that are indistinguishable from the specific nucleic acid signal.

Required detection parameters (SNR, scan speed, spot size, etc.) were determined by setting the fluorescent nucleic acid signal equal to the maximum statistical noise burst count occurring during the 1 $cm^2$ scan. This results in a statistical false positive count of 1/$cm^2$ from background noise. That is to say, a given scan speed and scan spot size results in a photon burst time, which is the time it takes for the illumination spot to sweep over an immobilized fluorescent nucleic acid (e.g., about 0.5 to about 10 microseconds). The number of photons counted by the detector per photon burst time is used to discriminate between nucleic acids and background. Background noise contains small bursts due to statistical fluctuations. The minimum required nucleic acid signal (photons/burst time) is set equal to the maximum noise signal (photons/burst time) that may statistically occur once during the total scan time. Accordingly, the instrument counts 1 nucleic acid each time this specified burst rate (for instance 5 photons in 2 microseconds) is exceeded. Statistically, noise should account for 1 such occurrence per 1 $cm^2$ scanned, or 1 false positive per 1 ml sample.

The following equations and mathematical relationships were utilized in the theoretical modeling that was carried out in the examples.

1. Poisson Random Variable Equation:

$$P_{(I)} = e^{-G} G^I / I!$$

where I is the number of photons in a given interval;
P is the probability of I photons occurring in a given interval; and
G is the average probability of photons occurring in a given interval.

2. General Relationships:
T=seconds/1 $cm^2$ scan.
D=spot dimension, microns.
Photon Burst Time (microseconds)=$T(D^2)/1 \times 10^8$
where $1 \times 10^8$ is the number of $microns^2$ per $cm^2$.
Scan Speed (cm/sec)=$1 \times 10^4 / TD$
Nucleic Acid Signal (photon counts/photon burst time)= $FRTD^2 / 1 \times 10^8$
where F is the number of fluorescent dye molecules/nucleic acid;
and R is the detected photon count rate/dye molecule (50,000 photons/second/molecule assumed).
Background Signal (photon counts/photon burst time)= $BTD^4 / 1 \times 10^8$
where B is the average background signal in photon counts/second/$micron^2$.
NSB Signal (photon counts/photon burst time)=$ZTRD^4 / 1 \times 10^8$
where Z is the number of fluorescent dye molecules/$micron^2$ non-specifically bound to the optical surface.

With the signals expressed on a photon burst time basis, they are useful in the Poisson Random Variable equation as follows:
I=Nucleic Acid Signal;
this is the minimum nucleic acid signal (photons/burst time) for 1 false positive/$cm^2$.
G=Background Signal+NSB Signal;
this is the average photon count/burst time for all non-nucleic acid sources.

$$P < D^2 / 1 \times 10^8$$

This condition sets the statistical occurrence of false positives to less than 1 in a complete 1 $cm^2$ scan. With these relationships, curves of nucleic acid counting performance under various conditions were generated as described in the following examples.

15. Example 15

Figure 35:
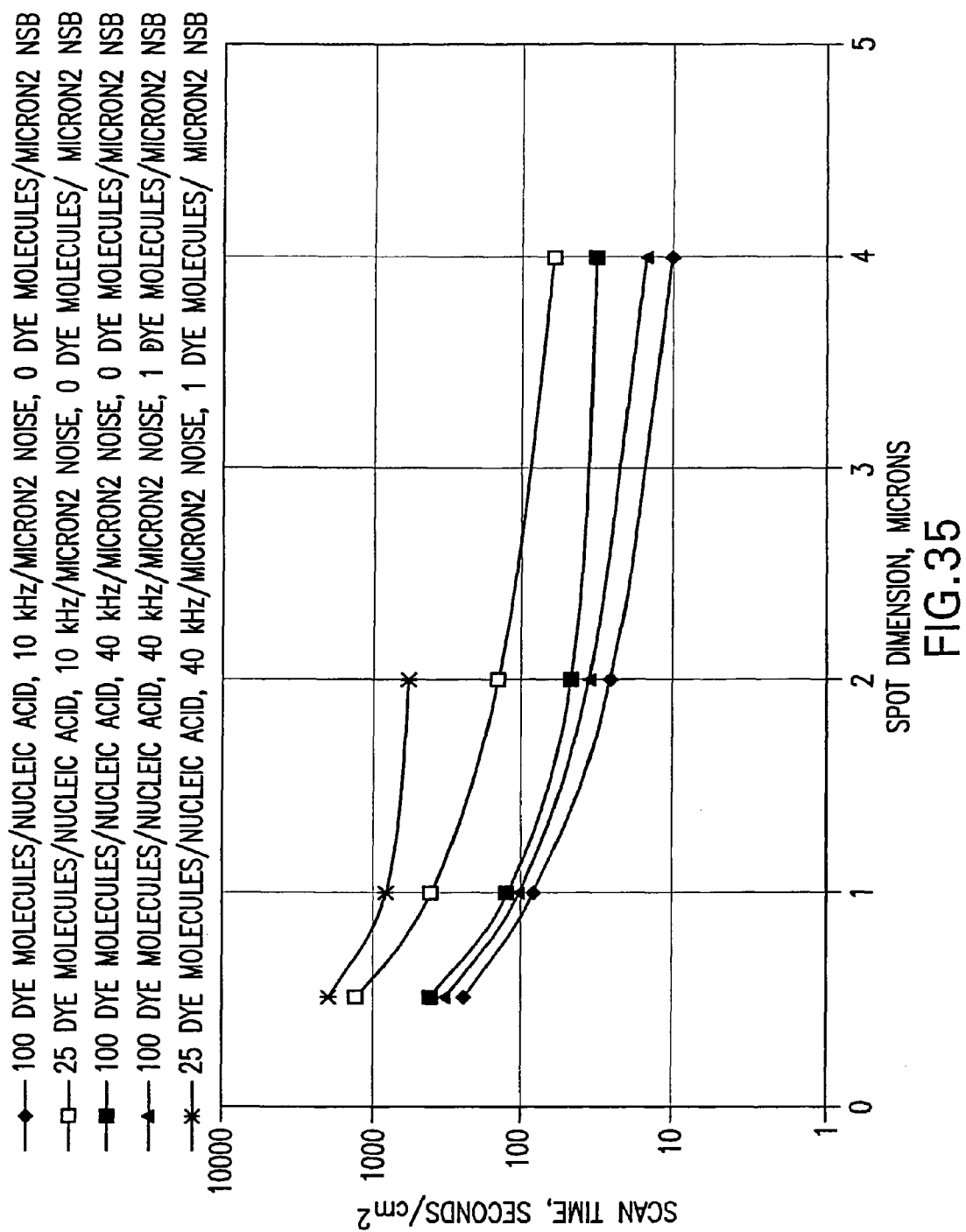
FIG. 35 is a graph of scan time vs. spot dimension for five detection conditions.

FIG. 35 is a graph of scan time vs. spot dimension for the following five detection conditions:
1. 100 dye molecules/nucleic acid, 10 khz/micron$^2$ noise, 0 dye molecules/micron NSB;
2. 1100 dye molecules/nucleic acid, 40 khz/micron noise, 0 dye molecules/micron$^2$ NSB;
3. 1100 dye molecules/nucleic acid, 40 khz/micron noise, 1 dye molecules/micron NSB;
4. 25 dye molecules/nucleic acid, 10 khz/micron$^2$ noise, 0 dye molecules/micron NSB; and
5. 25 dye molecules/nucleic acid, 40 khz/micron$^2$ noise, 1 dye molecule/micron$^2$ NSB.

As shown in the graph of FIG. 35, by setting a scan time limit of 200 seconds, manifestation of all but the noisiest 25 dye molecules/nucleic acid case is possible with a 2 micron spot. No data is presented for this case with spot dimensions larger than 2 microns, since the curve turns rapidly upward for spot dimensions between 2 and 3 microns as the SNR approaches 2.

16. Example 16

FIGS. 36-39 are graphs of scan time vs. signal/noise, where:

signal to noise ratio (SNR)=Nucleic Acid Signal/
Background Signal+NSB Signal

Figure 36:
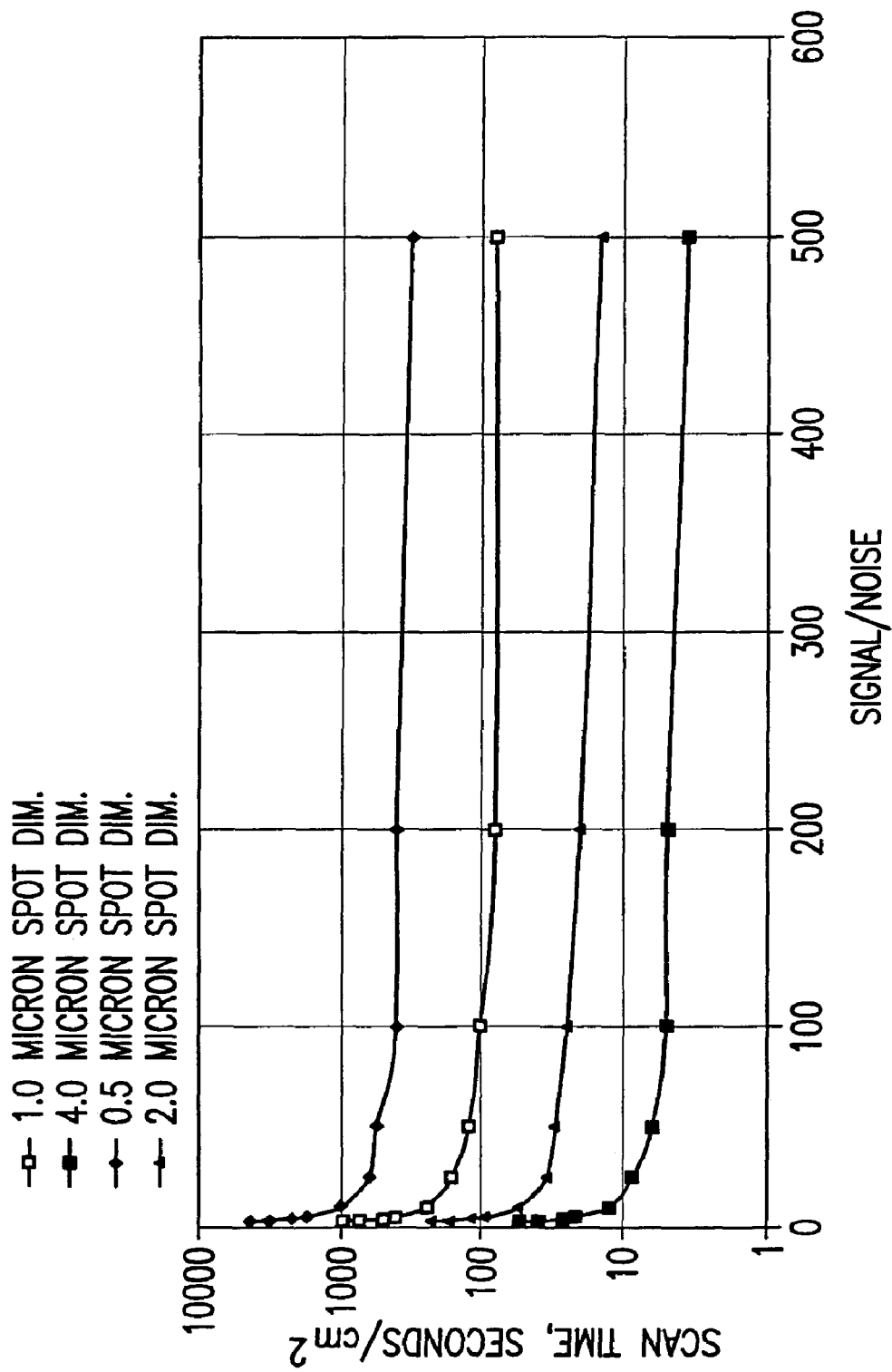
FIG. 36 is a graph for the conditions of 100 dye molecules/nucleic acid at various spot dimensions, and between 2 and 500 signal-to-noise ratio (SNR).
Figure 37:
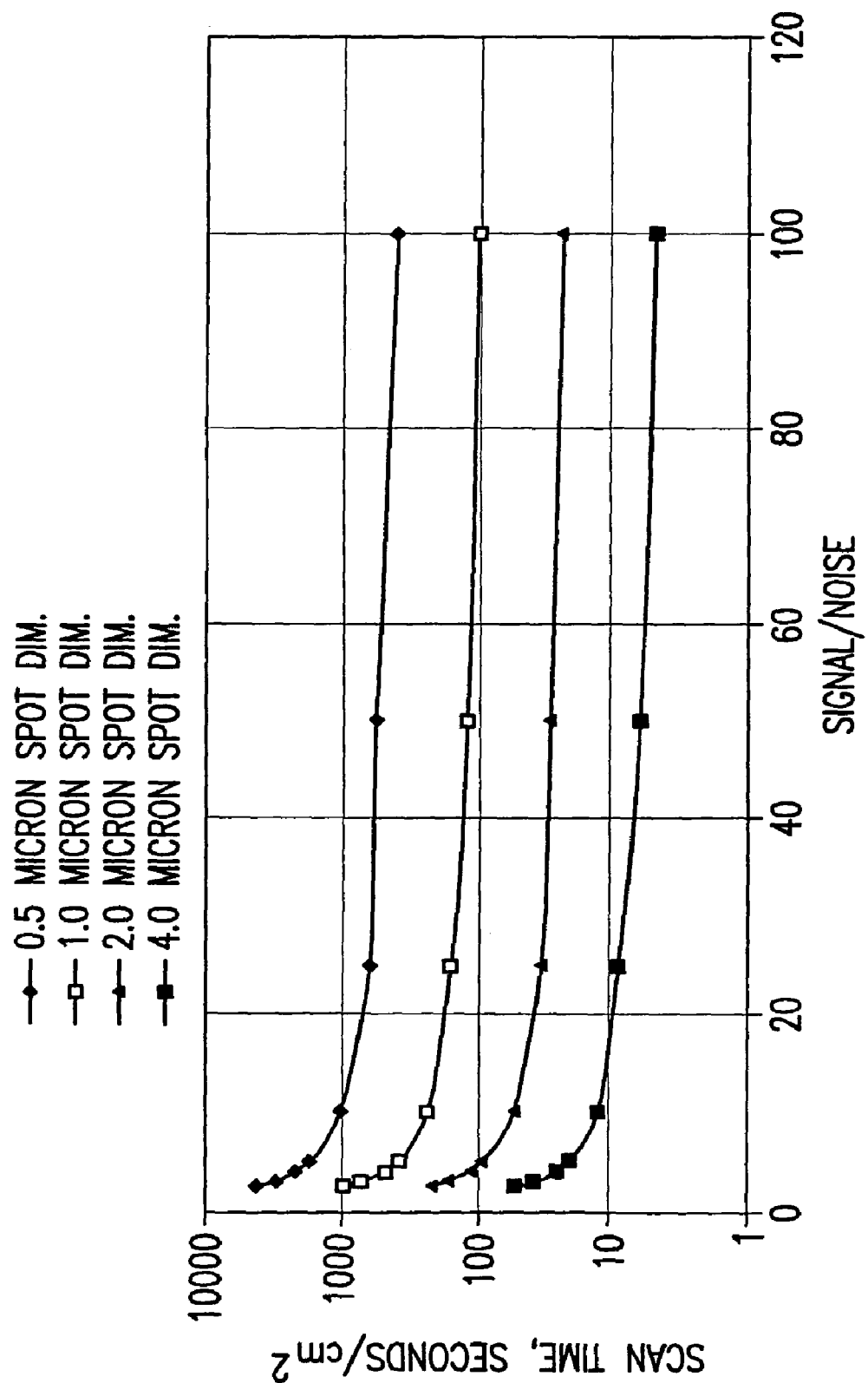
FIG. 37 is a graph for the conditions of 100 dye molecules/nucleic acid at various spot dimensions, and between 2 and 100 SNR.
Figure 38:
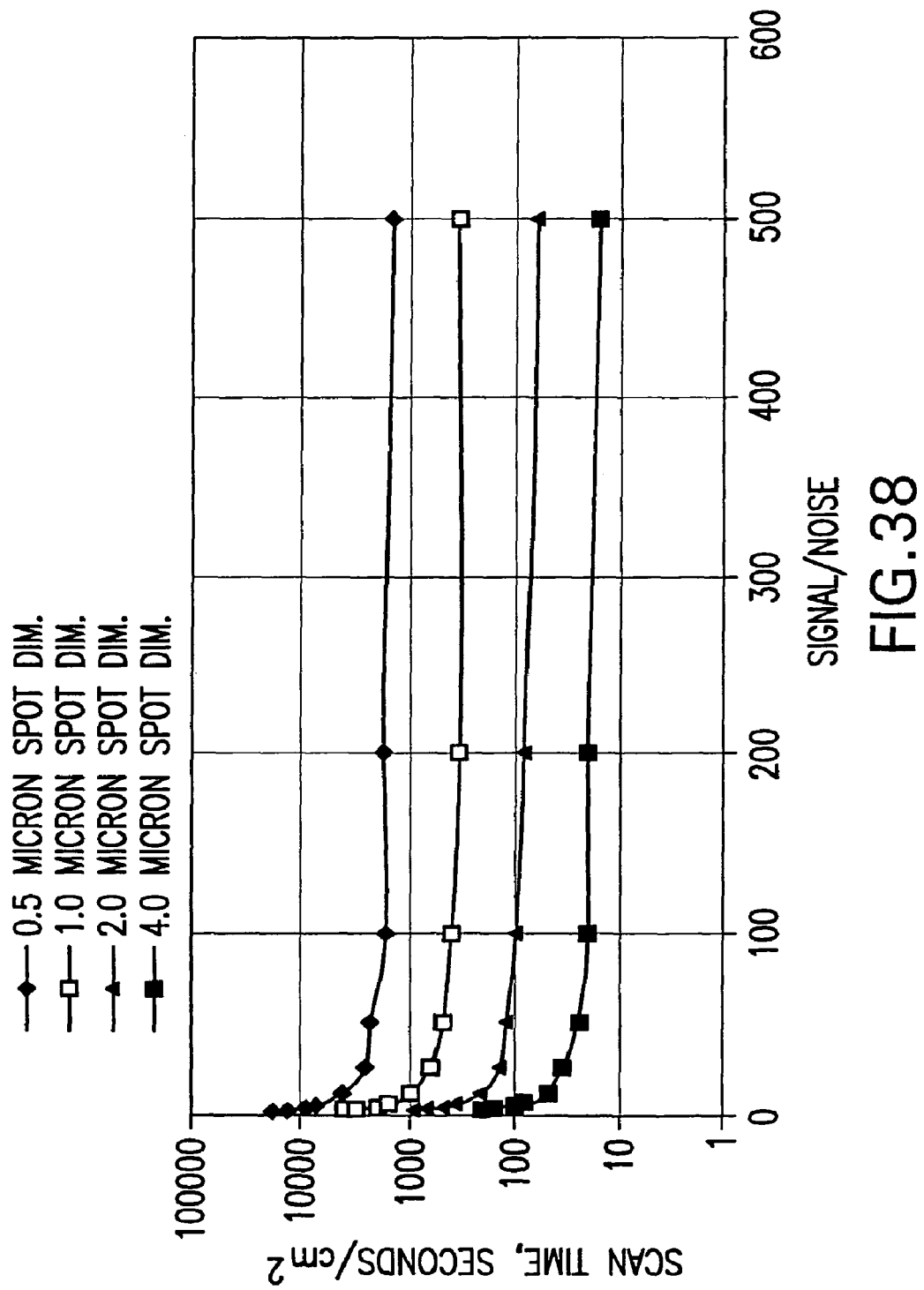
FIG. 38 is a graph for the conditions of 25 dye molecules/nucleic acid at various spot dimensions, and between 2 and 500 SNR.
Figure 39:
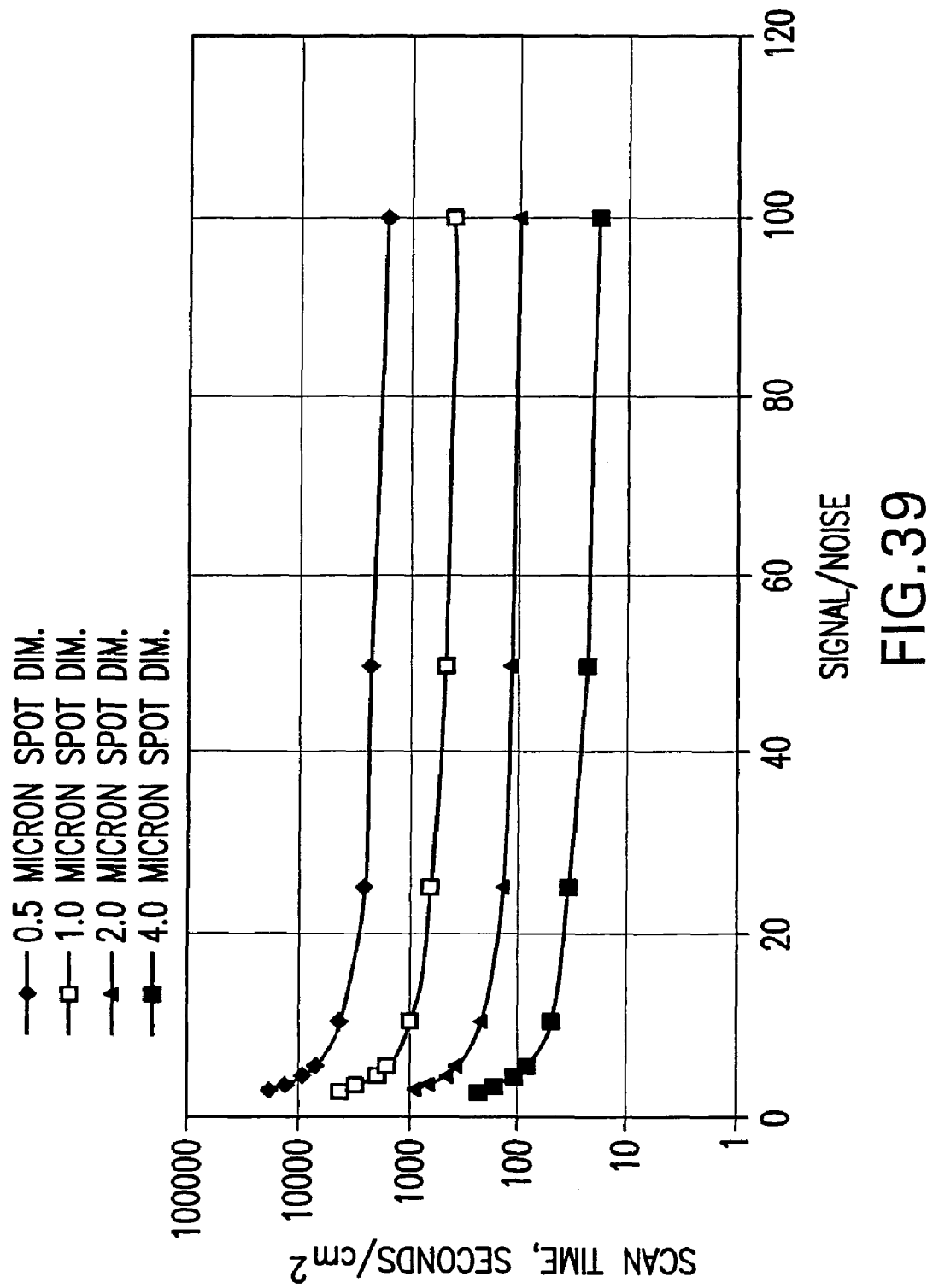
FIG. 39 is a graph for the conditions of 100 dye molecules/nucleic acid at various spot dimensions, and between 2 and 100 SNR.

The graph of FIG. 36 was generated for the conditions of 100 dye molecules/nucleic acid at various spot dimensions, and between 2 and 500 SNR. The graph of FIG. 37 was generated for the conditions of 100 dye molecules/nucleic acid at various spot dimensions, with an expanded scale between 2 and 100 SNR. The graph of FIG. 38 was generated for the conditions of 25 dye molecules/nucleic acid at various spot dimensions, and between 2 and 500 SNR. The graph of FIG. 39 was generated for the conditions of 25 dye molecules/nucleic acid at various spot dimensions with an expanded scale between 2 and 100 SNR.

The actual values of SNR at the left end of each of the graphs of FIGS. 36-39 are 2.5, 3.0, 4.0, 5.0, and 10.0. The graphs of FIGS. 36-39 reveal that scan times increase dramatically at SNR lower than about 10. Scan times for SNRs lower than 2.5 have not been calculated other than to observe as SNR ratio falls lower than 2.5, scan times become enormous.

Based on the theoretical modeling, fastest scanning is achieved with the largest spot until SNR issues begin to dominate. Referring again to FIG. 37, the point shown for 25 dye molecules/nucleic acid, 40 kHz/micron2 noise, 1 dye molecule/micron2 NSB at 2 micron spot dimension, has an SNR of 3.472. This is the same SNR found at 4 micron spot dimension for the 100 dye molecule/nucleic acid, 40 kHz/micron2 noise, and 1 dye molecule/micron2 NSB case. Both curves are relatively flat. A complete plot of theses curves would show a strong upturn in scanning time, approaching infinity, as the SNR falls towards 1. It appears that the minimum useful SNR is approximately 3.

As long as NSB is present as isolated dye molecules, it is additive with general background noise and the SNR prediction is valid. Any mechanism that causes dye molecules to concentrate into a region similar in size to a spot size used for scanning, such as staining of surface bound nonspecific nucleic acids, may result in the erroneous counting of a non-specific nucleic acid as a specific nucleic acid.

17. Example 17

Figure 40:
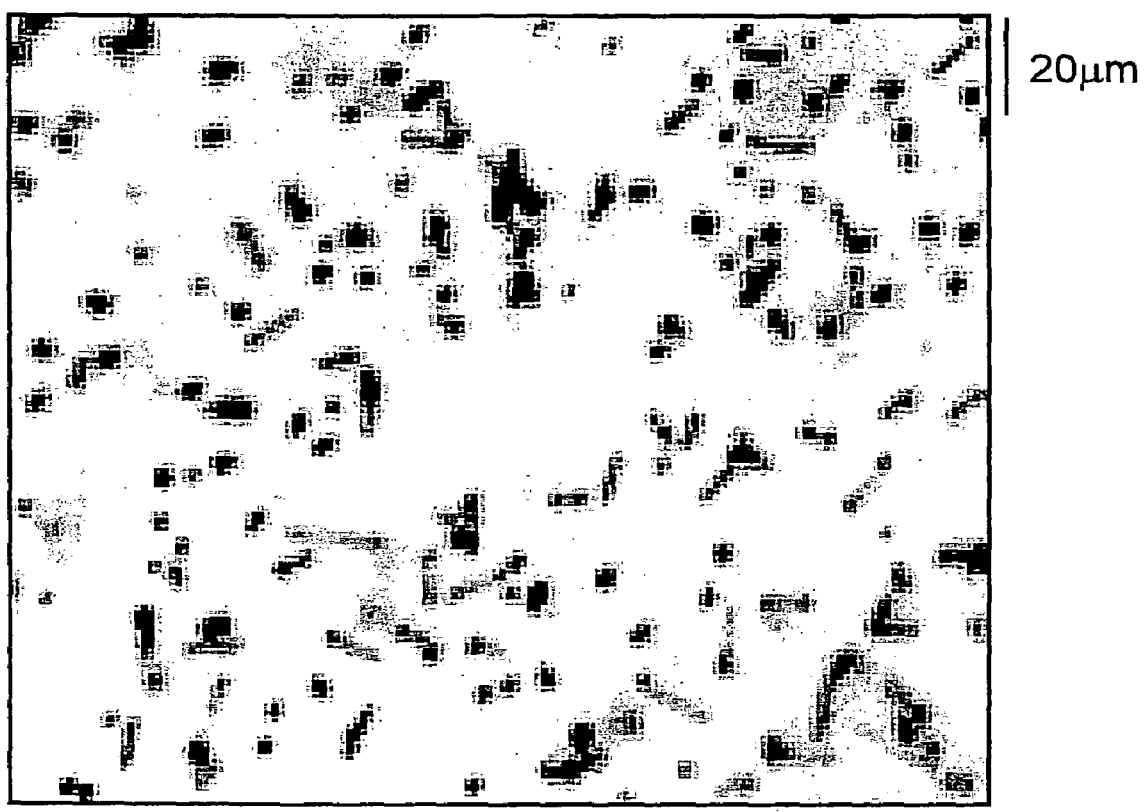
FIG. 40 is a high magnification negative image photomicrograph of lambda phage DNA of 48,502 base pair length localized on an unmodified 0.2 micron pore size Anopore membrane filter and stained with YOYO-1 dye.

FIG. 40 is a high magnification negative image photomicrograph of lambda phage DNA of 48,502 base pair length localized on an unmodified 0.2 micron pore size Anopore membrane filter and stained with YOYO-1 dye, which was imaged according to the technique described in Example 3. FIG. 40 clearly shows the DNA on the surface of the membrane filter, with DNA molecular shape readily apparent. The lighter elongated shapes in FIG. 40 correspond to fully extended, linearized DNA and the darker globular shapes correspond to collapsed molecular conformations. Additionally, intermediate structures are readily apparent, where a linear tail is seen in conjunction with a dark spot, representing partial molecular elongation.

18. Example 18

The viral load of a sample is to be determined by nucleic acid counting. A numerical example of correlating the initial sample viral load concentration from the counted nucleic acids may be based on the following values:

| | |
|---|---|
| 1. Virion Lysing Efficiency | 99% |
| 2. Sample volume | 200 ul |
| 3. Nucleic Acid Capture Efficiency | 85% |
| 4. Nucleic Acid Labeling Efficiency | 95% |
| 5. Nucleic Acid Detection Efficiency | 99% |
| 6. Detected Membrane Percentage | 25% |
| 7. System Linearity | 95% |

During the assay, an image of the analysis membrane can show 1,000 detected discrete labeled nucleic acids. Starting with parameter 7 and working backwards, 1000 detected discrete nucleic acids equates to 1,053 (1000/.95) actual nucleic acids due to system linearity. That is to say, the detector cannot accurately count all nucleic acids at certain concentrations. Since only 25% of the entire membrane filtration area was imaged, the 1,053 nucleic acids counted represents 4,212 (1,053/0.25) nucleic acids on the entire filter from the sample. Additionally, only a percentage of the nucleic acids can be detected for other reasons, and only a percentage of the nucleic acids were labeled to allow for detection. Accordingly, the 4,212 nucleic acids represent 4,478 (4,212/0.99× 0.95) nucleic acids that were on the filter. The 4,478 nucleic acids on the filter actually represent 5,269 (4,478/0.85) nucleic acids that actually flowed through the filter, because only 85% of those nucleic acids were actually retained on the filter. The 5,269 nucleic acids that flowed through the filter were derived from 200 ul of initial sample, or a concentration of 10,538 (5,269/0.2 mls) nucleic acids/ml of sample. Finally, lysis conditions are known to produce suitable nucleic acids from target virions at 95% efficiency. Accordingly, the 10,538 nucleic acids/ml calculated represents 10,644 (10,538/0.99) actual virions present in a milliliter of patient sample.

19. Example 19

0.2 micron 47 millimeter diameter Anopore membranes were dye modified as follows: 3 milliliters of EDAPS (ethylenediaminopropyl trimethoxysilane) was dissolved into 27 milliliters of high purity water with mixing. The solution was filtered through a 25-millimeter diameter Anotop filter (Whatman, 0.2 micron) to remove all particulate, gelled reagents, precipitate, etc. Dry Anopore membranes were then completely immersed in the filtered solution. The solution, including the immersed membranes, was sonicated briefly, then placed in a vacuum oven and the air evacuated to aid in membrane wetting. After 5 minutes total immersion time, the wet membranes were carefully removed from the solution and rinsed twice by immersion into 100 milliliters of high purity water with gentle mixing to remove unbound silane reagent. The membranes were similarly rinsed in 100 milliliters of 5×TE buffer to neutralize surface bound amino groups, then again in 100 milliliter of high purity water.

The moist membranes were dehydrated for approximately 3 hours in a warm (100 degree C.) oven under vacuum. The dry EDAPS membranes were then immersed in a freshly prepared and filtered solution of amino reactive dye (Procion MX, Reactive Blue 4, DTAF, etc.) containing approximately 0.5 gram of dye in 50 milliliters of high purity water. Air bubbles were again removed by sonication and vacuum. The membranes remain in the dye solution at room temperature for approximately 4 hours. The darkly colored membranes were rinsed repeatedly with high purity water then dried. The stained, dry membranes are hydrophilic and easily filter water.

20. Example 20

0.2 micron 47 millimeter diameter Anopore membranes were modified by inclusion of carbon black optical pigments as follows:

Approximately 0.2 grams of carbon black (Raven 5000 Ultra 2, Columbian Chemicals, Inc.) were mechanically dispersed into 1 milliliter of high purity water containing approximately 2% Tween 20 surfactant. The resulting black pigment dispersion was applied to the membrane surface, allowed to sit for a few minutes, then rinsed from the membrane with water. The resulting black membrane is optically opaque and somewhat hydrophobic but able to filter water.

21. Example 21

Anopore membranes were optically modified by electroless metal deposition as follows: Metal alloys suitable for electroless deposition are known to those skilled in the art and include nickel, phosphorous, boron, gold, palladium, silver, etc. Metallization must be controlled to allow optical modification to take place while retaining fluid filtration properties. The metallization process on Anopore membrane is generally a two-part process:

Activation-Anopore is generally non-reactive to metallization solutions. Accordingly, the membrane was activated by incorporation of palladium prior to metallization. This was accomplished as follows:

Palladium chloride was dissolved in dimethylsulfoxide (DMSO) at a final concentration of 5-milligrams/milliliter by stirring and gentle heating. 0.5 milliliters palladium chloride/DMSO solution was dissolved into 49.5 milliliters of acetone (1% solution). Dry Anopore membranes were fully immersed in the palladium chloride/DMSO/acetone solution for 1-2 minutes then removed. Hanging droplets were wicked from the membrane surface, then the membrane was allowed to air dry completely. Immersing the acetone moist membrane into diethyl ether to quickly remove the acetone/DMSO and precipitate the palladium chloride can also be performed. Additionally, water may be substituted for the acetone as diluent. In this case, acetone is used in place of diethyl ether to quickly dehydrate the membrane and precipitate the palladium chloride. Palladium chloride, present within the membrane as a uniform dispersion of particles, must be chemically reduced to metallic palladium by reaction with known reducing reagents, such as sodium borohydride, dimethylaminoborane, sodium hypophosphite, etc. prior to electrolytic metallization. In many cases this is accomplished in the final metallization reaction, where the palladium salt is reduced to catalytic metal by reaction with the metallization bath-reducing reagent prior to bulk metal deposition.

Metallization-Many formulations exist for electroless metallization. By way of example, electroless nickel alloys, containing either phosphorous or boron as alloying agents, are widely known. Both initially form optically black deposits ("black nickel") and are useful in the embodiments described herein.

Black nickel/phosphorous pigmentary deposits were formed by immersing palladium chloride activated Anopore membranes in a solution containing 30 grams/liter nickel chloride, 10 grams/liter sodium hypophosphite, 50 grams/liter ammonium chloride, pH 8-10 at a bath temperature of 90 degrees C. Upon immersion, the Anopore membrane slowly turns brown then black. Within approximately 5 minutes, the membrane is totally black with an optical absorption of greater than 3.0. These black nickel/phosphorous membranes appear slightly less hydrophilic than unmodified Anopore, but retain very high water flow rates for filtration.

Figure 42:
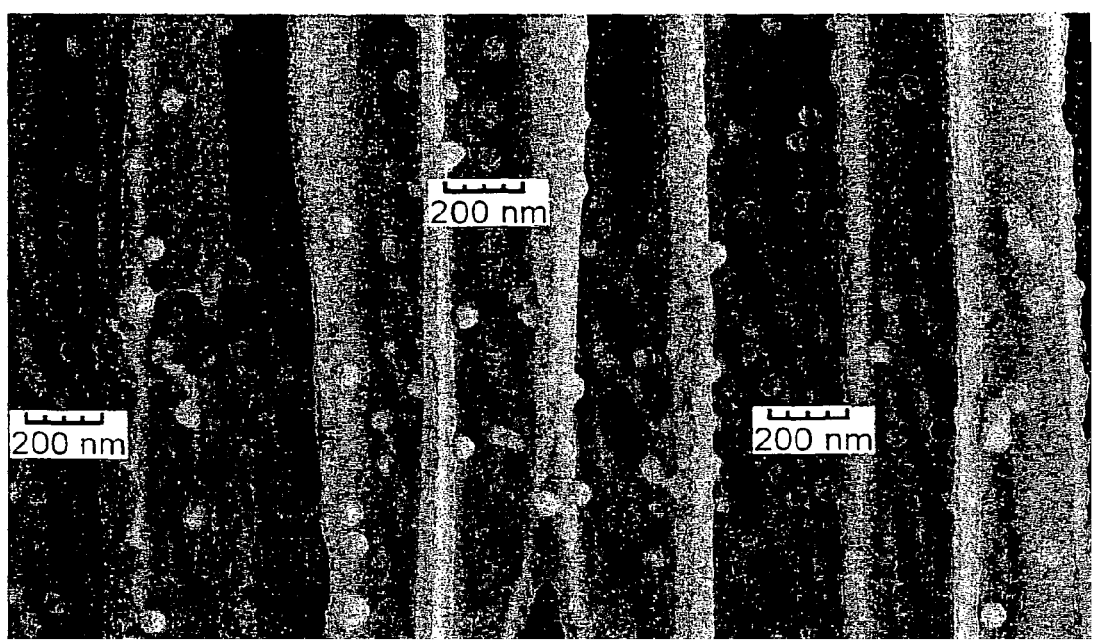
FIG. 42 is an electron micrograph of the interior of an Anopore membrane modified with nickel-boron.

Black nickel/boron pigmentary deposits were formed by immersing palladium chloride activated Anopore membranes in a solution containing 25 grams/liter nickel sulfate, 15 grams/liter sodium acetate, 4 grams/liter dimethylaminoborane, pH 5.9 at room temperature. This reaction proceeds essentially as described for the nickel/phosphorous system. In both cases, the membranes initially turn black, but eventually (10+ minutes) become metallic and non-porous as the nickel alloy continues to deposit within the pores and on exterior surfaces. FIG. 42 is an electron micrograph image of the interior of Anopore membrane modified according to Example 21 to contain black nickel/boron deposits. As is seen, the metallic deposits are exceptionally small, isolated particles and do not appear to materially effect membrane flow properties.

Figure 41:
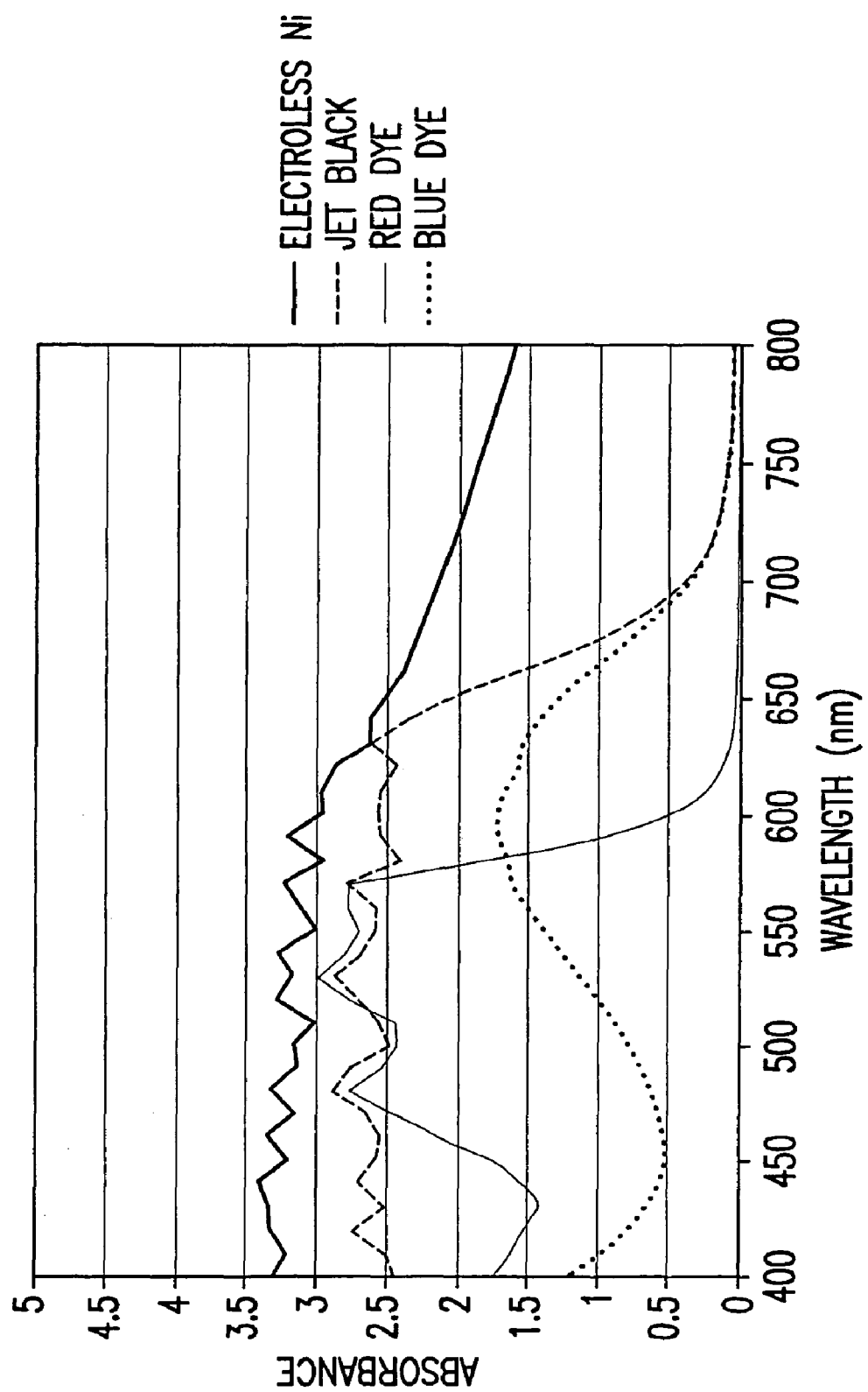
FIG. 41 shows optical absorption versus wavelength for three organic dye modified Anopore membranes and one Anopore membrane with nickel-phosphorous) deposited on the membrane (the deposited pigment membrane).

FIG. 41 shows optical absorption versus wavelength for three organic dye modified Anopore membranes and one Anopore membrane with nickel-phosphorous deposited on the membrane (the deposited pigment membrane) according to Examples 19 and 21.

FIG. 42 is an electron micrograph of the interior of an improved Anopore membrane prepared by the method described in Example 21. Bright spots are pigmentary inclusions of nickel-boron alloy deposited according to Example 21. Table 6 shows membrane autofluorescence results for a plain Anopore membrane, the three organic dye modified membranes, and the deposited pigment membrane. Data was taken with a custom designed dark field epifluorometer as shown in FIG. 14. The organic dyed membranes were modified according to Example 19 with Procion MX Jet Black, Reactive Blue 4, or Procion MX Red and the deposited pigment membrane according to Example 21 by inclusion of black nickel/phosphorous. Yellow fluorescent polystyrene beads (Molecular Probes, Inc.) having a diameter of 0.2 microns diameter were imaged against the membranes and true bead fluorescence was determined. The background signals were also measured. The data demonstrates substantial reduction in autofluorescence of Anopore membranes with non-fluorescent organic dye or deposited pigment.

TABLE 6

| Membrane Modification | 0.2 Micron Beads Yellow Fluorescent | Corrected Membrane Signal | Bead/Membrane Signal Ratio |
|---|---|---|---|
| Unmodified Membrane | 660,000 | 81,250 | 8.123 |
| Black Pigment Membrane | 320,000 | 500 | 640 |
| Organic Black Membrane | 270,000 | 20,500 | 13.17 |
| Organic Blue Membrane | 290,000 | 10,500 | 27.62 |
| Organic Red Membrane | 280,000 | 18,000 | 15.55 |

Table 7 shows NSB detectability reduction results for plain as well as the black pigmented (nickel/phosphorous) Anopore membranes previously described. Two examples are shown. Line 1 shows data for fluorescent protein NSB detectability reduction. A fluorescent protein solution was prepared containing the following:
100 nanomolar R-Phycoerythrin (Molecular Probes, Inc.)
1×TE buffer (10 millimolar Tris, 1 millimolar EDTA, pH 8.0)
1% BSA 40 microliters of the above described R-phycoerythrin solution was filtered through 150 inch diameter flow area modified and unmodified 0.2 micron Anopore membranes then rinsed once with 40 microliters of 1% BSA-1×TE buffer then rinsed with 200 microliters of plain 1×TE buffer. Fluorescent measurements were made on the instrument of FIG. 9 with the emission filter changed to a 595-nanometer center wavelength by 50 nanometer bandpass.

Line 2 shows data for fluorescent bead NSB detectability reduction. This was identical in procedure and reagents to Line 1 with 0.02 micron yellow fluorescent microbead solution (Molecular probes, Inc., 748 dilution of 1% solids stock solution, 10 nanomolar equivalent bead concentration in 1% BSA 1×TE buffer) replacing the fluorescent R-phycoerythrin solution. Fluorescence measurements were made on the instrument of FIG. 9. Both examples demonstrate substantial reduction in detected fluorescence from non-specifically bound substances.

TABLE 7

| NSB Species | Unmodified 0.2 Micron Anopore | Black Pigment Modified .2 Micron Anopore | NSB Detectability Ratio, unmodified/modified |
|---|---|---|---|
| Protein | 6,400 | 48 | 133 |
| .02 Micron Beads | 255,000 | 858 | 297 |

*Fluorescent data corrected for membrane autofluorescence.

Pigment modified membranes may be additionally modified by silanization reactions as previously described for plain membranes to impart useful surface characteristics such as NSB reduction, molecular capture, covalent attachment, etc.

22. Example 22

Nucleic acid detection and quantification by enzyme linked fluorescence (ELF) may be performed as follows:

20 complimentary biotinylated oligonucleotide probes were custom synthesized to lambda phage DNA. These probes were designed to bind specifically to the target DNA as two groups of 10 probes each. The probes in each group were designed to bind with a typical spacing of approximately 200 base pairs. This resulted in two regions of high probe binding density on the lambda DNA target. Calculations showed if the lambda DNA was fully linear, the 10 probes in each region would be contained in a length of approximately 0.6 microns. The two regions were separated by approximately 25000 base pairs, or 7-8 microns for the full linear case.

Lambda DNA was prehybridized to the above described probes as follows:

One ul of purified lambda phage DNA (500 ug/ml) was added to 499 ul of PCR Fast Start Buffer (Roche) containing 4 mM $MgCl_2$ and 200 nM of each of the 20 above described probes. This mixture was heated to 95 Degrees C. for 10 minutes, cooled to 56 degrees C. for 5 minutes, cooled to 37 degrees C. for 2 minutes, then cooled to room temperature. Unreacted probes were removed with a Qiagen PCR clean up kit following manufacturer's directions. The final lambda DNA, containing 20 hybridized biotinylated probes, was diluted to 1 ug/ml in TE buffer and frozen at −20 degrees C.

The labeled lambda DNA was visualized as follows:

Nickel-Boron modified Anopore membrane was prepared according to Example 21 and configured as shown in FIG. 18a into an assembly with 12 individual wells. This assembly was placed into a simple vacuum housing that permitted vacuum filtration by sealing tightly against the Anopore membrane. 20 ul of a 1:200 dilution of the above described prehybridized lambda DNA in TE buffer was filtered in several wells, while 20 ul of plain TE buffer was filtered in different wells. 10 ul of TBT buffer (10 mM Tris, 100 mM NaCl, 1% BSA, 0.1% Tween-20, pH 7.8) was filtered through all wells, then 10 ul additional TBT buffer was added and incubated in all wells for 5 minutes to block effects of non specific protein binding on the modified Anopore membrane. The TBT incubate was filtered, then the filter assembly was removed from the vacuum housing then reinstalled with Parafilm covering the Anopore membrane. The Parafilm seals the Anopore filter to prevent liquid flow during subsequent steps. 10 ul of a 1:50 dilution of streptavidin-alkaline phosphatase (SAP, Molecular Probes ELF kit for in situ hybridization) in TBT buffer was added to each well and incubated at room temperature for 15 minutes. The wells were aspirated to dryness, 10 ul of TBT buffer added to each well then again aspirated to dryness, then 10 ul of wash buffer (Molecular Probes ELF kit) then again aspirated to dryness. The filter assembly was removed from the vacuum housing and the parafilm removed. The assembly was then reinstalled in the vacuum housing. 100 ul of wash buffer was filtered through each well to dryness. 10 ul of ELF substrate, prepared according to the directions supplied with the Molecular Probes kit, was added to each well and incubated for a predetermined time. Briefly, the ELF substrate is a 1:10 dilution of a substrate reagent in development buffer that is filtered. Two additional reagents are added after filtration, each at 1:1,000 dilution. Each of these reagents and buffers is proprietary to Molecular Probes and are contained in the ELF kit.

After the timed ELF development incubation, each well is rinsed and aspirated with 10 ul wash buffer followed by 10 ul of distilled water. The wells are visualized on a detector as shown in FIG. 9 with the excitation source a mercury compact arc lamp with suitable filters to allow illumination at nominally 365 nm and detection filters set at 527 nm.

The results of this example are shown in FIG. 6, clearly showing a difference in the developed ELF signal between the wells containing localized DNA and the wells containing no DNA. Additionally, a time effect of ELF incubation is clearly visible as previously described.

23. Example 23

Anopore membranes were optically modified by an aqueous based electroless metallization process as follows:

All reagents ACS grade or better. The following stock solutions were prepared. Tin chloride/dimethyl sulfoxide was prepared by dissolving 1.00 grams $SnCl_2$ in 10.0 milliliters DMSO at room temperature for a final stock concentration of 100.0 milligrams/milliliter. Palladium chloride/dimethyl sulfoxide was prepared by dissolving 50 milligrams of $PdCl_2$ in 10.0 milliliters DMSO at room temperature for a final stock concentration of 5.0 milligrams/milliliter.

The following working baths were prepared. Working Bath 1—tin preactivation bath: 1.0 milliliter of tin chloride/dimethyl sulfoxide stock solution was dissolved into 99.0 milliliters of water for a final tin chloride concentration of 1.0 milligram/milliliter. This solution was stable for several days, but may eventually precipitate. Working Bath 2—palladium activating bath: 2.0 milliliters of the palladium chloride/dimethyl sulfoxide stock solution was dissolved into 98.0 milliliters of water for a final palladium chloride concentration of 0.1 milligrams/milliliter. This solution was stable for several days, but may eventually precipitate. Working Bath 3—Electroless nickel bath: 25.0 grams nickel sulfate ($NiSO_4.6H_2O$), 15.0 grams sodium acetate ($NaC_2H_3O_2.3H_2O$), 4.0 grams dimethylamine borane ($C_2H_{10}NB$), and 2.0 milligrams lead acetate ($Pb(C_2H_3O_2)_2-3H_2O$) were dissolved into 1.0 liter water. The pH was adjusted to 5.9 with acetic or sulfuric acid.

Procedure:

1. A 47 millimeter diameter 200 nanometer pore size Anopore™ filter disc was immersed into Working Bath 1 for 1-2 minutes. 80 milliliters of solution in a 100 milliliter glass beaker was used to keep the filter disc nearly vertical during the procedure without solution stirring. This step does not seem to be very sensitive to filter disc orientation, solution agitation, or residence time in the bath. Dry filter discs directly from the box without any pretreatment can be used. It is also possible to use wet filter discs from a previous processing step.

2. Remove the filter disc from Working Bath 1 and immerse it into water for approximately 1 minute to remove unreacted reagents. 500 milliliters of deionized water was used and the disc was gently and repeatedly immersed into the water. This rinse step removes non-adsorbed tin ions that may cause unwanted reactions with subsequent processing steps.

3. Remove the filter disc from the water rinse and immerse in Working Bath 2 for 1-2 minutes. This step is performed in a similar or identical manner as that in step 1. Not wishing to be bound by theory, it is believed that palladium ions are reduced to surface catalytic palladium metal atomic clusters by reaction with adsorbed tin(II) ions.

4. Remove the filter disc from Working Bath 2 and immerse in water as previously described in step 2 to remove unreacted reagents. This rinse step removes non adsorbed palladium that may cause plating bath decomposition.

5. Remove the filter disc from the water rinse followed by immersing the disc in Working Bath 3 for approximately 5 minutes with mild agitation until black. We generally continue this reaction until the filter disc is sufficiently black so as to totally obscure the light from a halogen light bulb when viewed through the black filter disc. As a representative procedure, 80 milliliters of solution in a 100 milliliter beaker with a small stir bar for agitation is used. The filter disc is generally vertical and turns dark uniformly, with slight surface variation. Without stirring, hydrogen bubbles released from the filter surface create vertical dark "tracks" due to local mixing. Fifteen black discs have been prepared from 80 milliliters of Working Bath 3 solution without adding additional reagents. In a production setting, the composition of Working Bath 3 would be continuously monitored and reagents replenished as required. With adequate water rinsing between working baths, no spontaneous decomposition of Working Bath 3 was observed.

6. Remove the filter disc from Working Bath 3 and immerse it in water as previously described to remove unreacted reagents. As the final rinse, this rinsing step can be repeated as much as necessary to ensure that all working solution reagents have been removed.

7. Remove the filter disc from the final rinse and dry. Filter discs are dried either in a vacuum chamber under reduced pressure, on the bench at room temperature, or with heated circulating air.

24. Example 24

Efficiency of PCR based detection of nucleic acids localized to unmodified Anopore membrane, with and without destabilization, was performed by one of the following 3 methods:

Method 1: 5 nanograms of purified human genomic DNA was dissolved in 100 microliters of water containing 100 millimolar NaCl was filtered through 2.5 millimeter diameter unmodified AOM contained in a filter assembly as shown in FIG. 16, followed by filtering 100 microliter water to rinse the AOM of unlocalized nucleic acids. The outlet of the filter assembly was capped then 10 microliters of destabilization buffer was added and the top capped. The sealed filter assembly was then either sonicated for approximately 1 minute in a laboratory water bath sonicator or heated to 25-100° C. for approximately 1 minute in a thermal cycling instrument. The top cap was removed, and 40 microliters of a PCR master mix comprising 1× iQ Supermix (Bio-Rad, Inc), 0.5 micromolar each $PCO_3$ and $PCO_4$ primers for human betaglobin, 1/30000 final dilution of Syber Green 1 dye (Molecular Probes, Inc), and 0.5 milligram/milliliter BSA was added and the top recapped. The filter assembly was placed in an iCycler (Bio-Rad, Inc) real time PCR instrument and cycled as follows:

Amplification
95° C. for 3:00 minutes
45 cycles of the following:
95° C. for 20 seconds Denaturation
55° C. for 30 seconds Annealing
72° C. for 30 seconds Elongation
80° C. for 10 seconds Detection
Melt Analysis
95° C. for 30 seconds
70° C. for 10 seconds
Ramp temperature in 45 steps at 0.5° C./step, hold for 10-second detection Crossing thresholds are computed by the instrument and are used to calculate PCR amplifiable localized nucleic acid.

Method 2: 5 nanograms of purified human genomic DNA was dissolved in 100 microliters of water containing 100 millimolar NaCl was filtered through 2.5 millimeter diameter unmodified AOM contained in a filter assembly as shown in FIG. 16, followed by filtering 100 microliter water to rinse the AOM of unlocalized nucleic acids. The outlet of the filter assembly was capped and 40 microliters of a PCR master mix comprising 1× iQ Supermix (Bio-Rad, Inc), 0.5 micromolar each $PCO_3$ and $PCO_4$ primers for human betaglobin, 1/30000 final dilution of Syber Green 1 dye (Molecular Probes, Inc), 0-10 millimolar destabilization ions (phosphate, borate, etc) and 0.5 milligram/milliliter BSA was added and the top capped. The filter assembly was placed in an iCycler instrument and amplified as discussed above in Method 1.

Method 3: 5 nanograms of purified human genomic DNA was dissolved in 100 microliters of water containing 100 millimolar NaCl and was filtered through 4.0 millimeter diameter unmodified AOM contained in a filter plate as shown in FIG. 18, followed by filtering 100 microliter water to rinse the AOM of unlocalized nucleic acids. The 4 millimeter AOM containing the localized nucleic acids was "punched" or broken from the plate into a conventional 0.5 milliliter thin wall PCR tube, 10 microliters of destabilization buffer was added and the top capped. The PCR tube was then either sonicated for approximately 1 minute in a laboratory water bath sonicator or heated to 25-100° C. for approximately 1 minute in a thermal cycling instrument. The top cap was removed, and 40 microliters of a PCR master mix comprising 1× iQ Supermix (Bio-Rad, Inc), 0.5 micromolar each $PCO_3$ and $PCO_4$ primers for human betaglobin, 1/30000 final dilution of Syber Green 1 dye (Molecular Probes, Inc), and 0.5 milligram/milliliter BSA was added and the top recapped. The PCR tube was placed in an iCycler (Bio-Rad, Inc) real time PCR instrument and amplified as discussed under Method 1.

Throughout this application, various publications are referenced. The disclosures of these publications in their entireties are hereby incorporated by reference into this application in order to more fully describe the compounds, compositions and methods described herein.

Various modifications and variations can be made to the microporous materials, methods, and articles described herein. Other aspects of the microporous materials, methods, and articles described herein will be apparent from consideration of the specification and practice of the microporous materials, methods, and articles disclosed herein. It is intended that the specification and examples be considered as exemplary.

What is claimed is:

1. A method for detecting an analyte, comprising
   (a) passing a fluid sample comprising the analyte through or into a microporous material, wherein the analyte is localized near the surface of the microporous material;
   (b) destabilizing at least some of the localized analyte; and
   (c) detecting the destabilized analyte,
   wherein the microporous material comprises a composite comprising a microporous material and a pigment, wherein the pigment is incorporated in the microporous material.

2. The method of claim 1, wherein the pigment is covalently attached to the microporous material.

3. The method of claim 2, wherein the pigment is attached to the microporous material by a linker.

4. The method of claim 3, wherein the linker comprises an organosilyl group.

5. The method of claim 2, wherein the pigment is attached to the microporous material by a hydroxyl group, a carboxyl group, a sulfhydryl group, an amine group, or a combination thereof present on the surface of the microporous material.

6. The method of claim 2, wherein the pigment comprises an organic dye.

7. The method of claim 6, wherein the organic dye comprises an isothiocyanate, a triazine, or an ester.

8. The method of claim 1, wherein the microporous material comprises a ceramic, a metal, carbon, or glass.

9. The method of claim 1, wherein the microporous material comprises a metal oxide.

10. The method of claim 9, wherein the metal oxide comprises aluminum oxide, zirconium oxide, titanium oxide, a zeolite, or a combination thereof.

11. The method of claim 1, wherein the microporous material comprises an inorganic electrochemically formed material or an etched material.

12. The method of claim 1, wherein the microporous material comprises micropores having a diameter of from about 0.02 microns to about 0.2 microns.

13. The method of claim 1, wherein the microporous material comprises aluminum oxide and the pigment comprises an organic dye, wherein the organic dye is covalently attached to the microporous material by a linker comprising an organosilyl group.

14. The method of claim 1, wherein the pigment is deposited on the microporous material.

15. The method of claim 14, wherein the pigment comprises an elemental metal, a metal oxide, a metal alloy, or a combination thereof.

16. The method of claim 15, wherein when the pigment comprises an elemental metal, the elemental metal comprises a transition metal.

17. The method of claim 16, wherein the transition metal comprises palladium, nickel, silver, gold, or a combination thereof.

18. The method of claim 1, wherein the labeled is optically detected with a scanning confocal epifluorometer.

19. The method of claim 1, wherein the labeled is optically detected with a CCD array based fluorescent device.

* * * * *